US008188233B2

(12) United States Patent
Condra et al.

(10) Patent No.: US 8,188,233 B2
(45) Date of Patent: May 29, 2012

(54) 1B20 PCSK9 ANTAGONISTS

(75) Inventors: Jon H. Condra, Doylestown, PA (US); Rose M. Cubbon, Fanwood, NJ (US); Holly A. Hammond, Telford, PA (US); Timothy McCabe, Doylestown, PA (US); Shilpa Pandit, Edison, NJ (US); Laurence B. Peterson, Westfield, NJ (US); Joseph C. Santoro, Belle Mead, NJ (US); Ayesha Sitlani, Metuchen, NJ (US); Dana D. Wood, Collegeville, PA (US); Henryk Mach, Ambler, PA (US); Heidi Yoder, Glenside, PA (US); Sonia M. Gregory, Blue Bell, PA (US); Jeffrey T. Blue, Telford, PA (US); Kevin Wang, Lansdale, PA (US); Peter Luo, Lansdale, PA (US); Denise K. Nawrocki, Annandale, NJ (US); Pingyu Zhong, Blue Bell, PA (US); Feng Dong, Lansdale, PA (US); Yan Li, San Jose, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 60 days.

(21) Appl. No.: 12/322,861

(22) Filed: Feb. 6, 2009

(65) Prior Publication Data

US 2009/0232795 A1 Sep. 17, 2009

Related U.S. Application Data

(60) Provisional application No. 61/063,980, filed on Feb. 7, 2008.

(51) Int. Cl.
*C07K 16/00* (2006.01)
*A61K 39/395* (2006.01)
*C12N 5/07* (2010.01)
*C12N 5/16* (2006.01)

(52) U.S. Cl. .................. 530/387.1; 424/130.1; 435/326

(58) Field of Classification Search ........................ None
See application file for complete search history.

(56) References Cited

U.S. PATENT DOCUMENTS

| | | | |
|---|---|---|---|
| 2002/0045571 | A1 | 4/2002 | Liu et al. |
| 2003/0119038 | A1 | 6/2003 | Bingham et al. |
| 2004/0009553 | A1 | 1/2004 | Glucksmann et al. |
| 2004/0248177 | A1 | 12/2004 | Abi Fadel et al. |
| 2005/0147612 | A1 | 7/2005 | Yayon et al. |
| 2009/0232795 | A1 | 9/2009 | Condra et al. |
| 2010/0040610 | A1 | 2/2010 | Sitlani et al. |
| 2010/0040611 | A1 | 2/2010 | Sparrow et al. |
| 2010/0041102 | A1 | 2/2010 | Sitlani et al. |

FOREIGN PATENT DOCUMENTS

| | | |
|---|---|---|
| EP | 1067182 | 1/2001 |
| EP | 1440981 | 7/2004 |
| EP | 1471152 | 10/2004 |
| WO | WO 01/31007 | 5/2001 |
| WO | WO 01/34768 | 5/2001 |
| WO | WO 01/57081 | 8/2001 |
| WO | WO 01/77137 | 10/2001 |
| WO | WO 01/98468 | 12/2001 |
| WO | WO 02/14358 | 2/2002 |
| WO | WO 02/46383 | 6/2002 |
| WO | WO 02/046383 | 7/2002 |
| WO | WO 02/090526 | 11/2002 |
| WO | WO 02/102993 | 12/2002 |
| WO | WO 02/102994 | 12/2002 |
| WO | WO 2004/018649 | 3/2004 |
| WO | WO 2004/097047 | 11/2004 |
| WO | WO 2007/134161 | 11/2007 |
| WO | WO 2008/057457 | 5/2008 |
| WO | WO 2008/057458 | 5/2008 |
| WO | WO 2008/057459 | 5/2008 |
| WO | WO 2008/063382 | 5/2008 |
| WO | WO 2008057459 A2 * | 5/2008 |
| WO | WO 2008/086395 | 7/2008 |
| WO | WO 2008/118386 | 10/2008 |
| WO | WO 2008/125623 | 10/2008 |
| WO | WO 2008/133647 | 11/2008 |
| WO | WO 2009/026558 | 2/2009 |
| WO | WO 2009/055783 | 4/2009 |
| WO | WO 2009/100318 | 8/2009 |
| WO | WO 2010/029513 | 3/2010 |

OTHER PUBLICATIONS

Skolnick and Fetrow. From genes to protein structure and function: novel applications of computational approaches in the genomic era. Trends in Biotechnology, 2000. vol. 18, pp. 34-39.*
Mac Callum, Martin, and Thornton. Antibody-antigen interactions: contact analysis and binding site topography. Journal of Molecular Biology, 1996. vol. 262, pp. 732-745.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.* Vajdos, Adams, Breece, Presta, De Vos, and Sidhu. Comprehensive functional maps of the antigen binding site of an anti-ErbB2 antibody obtained with shotgun scanning mutagenesis. Journal of Molecular Biology, 2002. vol. 320, pp. 415-428.*
Wu, Nie, Huse, and Watkins. Humanization of a murine monoclonal antibody by simultaneous optimization of framework and CDR residues. Journal of Molecular Biology, 1999. vol. 294, pp. 151-162.*
Rudikoff, Giusti, Cook, and Scharff. Single amino acid substitution altering antigen-binding specificity. Proceedings of the National Academy of Sciences, 1982. vol. 79, pp. 1979-1982.*

(Continued)

*Primary Examiner* — Anne M. Gussow

(57) ABSTRACT

Antagonists of human proprotein convertase subtilisin-kexin type 9 ("PCSK9") are disclosed. The disclosed antagonists are effective in the inhibition of PCSK9 function and, accordingly, present desirable antagonists for use in the treatment of conditions associated with PCSK9 activity. The present invention also discloses nucleic acid encoding said antagonists, vectors, host cells, and compositions comprising the antagonists. Methods of making PCSK9-specific antagonists as well as methods of using the antagonists for inhibiting or antagonizing PCSK9 function are also disclosed and form important additional aspects of the present disclosure.

22 Claims, 19 Drawing Sheets

OTHER PUBLICATIONS

De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*
Holm, Jafari, Sundstrom. Functional mapping and single chain construction of the anti-cytokeratin 8 monoclonal antibody TS1. Molecular Immunology, 2007. vol. 44, pp. 1075-1084.*
Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*
GenomeNet—Database: PIR, Entry: T18240, Barrell et al., LinkDB: T18240(Jul. 9, 2004) GenomeNet—Database: UniProt, Entry: A0E922_PARTE, Aury et al., LinkDB: A0E922_PARTE (Mar. 2006).
Benjannet et al., 2006 J. Biol. Chem. 281(41):30561-72 . Epub Aug. 15, 2006.
Knappik et al., 2000 J. Mol. Biol. 296:57-86.
Alborn et al., 2007 Clinical Chemistry, 53:1814-1819.
Ni et al., 2010 J Biol Chem. 285(17):12882-91. Feb. 19, 2010. [Epub ahead of print].
Lopez et al., 2008 Biochim Biophy Acta 1781:184-191.
Chan et al., Proc Natl Acad Sci U S A. Jun. 16, 2009;106(24):9820-5. Epub May 14, 2009.
Peterson et al., 2008 J Lipid Res. 49(7):1595-9.
Park et al., J. Biol. Chem. 279:50630-50638.
Bottomley et al., 2009 J Biol Chem 284(2):1313-23. Epub Nov. 10, 2008.
Benjannet et al., 2004 J. Biol. Chem. 279:48865-48875.
Molloy et al., 1994 EMBO J. 13:18-33.
Seidah et al., 2003 PNAS 100:928-933.
Zhao et al., 2006 Am J Hum Genet. Sep. 2006; 79(3): 514-523.
Lagace et al., 2006 J Clin Invest 116:2995-3005.
Cameron et al, 2006 Hum Mol Genet 15:1551-1558.
Lalanne et al., 2005 J. Lipid Research 46:1312-1319.
Cohen et al., 2006 N Engl J Med 354:1264-1272.
Cohen et al., 2005 Nat. Genet. 37:161-165, Epub Jan. 16, 2005. Erratum in: Nat Genet. Mar. 2005;37(3):328.
Maxwell et al., 2003 *J Lipid Research* 44:2109-2119.
Rashid et al., 2005 PNAS 102:5374-5379 Epub Apr. 1, 2005.
Chen et al., 2003 Pharm Res 20:1952-1960.
Akers et al., 2002 Pharm Biotech 14:47-127.
Zhang et al., 2007 J. Biol. Chem. 282:18602-18612.
Kwon et al., 2008 PNAS 105:1820-1825.
GenomeNet - Database: PIR, Entry: T18240, Barrell et al., LinkDB: T18240(Sep. 7, 2004)
GenomeNet - Database: UniProt, Entry: A0E922__PARTE, Aury et al., LinkDB: A0E922__PARTE (Mar. 2006).
Benjannet et al., 2006 J. Biol. Chem. 281(41):3056 I -72 . Epub Aug. 15, 2006.
Rabbit Anti-PCSK9 Polychlonal Antibody, Unconjugated from Cayman Chemical Catalog No. 10007185-1 2006.
Goat Anti-PCSKO Polychlonal Antibody, Unconjugated from Novus Biologicals, Catalog No. NB-300-959 2006.
Knappik et al., 2000 J. Mol. Biol. 296:57-86
Grozdanov et al., 2006 Biochem Cell Biol 84:80-92.
Alborn et al., 2007 Clinical Chemistry, 53:1814-1819
Horton et al., 2007 Trends Biochem Sciences 32:71-77.
Ni et al., 2010 J Biol Chem. 285(17):12882-91. Feb. 19, 2009 [Epub ahead of print].
Ni et al., vol. 120, No. 18, Suppl. 2, 2009, p. S477, XP008121212, ISSN: 0009-7322.
Lopez et al., 2008 Biochim Biophy Acta 1781:184-191
Lopez, 2008 Drug News & Perspectives 21:323-330.
Chan et al., Proc Natl Acad Sci U S A. Jun. 16, 2009;106(24):9820-5. Epub May 14, 2009
Peterson et al., 2008 J Lipid Res. 49(7):1595-9
Pandit et al., 2008 J Lipid Res. 49(6):1333-43. Epub Mar. 19, 2008.
Fisher et al., 2007 J Biol Chem. 282(28):20502-12. Epub May 10, 2007.
Maxwell & Breslow, 2004 PNAS 101: 7100-7105.
Naureckiene et al., 2003 Archives Biochemistry Biophysics 420:55-67.
Park et al., 2004 J. Biol. Chem. 279:50630-50638.

* cited by examiner

```
                                            |--------CH1 →
IGG1                                        ASTK GPSVFPLAPS SKSTSGGTAA LGCLVKDYFP
IGG2                                        ASTK GPSVFPLAPC SRSTSESTAA LGCLVKDYFP
IGG4                                        ASTK GPSVFPLAPC SRSTSESTAA LGCLVKDYFP
IGG2M4                                      ASTK GPSVFPLAPC SRSTSESTAA LGCLVKDYFP

                                                                C200
IGG1      EPVTVSWNSG ALTSGVHTFP AVLQSSGLYS LSSVVTVPSS SLGTQTYICN VNHKPSNTKV
IGG2      EPVTVSWNSG ALTSGVHTFP AVLQSSGLYS LSSVVTVTSS NFGTQTYTCN VDHKPSNTKV
IGG4      EPVTVSWNSG ALTSGVHTFP AVLQSSGLYS LSSVVTVPSS SLGTKTYTCN VDHKPSNTKV
IGG2M4    EPVTVSWNSG ALTSGVHTFP AVLQSSGLYS LSSVVTVTSS NFGTQTYTCN VDHKPSNTKV

          -------Hinge region----| |--------CH2 →  P238      M252      C261  D265  D270
IGG1      DKKAEPKSCD KTHTCPPCPA PELLGGPSVF LFPPKPKDTL MISRTPEVTC VVVDVSHEDP
IGG2      DKTVERKCC- --VECPPCPA PP-VAGPSVF LFPPKPKDTL MISRTPEVTC VVVDVSHEDP
IGG4      DKRVESKYGP ---PCPSCPA PEFLGGPSVF LFPPKPKDTL MISRTPEVTC VVVDVSQEDP
IGG2M4    DKTVERKCC- --VECPPCPA PP-VAGPSVF LFPPKPKDTL MISRTPEVTC VVVDVSQEDP
                                (Lower hinge)          FcRn-bind       B/C loop

                                          N297*     T307        C321      P329
IGG1      EVKFNWYVDG VEVHNAKTKP REEQYNSTYR VVSVLTVLHQ DWLNGKEYKC KVSNKALPAPI
IGG2      EVQFNWYVDG VEVHNAKTKP REEQFNSTFR VVSVLTVVHQ DWLNGKEYKC KVSNKGLPAPI
IGG4      EVQFNWYVDG VEVHNAKTKP REEQFNSTYR VVSVLTVLHQ DWLNGKEYKC KVSNKGLPSSI
IGG2M4    EVQFNWYVDG VEVHNAKTKP REEQFNSTFR VVSVLTVLHQ DWLNGKEYKC KVSNKGLPSSI
                                      C'E loop     FcRn-bind                F/G loop

                     |----CH3 →
IGG1      EKTISKAKG QPREPQVYTL PPSRDELTKN QVSLTCLVKG FYPSDIAVEW ESNGQPENNY
IGG2      EKTISKTKG QPREPQVYTL PPSREEMTKN QVSLTCLVKG FYPSDIAVEW ESNGQPENNY
IGG4      EKTISKAKG QPREPQVYTL PPSQEEMTKN QVSLTCLVKG FYPSDIAVEW ESNGQPENNY
IGG2M4    EKTISKTKG QPREPQVYTL PPSREEMTKN QVSLTCLVKG FYPSDIAVEW ESNGQPENNY

                                                     H433
IGG1      KTTPPVLDSD GSFFLYSKLT VDKSRWQQGN VFSCSVMHEA LHNHYTQKSL SLSPGK*
          (SEQ ID NO: 21)
IGG2      KTTPPMLDSD GSFFLYSKLT VDKSRWQQGN VFSCSVMHEA LHNHYTQKSL SLSPGK*
          (SEQ ID NO: 22)
IGG4      KTTPPVLDSD GSFFLYSRLT VDKSRWQEGN VFSCSVMHEA LHNHYTQKSL SLSLGK*
          (SEQ ID NO: 23)
IGG2M4    KTTPPMLDSD GSFFLYSKLT VDKSRWQQGN VFSCSVMHEA LHNHYTQKSL SLSPGK*
          (SEQ ID NO: 24)
                                                 FcRn-bind
```

FIG. 6

1B20 PCSK9 ANTAGONISTS

CROSS-REFERENCE TO RELATED APPLICATIONS

This application claims the benefit of U.S. Provisional Application No. 61/063,980, filed Feb. 7, 2008.

STATEMENT REGARDING FEDERALLY-SPONSORED R&D

Not Applicable.

REFERENCE TO MICROFICHE APPENDIX

Not Applicable.

BACKGROUND OF THE INVENTION

Proprotein convertase subtilisin-kexin type 9 (hereinafter called "PCSK9"), also known as neural apoptosis-regulated convertase 1 ("NARC-1"), is a proteinase K-like subtilase identified as the $9^{th}$ member of the secretory subtilase family; see Seidah et al., 2003 *PNAS* 100:928-933. The gene for PCSK9 localizes to human chromosome 1p33-p34.3; Seidah et al., supra. PCSK9 is expressed in cells capable of proliferation and differentiation including, for example, hepatocytes, kidney mesenchymal cells, intestinal ileum, and colon epithelia as well as embryonic brain telencephalon neurons; Seidah et al., supra.

Original synthesis of PCSK9 is in the form of an inactive enzyme precursor, or zymogen, of ~72-kDa which undergoes autocatalytic, intramolecular processing in the endoplasmic reticulum ("ER") to activate its functionality. This internal processing event has been reported to occur at the SSVFAQ↓SIPWNL$^{158}$ motif (SEQ ID NOs: 19 and 20, respectively); Benjannet et al., 2004 *J. Biol. Chem.* 279: 48865-48875. Such internal processing has been reported as a requirement of exit from the ER; Benjannet et al., supra; Seidah et al., supra. The cleaved and, thereby, activated protein is secreted in association with the cleaved peptide; supra.

The sequence for human PCSK9 (~22-kb long with 12 exons encoding a 692 amino acid protein) can be found in one instance at Deposit No. NP_777596.2. Human, mouse and rat PCSK9 nucleic acid sequences have been deposited; see, e.g., GenBank Accession Nos.: AX127530 (also AX207686), NP_705793 (also Q80W65), and P59996, respectively. PCSK9 possesses several domains found in other proprotein convertases, including an N-terminal signal sequence, a pro domain, a catalytic domain and a cysteine-rich C terminal domain. The PCSK9 catalytic domain shares high sequence similarity with the proteinase K family of subtilases and, notably, a catalytic triad of D186, H226 and S386.

PCSK9 is disclosed and/or claimed in several patent publications including, but not limited to the following: PCT Publication Nos. WO 01/31007, WO 01/57081, WO 02/14358, WO 01/98468, WO 02/102993, WO 02/102994, WO 02/46383, WO 02/90526, WO 01/77137, and WO 01/34768; US Publication Nos. US 2004/0009553 and US 2003/0119038, and European Publication Nos. EP 1 440 981, EP 1 067 182, and EP 1 471 152.

PCSK9 has been ascribed a role in the differentiation of hepatic and neuronal cells (Seidah et al., supra.), is highly expressed in embryonic liver, and has been strongly implicated in cholesterol homeostasis. Studies have suggested a specific role for PCSK9 in cholesterol biosynthesis or uptake. In a study of cholesterol-fed rats, Maxwell et al. found that PCSK9 was downregulated in a similar manner to three other genes involved in cholesterol biosynthesis, Maxwell et al., 2003 *J. Lipid Res.* 44:2109-2119. The expression of PCSK9 has, in fact, been shown to be regulated by sterol regulatory element-binding proteins ("SREBP"), as seen with other genes involved in cholesterol metabolism; supra. Later support for these findings came about through a study of PCSK9 transcriptional regulation which demonstrated that such regulation was quite typical of other genes implicated in lipoprotein metabolism; Dubuc et al., 2004 *Arterioscler. Thromb. Vasc. Biol.* 24:1454-1459. Statins have been shown to upregulate PCSK9 expression in a manner attributed to the cholesterol-lowering effects of the drugs; supra. Moreover, it has been shown that PCSK9 promoters possess two conserved sites involved in cholesterol regulation, a sterol regulatory element and an Sp1 site; supra.

Several lines of evidence demonstrate that PCSK9, in particular, lowers the amount of hepatic LDLR protein and thus compromises the liver's ability to remove LDL cholesterol from the circulation. Adenovirus-mediated overexpression of PCSK9 in the livers of mice results in the accumulation of circulating LDL-C due to a dramatic loss of hepatic LDLR protein, with no effect on LDLR mRNA levels; Benjannet et al., 2004 *J. Biol. Chem.* 279:48865-48875; Maxwell & Breslow, 2004 *PNAS* 101:7100-7105; Park et al., 2004 *J. Biol. Chem.* 279:50630-50638; and Lalanne et al., 2005 *J. Lipid Res.* 46:1312-1319. The effect of PCSK9 overexpression on raising circulating LDL-C levels in mice is completely dependent on the expression of LDLR, again, indicating that the regulation of LDL-C by PCSK9 is mediated through downregulation of LDLR protein. In agreement with these findings, mice lacking PCSK9 or in which PCSK9 mRNA has been lowered by antisense oligonucleotide inhibitors have higher levels of hepatic LDLR protein and a greater ability to clear circulating LDL-C; Rashid et al., 2005 *PNAS* 102:5374-5379; and Graham et al., 2007 *J. Lipid Res.* 48(4):763-767. In addition, lowering PCSK9 levels in cultured human hepatocytes by siRNA also results in higher LDLR protein levels and an increased ability to take up LDL-C; Benjannet et al., 2004 *J. Biol. Chem.* 279:48865-48875; and Lalanne et al., 2005 *J. Lipid Res.* 46:1312-1319. Together, these data indicate that PCSK9 action leads to increased LDL-C by lowering LDLR protein levels.

A number of mutations in the gene PCSK9 have also been conclusively associated with autosomal dominant hypercholesterolemia ("ADH"), an inherited metabolism disorder characterized by marked elevations of low density lipoprotein ("LDL") particles in the plasma which can lead to premature cardiovascular failure; see Abifadel et al., 2003 *Nature Genetics* 34:154-156; Timms et al., 2004 *Hum. Genet.* 114:349-353; Leren, 2004 *Clin. Genet.* 65:419-422. A later-published study on the S127R mutation of Abifadel et al., supra, reported that patients carrying such a mutation exhibited higher total cholesterol and apoB100 in the plasma attributed to (1) an overproduction of apoB100-containing lipoproteins, such as low density lipoprotein ("LDL"), very low density lipoprotein ("VLDL") and intermediate density lipoprotein ("IDL"), and (2) an associated reduction in clearance or conversion of said lipoproteins; Ouguerram et al., 2004 Arterioscler. Thromb. Vasc. Biol. 24:1448-1453.

Accordingly, there can be no doubt that PCSK9 plays a role in the regulation of LDL. The expression or upregulation of PCSK9 is associated with increased plasma levels of LDL cholesterol, and the corresponding inhibition or lack of expression of PCSK9 is associated with reduced LDL cholesterol plasma levels. Decreased levels of LDL cholesterol associated with sequence variations in PCSK9 have been found to confer protection against coronary heart disease; Cohen, 2006 *N. Engl. J. Med.* 354:1264-1272.

The identification of compounds and/or agents effective in the treatment of cardiovascular affliction is highly desirable. In clinical trials, reductions in LDL cholesterol levels have been directly related to the rate of coronary events; Law et al., 2003 *BMJ* 326:1423-1427. More recently, the moderate life-long reduction in plasma LDL cholesterol levels was found to correlate with a substantial reduction in the incidence of coronary events; Cohen et al., supra. This was the case even in populations with a high prevalence of non-lipid-related cardiovascular risk factors; supra. Accordingly, there is great benefit to be reaped from the managed control of LDL cholesterol levels.

The present invention advances these interests by providing antagonists of PCSK9 of use for inhibiting the activities of PCSK9 and the corresponding role PCSK9 plays in various therapeutic conditions.

SUMMARY OF THE INVENTION

The present invention relates to antagonists of PCSK9 and, in particular embodiments, those antagonists that inhibit both human and murine PCSK9 and those exhibiting preferential targeting of processed PCSK9. Broadly, protein-specific antagonists of PCSK9 (or "PCSK9-specific antagonists" as referred to herein) are PCSK9 protein binding molecules or molecules effective in the selective binding of PCSK9 and inhibition of PCSK9 function. These molecules are of import in the treatment of conditions associated with or impacted by PCSK9 function, including, but not limited to hypercholesterolemia, coronary heart disease, metabolic syndrome, acute coronary syndrome and related conditions. PCSK9-specific antagonists are characterized by selective recognition and binding to PCSK9. PCSK9-specific antagonists do not show significant binding to proteins other than PCSK9, other than in those specific instances where the antagonist is supplemented or designed to confer an additional, distinct specificity to the PCSK9-specific binding component.

PCSK9-specific antagonists forming particular embodiments hereof comprise (a) a heavy chain variable region comprising a CDR3 domain comprising SEQ ID NO: 17 or an equivalent of SEQ ID NO: 17, said equivalent characterized as having one or more conservative amino acid substitutions in the CDR3 domain; and/or (b) a light chain variable region comprising a CDR3 domain comprising SEQ ID NO: 7 or an equivalent of SEQ ID NO: 7, said equivalent characterized as having one or more conservative amino acid substitutions in the CDR3 domain. In specific embodiments, PCSK9-specific antagonists bind to human and/or murine PCSK9 with a $K_D$ of $1.2\times10^{-6}$ M or less. In more specific embodiments, PCSK9-specific antagonists bind to human and/or murine PCSK9 with a $K_D$ of $1\times10^{-7}$ M or less. In additional embodiments, PCSK9-specific antagonists bind to human and/or murine PCSK9 with a $K_D$ of $1\times10^{-8}$ M or less. In further embodiments, PCSK9-specific antagonists bind to human and/or murine PCSK9 with a $K_D$ of $5\times10^{-9}$ M or less, or of $1\times10^{-9}$ M or less. In select embodiments, PCSK9-specific antagonists bind to human and/or murine PCSK9 with a $K_D$ of $1\times10^{-10}$ M or less, a $K_D$ of $1\times10^{-11}$ M or less, or a $K_D$ of $1\times10^{-12}$ M or less. In specific embodiments, PCSK9-specific antagonists do not bind proteins other than PCSK9 at the above levels indicated for binding to PCSK9.

Particular embodiments of the present invention include PCSK9-specific antagonists which exhibit binding to PCSK9 at one of the above prescribed levels and compete for binding to PCSK9 with 1B20 antibody molecules. 1B20 antibody molecules form important PCSK9-specific antagonists hereof. 1B20 antibody molecules are characterized as comprising a (i) heavy chain variable region ("VH") comprising SEQ ID NO: 11; and (ii) a light chain variable region ("VL") comprising SEQ ID NO: 27. Said VH and VL regions comprise the full complement of disclosed CDRs 1, 2 and 3 for the VH (SEQ ID NOs: 13, 15 and 17) and VL regions (SEQ ID NOs: 3, 5 and 7), respectively. Examples of 1B20 antibody molecules include without limitation: (i) a Fab which comprises a light chain comprising SEQ ID NO: 1 and an Fd chain comprising amino acids comprising amino acids 1-221 of SEQ ID NO: 9 (or SEQ ID NO: 9); and (ii) a full length antibody molecule which comprises a light chain comprising SEQ ID NO: 26 and a heavy chain comprising SEQ ID NO: 25.

PCSK9-specific antagonists are effective in counteracting PCSK9-dependent inhibition of cellular LDL-uptake, and particularly human and/or murine PCSK9-dependent inhibition of cellular LDL uptake. Repeatedly, PCSK9-specific antagonist 1B20 has demonstrated dose-dependent inhibition of the effects of PCSK9 on LDL uptake. Accordingly, the disclosed PCSK9-specific antagonists are of import for lowering plasma LDL cholesterol levels. The disclosed antagonists also have utility for various diagnostic purposes, including the detection and quantification of PCSK9. Select 1B20 antagonists are, in particular, useful because of their cross-reactivity with both human and murine PCSK9. This quality enables particular 1B20 antagonists to be studied pharmacologically in murine models without having to ensure that the mice express human PCSK9. In such experiments, the murine model is sufficiently representative of the native activity of the targeted protein and the antagonist's inhibition thereof.

In specific embodiments, the present invention encompasses PCSK9-specific antagonists. In particular embodiments, the present invention encompasses antibody molecules comprising the disclosed heavy and/or light chain variable regions, equivalents of said regions having one or more conservative amino acid substitutions, and homologs thereof. Select embodiments comprise isolated PCSK9-specific antagonists that comprise disclosed CDR domains or sets of the heavy and/or light chain CDR domains, and equivalents of such domains characterized as having one or more conservative amino acid substitutions. As will be appreciated by those skilled in the art, fragments of PCSK9-specific antagonists that retain the ability to antagonize PCSK9 may be inserted into various frameworks; see, e.g., U.S. Pat. No. 6,818,418 and references contained therein, the collective disclosures of which are incorporated herein by reference, which discuss various scaffolds which may be used to display antibody loops previously selected on the basis of antigen binding. In the alternative, genes encoding for VL and VH may be joined, using recombinant methods, for example using a synthetic linker that enables them to be made as a single protein chain in which the VL and VH regions pair to form monovalent molecules, otherwise known as single chain Fvs ("ScFVs"); see, e.g., Bird et al., 1988 *Science* 242: 423-426, and Huston et al., 1988 *Proc. Natl. Acad. Sci. USA* 85:5879-5883, the disclosures of which are incorporated herein by reference.

PCSK-9 specific antagonists and fragments may be in the form of various non-antibody-based scaffolds, including but not limited to avimers (Avidia); DARPins (Molecular Partners); Adnectins (Adnexus), Anticalins (Pieris) and Affibodies (Affibody). The use of alternative scaffolds for protein binding is well appreciated in the scientific literature, see, e.g., Binz & Plückthun, 2005 *Curr. Opin. Biotech.* 16:1-11; the disclosure of which is incorporated herein by reference.

Accordingly, non-antibody-based scaffolds or antagonist molecules comprising (i) the disclosed heavy and/or light chain variable region CDR3 sequences (SEQ ID NOs: 17 and 7, respectively), (ii) the disclosed heavy chain variable CDR1, CDR2 and CDR3 sequences or the disclosed light chain variable CDR1, CDR2 and CDR3 sequences: CDR1 (SEQ ID NOs: 13 and 3, respectively), CDR2 (SEQ ID NOs: 15 and 5, respectively) and CDR3 (SEQ ID NOs; 17 and 7, respectively, (iii) the full complement (SEQ ID NOs; 13, 15, 17, 3, 5 and 7) of disclosed heavy and light chain CDRs within a variable region framework of a human heavy and/or light chain sequence, respectively, or (iv) the disclosed heavy and/or light chain variable regions SEQ ID NO: 11 and/or SEQ ID NO: 27 form important embodiments of the present invention, where such scaffolds or antagonist molecules exhibit selectivity for PCSK9 and counteract PCSK9-dependent inhibition of cellular LDL-uptake. In another aspect, the present invention provides nucleic acid encoding the disclosed PCSK9-specific antagonists and, in particular embodiments, PCSK9-specific antagonists which comprise the disclosed heavy and light chains, the disclosed variable heavy and light regions and select components thereof (including CDRs 1, 2 and/or 3), particularly the disclosed respective CDR3 regions. In another aspect, the present invention provides vectors comprising said nucleic acid. The present invention, additionally, provides isolated cell(s) comprising nucleic acid encoding disclosed PCSK9-specific antagonists. In another aspect, the present invention provides isolated cell(s) comprising a polypeptide or vector of the present invention.

The present invention provides methods for making PCSK9-specific antagonists disclosed herein including but not limited to antibodies, antigen binding fragments, derivatives, chimeric molecules, fusions of any of the foregoing with another polypeptide, or alternative structures/compositions capable of specifically binding PCSK9 which comprise the disclosed sequences. The methods comprise: (i) incubating a cell comprising nucleic acid encoding the PCSK9-specific antagonist(s), or which comprises individual nucleic acids encoding one or more components thereof, said nucleic acids which, when expressed, collectively produce the antagonist(s), under conditions that allow for the expression and/or assembly of the PCSK9-specific antagonist(s), and (ii) isolating said antagonist(s) from the cell. One of skill in the art can obtain PCSK9-specific antagonists disclosed herein using standard recombinant DNA techniques as well.

The present invention provides a method for antagonizing the activity or function of PCSK9 or a noted effect of PCSK9 which comprises contacting a cell, population of cells, or tissue sample of interest expressing PCSK9 (or treated with or having therein human or murine PCSK9) with a PCSK9-specific antagonist disclosed herein under conditions that allow said antagonist to bind to PCSK9. Specific embodiments of the present invention include such methods wherein the cell is a human or murine cell. Additional embodiments are wherein the cell expresses human or murine-derived PCSK9.

In another aspect, the present invention provides a method for antagonizing the activity or function of PCSK9 or a noted effect of PCSK9 in a subject exhibiting a condition associated with PCSK9 activity, or a condition where the functioning of PCSK9 is contraindicated for a particular subject, which comprises administering to the subject a therapeutically effective amount of a PCSK9-specific antagonist of the present invention in a pharmaceutical or other composition.

The present invention, thus, encompasses a method of treating a condition associated with PCSK9 activity, or a condition wherein the functioning of PCSK9 is contraindicated for a particular subject, which comprises administering to the subject a therapeutically effective amount of a PCSK9-specific antagonist of the present invention in a pharmaceutical or other composition. In select embodiments, the condition is hypercholesterolemia, coronary heart disease, metabolic syndrome, acute coronary syndrome or related conditions.

In specific embodiments, the present invention encompasses a method of administering a disclosed PCSK9-specific antagonist to a subject which comprises delivering a therapeutically effective amount of a pharmaceutical or other composition comprising a PCSK9-specific antagonist as disclosed herein.

In another aspect, the present invention provides a pharmaceutical composition or other composition comprising a PCSK9-specific antagonist of the invention characterized as comprising a pharmaceutically acceptable carrier including but not limited to an excipient, diluent, stabilizer, buffer, or alternative designed to facilitate administration of the antagonist in the desired amount to the treated individual.

The following table offers a generalized outline of the sequences discussed in the present application. The Sequence Listing including all notations, sequences and features forms an express part of the disclosure hereof:

TABLE 1

| SEQ ID NO: | DESCRIPTION |
|---|---|
| SEQ ID NO: 1 | LIGHT CHAIN ("LC"); 1B20 |
| SEQ ID NO: 2 | LIGHT CHAIN ("LC") NUCLEIC ACID; 1B20 |
| SEQ ID NO: 3 | VL CDR1; 1B20 |
| SEQ ID NO: 4 | VL CDR1 NUCLEIC ACID; 1B20 |
| SEQ ID NO: 5 | VL CDR2; 1B20 |
| SEQ ID NO: 6 | VL CDR2 NUCLEIC ACID; 1B20 |
| SEQ ID NO: 7 | VL CDR3; 1B20 |
| SEQ ID NO: 8 | VL CDR3 NUCLEIC ACID; 1B20 |
| SEQ ID NO: 9 | Fd CHAIN inclusive of linkers and tags; 1B20 |
| SEQ ID NO: 10 | Fd CHAIN NUCLEIC ACID; 1B20 |
| SEQ ID NO: 11 | VH; 1B20 |
| SEQ ID NO: 12 | VH NUCLEIC ACID; 1B20 |
| SEQ ID NO: 13 | VH CDR1; 1B20 |
| SEQ ID NO: 14 | VH CDR1 NUCLEIC ACID; 1B20 |
| SEQ ID NO: 15 | VH CDR2; 1B20 |
| SEQ ID NO: 16 | VH CDR2 NUCLEIC ACID; 1B20 |
| SEQ ID NO: 17 | VH CDR3; 1B20 |
| SEQ ID NO: 18 | VH CDR3 NUCLEIC ACID; 1B20 |
| SEQ ID NO: 19 | FRAGMENT OF PROCESSING SITE |
| SEQ ID NO: 20 | FRAGMENT OF PROCESSING SITE |
| SEQ ID NO: 21 | Constant domain of IgG1 |
| SEQ ID NO: 22 | Constant domain of IgG2 |
| SEQ ID NO: 23 | Constant domain of IgG4 |
| SEQ ID NO: 24 | Constant domain of IgG2m4 |
| SEQ ID NO: 25 | 1B20 IgG2m4 Heavy Chain ("HC") |
| SEQ ID NO: 26 | 1B20 IgG Light (Kappa) Chain |
| SEQ ID NO: 27 | VL; 1B20 |
| SEQ ID NO: 28 | VL NUCLEIC ACID; 1B20 |
| SEQ ID NO: 29 | 1B20 IgG2m4 HC NUCLEIC ACID |
| SEQ ID NO: 30 | 1B20 IgG LC NUCLEIC ACID |
| SEQ ID NO: 31 | PRIMER |
| SEQ ID NO: 32 | PRIMER |
| SEQ ID NO: 33 | PRIMER |
| SEQ ID NO: 34 | PRIMER |
| SEQ ID NO: 35 | 1B20 IgG2m4 HC PLASMID |
| SEQ ID NO: 36 | 1B20 IgG LC PLASMID |
| SEQ ID NO: 37 | 1B20 Variant VH CDR1 Sequence |
| SEQ ID NO: 38 | 1B20 Variant VH CDR2 Sequence |
| SEQ ID NO: 39 | 1B20 Variant VH CDR3 Sequence |
| SEQ ID NO: 40 | 1B20 Variant VL CDR1 Sequence |
| SEQ ID NO: 41 | 1B20 Variant VL CDR2 Sequence |
| SEQ ID NO: 42 | 1B20 Variant VL CDR3 Sequence |
| SEQ ID NO: 43 | VL; 1B20 Variant Sequence |
| SEQ ID NO: 44 | VH; 1B20 Variant Sequence |
| SEQ ID NO: 45 | VH; 1B20 Variant Sequence F120 |

TABLE 1-continued

| SEQ ID NO: | DESCRIPTION |
|---|---|
| SEQ ID NO: 46 | VH; 1B20 Variant Sequence F116 |
| SEQ ID NO: 47 | VH; 1B20 Variant Sequence F119 |
| SEQ ID NO: 48 | VH; 1B20 Variant Sequence F113 |
| SEQ ID NO: 49 | VH; 1B20 Variant Sequence E2 |
| SEQ ID NO: 50 | VH; 1B20 Variant Sequence G4 |
| SEQ ID NO: 51 | VH; 1B20 Variant Sequence F4 |
| SEQ ID NO: 52 | VH; 1B20 Variant Sequence B9 |
| SEQ ID NO: 53 | VH; 1B20 Variant Sequence C3 |
| SEQ ID NO: 54 | VH; 1B20 Variant Sequence F2 |
| SEQ ID NO: 55 | VH; 1B20 Variant Sequence F7 |
| SEQ ID NO: 56 | VH; 1B20 Variant Sequence A7 |
| SEQ ID NO: 57 | VH; 1B20 Variant Sequence G8 |
| SEQ ID NO: 58 | VH; 1B20 Variant Sequence H4 |
| SEQ ID NO: 59 | VH; 1B20 Variant Sequence D5 |
| SEQ ID NO: 60 | VH; 1B20 Variant Sequence D4 |
| SEQ ID NO: 61 | VH; 1B20 Variant Sequence B4 |
| SEQ ID NO: 62 | VH; 1B20 Variant Sequence H1 |
| SEQ ID NO: 63 | VH; 1B20 Variant Sequence G2 |
| SEQ ID NO: 64 | VH; 1B20 Variant Sequence A1 |
| SEQ ID NO: 65 | VH; 1B20 Variant Sequence A4 |
| SEQ ID NO: 66 | VH; 1B20 Variant Sequence C2 |
| SEQ ID NO: 67 | VH; 1B20 Variant Sequence H5 |
| SEQ ID NO: 68 | VH; 1B20 Variant Sequence F6 |
| SEQ ID NO: 69 | VH; 1B20 Variant Sequence B6 |
| SEQ ID NO: 70 | VH; 1B20 Variant Sequence B1 |
| SEQ ID NO: 71 | VH; 1B20 Variant Sequence F1 |
| SEQ ID NO: 72 | VH; 1B20 Variant Sequence A8 |
| SEQ ID NO: 73 | VH; 1B20 Variant Sequence B3 |
| SEQ ID NO: 74 | VH; 1B20 Variant Sequence F8 |
| SEQ ID NO: 75 | VH; 1B20 Variant Sequence H8 |
| SEQ ID NO: 76 | VH; 1B20 Variant Sequence B5 |
| SEQ ID NO: 77 | VH; 1B20 Variant Sequence E1 |
| SEQ ID NO: 78 | VH; 1B20 Variant Sequence E8 |
| SEQ ID NO: 79 | VH; 1B20 Variant Sequence C1 |
| SEQ ID NO: 80 | VH; 1B20 Variant Sequence H3 |
| SEQ ID NO: 81 | VH; 1B20 Variant Sequence A9 |
| SEQ ID NO: 82 | VH; 1B20 Variant Sequence G7 |
| SEQ ID NO: 83 | VH; 1B20 Variant Sequence C6 |
| SEQ ID NO: 84 | VH; 1B20 Variant Sequence G6 |
| SEQ ID NO: 85 | VH; 1B20 Variant Sequence E4 |
| SEQ ID NO: 86 | VH; 1B20 Variant Sequence E5 |
| SEQ ID NO: 87 | VH; 1B20 Variant Sequence C7 |
| SEQ ID NO: 88 | VH; 1B20 Variant Sequence E3 |
| SEQ ID NO: 89 | VH; 1B20 Variant Sequence D3 |
| SEQ ID NO: 90 | VH; 1B20 Variant Sequence D8 |
| SEQ ID NO: 91 | VH; 1B20 Variant Sequence C8 |
| SEQ ID NO: 92 | VH; 1B20 Variant Sequence E5 |
| SEQ ID NO: 93 | VH; 1B20 Variant Sequence B8 |
| SEQ ID NO: 94 | VH; 1B20 Variant Sequence H7 |
| SEQ ID NO: 95 | VH; 1B20 Variant Sequence A5 |
| SEQ ID NO: 96 | VH; 1B20 Variant Sequence A3 |
| SEQ ID NO: 97 | 1B20 VARIANT VH CDR2 SEQUENCE |
| SEQ ID NO: 98 | 1B20 VARIANT VH CDR3 SEQUENCE |
| SEQ ID NO: 99 | 1B20 VARIANT VL CDR1 SEQUENCE |
| SEQ ID NO: 100 | 1B20 VARIANT VL CDR2 SEQUENCE |
| SEQ ID NO: 101 | 1B20 VARIANT VL CDR3 SEQUENCE |
| SEQ ID NO: 102 | VH; 1B20 Variant Sequence N59K |
| SEQ ID NO: 103 | VH; 1B20 Variant Sequence N59Q |
| SEQ ID NO: 104 | VH; 1B20 Variant Sequence N59R |
| SEQ ID NO: 105 | VH; 1B20 Variant Sequence W101A |
| SEQ ID NO: 106 | VH; 1B20 Variant Sequence W101F |
| SEQ ID NO: 107 | VH; 1B20 Variant Sequence W101Y |
| SEQ ID NO: 108 | VL; 1B20 Variant Sequence |
| SEQ ID NO: 109 | VH; 1B20 Variant Sequence |

BRIEF DESCRIPTION OF THE DRAWINGS

FIGS. 3A-3D have two controls: (i) a cell only control, showing the basal level of cellular LDL uptake, and (ii) a PCSK9 (5 μg/ml) control which shows the level of PCSK9-dependent loss of LDL-uptake. The titration experiments which contain 1B20 and PCSK9 were done at a fixed concentration of PCSK9 (5 μg/ml) and increasing concentrations of 1B20 shown in the graphs. As shown, 1B20 can inhibit the effect of PCSK9 on cellular LDL uptake. $IC_{50}$s for 1B20 (Fab) are 152 nM (n=5) and 145 nM (n=5) for mouse and human PCSK9 protein, respectively. $IC_{50}$s for 1B20 (IgG) are 13 nM and 22 nM for mouse and human PCSK9 protein, respectively.

FIG. 6 illustrates a sequence comparison of the constant domains of IgG1 (SEQ ID NO: 21; Fc domain of which is represented by residues 110-130 of SEQ ID NO: 21), IgG2 (SEQ ID NO: 22, Fc domain of which is represented by residues 107-326 of SEQ ID NO: 22), IgG4 (SEQ ID NO: 23; Fc domain of which is represented by residues 107-327 of SEQ ID NO: 23) and IgG2m4 (SEQ ID NO: 24; Fc domain of which is represented by residues 107-326 of SEQ ID NO: 24) isotypes.

DETAILED DESCRIPTION OF THE INVENTION

Figure 1:
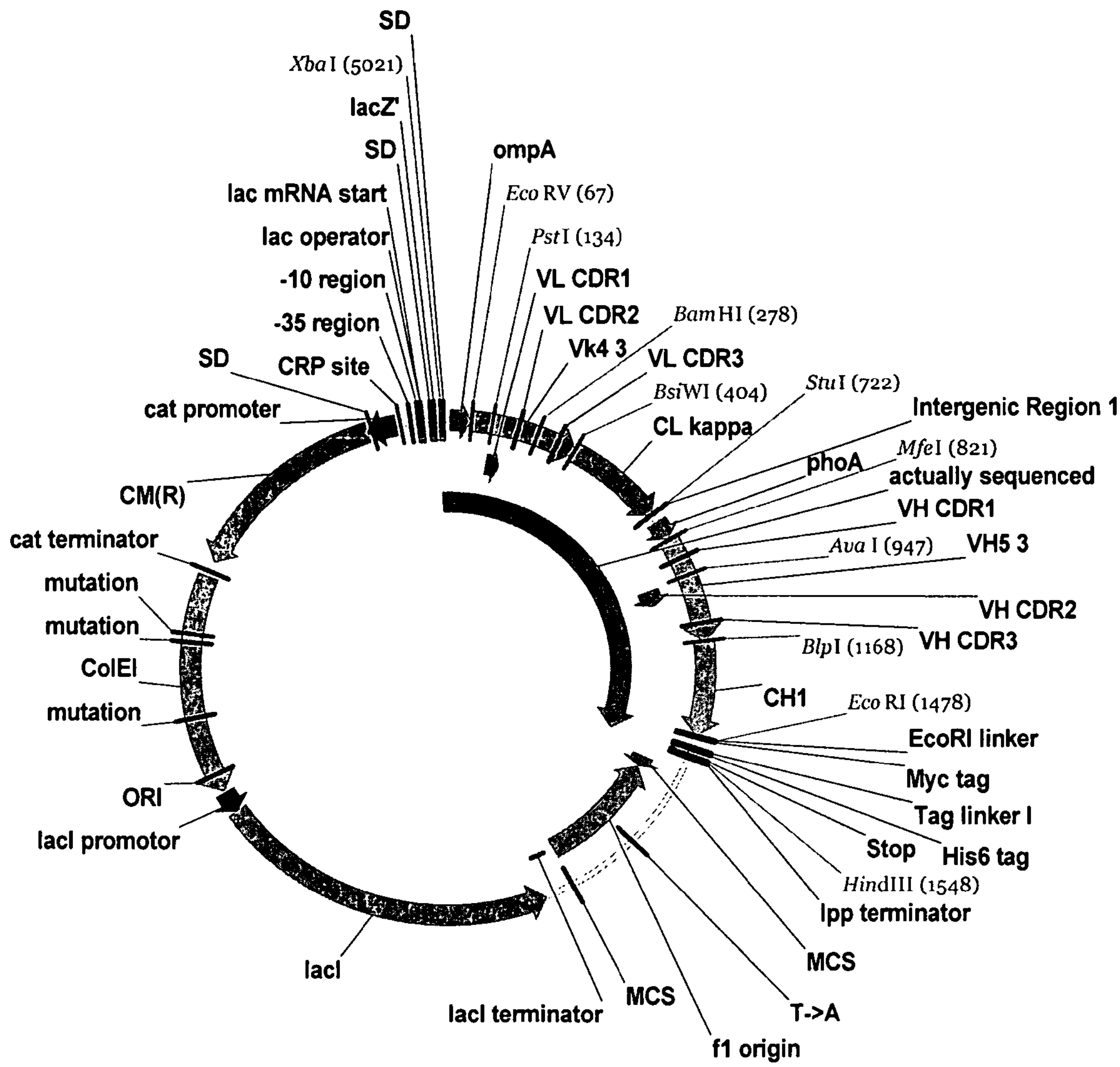
FIG. 1 illustrates Fab expression vector pMORPH_x9_MH encoding the 6CX1B20 ("1B20") Fab heavy and light chains.

The present invention relates to antagonists of PCSK9 and, in particular embodiments, those antagonists that inhibit both human and murine PCSK9 and those that preferentially target processed PCSK9. Protein-specific antagonists of PCSK9 (or "PCSK9-specific antagonists") in accordance herewith are effective in the selective binding to and inhibition of PCSK9 function and, thus, are of import in the treatment of conditions associated with or impacted by PCSK9 function, including, but not limited to, hypercholesterolemia, coronary heart disease, metabolic syndrome, acute coronary syndrome and related conditions. Use of the term "antagonist" refers to the fact that the subject molecule can antagonize the functioning of PCSK9. Use of the term "antagonizing" or derivatives thereof refers to the act of opposing, counteracting, inhibiting, neutralizing or curtailing one or more functions of PCSK9. Reference herein to PCSK9 function or PCSK9 activity refers to any function or activity that is driven by, requires, or is exacerbated or enhanced by PCSK9. PCSK9-specific antagonists as described herein have proven to be effective for counteracting human and/or murine PCSK9-dependent inhibition of cellular LDL-uptake.

One important embodiment hereof relates to 1B20 antibody molecules. Such 1B20 antibody molecules are characterized as comprising a (i) heavy chain variable region ("VH") comprising SEQ ID NO: 11; and (ii) a light chain variable region ("VL") comprising SEQ ID NO: 27. Said VH and VL regions comprise the full complement of disclosed CDRs 1, 2 and 3 for the VH (SEQ ID NOs: 13, 15 and 17) and VL regions (SEQ ID NOs: 3, 5 and 7), respectively. Examples of 1B20 antibody molecules include without limitation: (i) a Fab which comprises a light chain comprising SEQ ID NO: 1 and an Fd chain comprising amino acids 1-221 of SEQ ID NO: 9 (or SEQ ID NO: 9); and (ii) a full length antibody molecule which comprises a light chain comprising SEQ ID NO: 26 and a heavy chain comprising SEQ ID NO: 25. The select group of 1B20 antibodies demonstrate that PCSK9-specific antagonists as disclosed herein effectively inhibit both human and murine PCSK9 and may be studied pharmacologically in murine models absent the expression of human PCSK9.

The CDR definitions arrived at and disclosed herein were defined using the Morphosys software program Sequence Analysis Software ("SAS"). Applicants wish to note, however, that various other methods are available to delineate and define the start and end points of the CDR sequences, including but not limited to Kabat, 1991 *Sequences of Proteins of Immunological Interest,* 5th edit., NIH Publication no. 91-3242 U.S. Department of Health and Human Services; Clothia et al., 1987 *J. Mol. Biol.* 196:901-917; Clothia et al., 1989 *Nature* 342:877-883; Lefranc, 1997 *Immunol. Today,* 18:509; and Chen et al., 1999 *J. Mol. Biol.* 293:865-881. These and other methods have been reviewed and are well within the realm of skills possessed by those in the art; see, e.g., Honegger & Plückthun, 2001 *J. Mol. Biol.* 309:657-670. While the current inventors have employed the SAS software to define the CDRs, the present invention fully encompasses the different definitions around the sequences and the varying CDR delineations arrived at through use of any different analysis software or methods. Said use and resulting CDR definitions based on the presently disclosed sequences is fully within the scope of the present disclosure and anticipated herein.

PCSK9-specific molecules also have utility for various diagnostic purposes in the detection and quantification of PCSK9.

Disclosed PCSK9-specific antagonists are, furthermore, unique in that select embodiments have demonstrated a preferential recognition of processed PCSK9, the active form of PCSK9.

PCSK9-specific antagonists as disclosed herein are desirable molecules for lowering plasma LDL cholesterol levels and are of utility for any primate, mammal or vertebrate of commercial or domestic veterinary importance. PCSK9-specific antagonists are of utility as well to inhibit the activity of PCSK9 in any population of cells or tissues possessing the LDL receptor. The utility of the disclosed antagonists is directly measurable by assays readily available to the skilled artisan. Means for measuring LDL uptake are described in the literature; see, e.g., Barak & Webb, 1981 *J. Cell Biol.* 90:595-604, and Stephan & Yurachek, 1993 *J. Lipid Res.* 34:325330. In addition, means for measuring LDL cholesterol in plasma is well described in the literature; see, e.g., McNamara et al., 2006 *Clinica Chimica Acta* 369:158-167. The particular impact of the disclosed antagonists on cellular LDL uptake may also be measured through a method which comprises providing purified PCSK9 and labeled LDL particles to a cell sample; providing a PCSK9 antagonist to the cell sample; incubating said cell sample for a period of time sufficient to allow LDL particle uptake by the cells; quantifying the amount of label incorporated into the cell; and identifying those antagonists that result in an increase in the amount of quantified label taken up by the cells as compared with that observed when PCSK9 is administered alone. An additional method for measuring the impact of the disclosed antagonists comprises providing purified PCSK9 and labeled LDL particles to a cell sample; providing a PCSK9 antagonist to the cell sample; incubating said cell sample for a period of time sufficient to allow LDL particle uptake by the cells; isolating cells of the cell sample by removing the supernate; reducing non-specific association of labeled LDL particles (whether to the plate, the cells, or anything other than the LDL receptor); lysing the cells; quantifying the amount of label retained within the cell lysate; and identifying those antagonists that result in an increase in the amount of quantified label taken up by the cells as compared with that observed when PCSK9 is administered alone. Antagonists that result in an increase in the amount of quantified label are PCSK9 antagonists.

Any type of cell bearing the LDL receptor can be employed in the above methods including, but not limited to HEK cells, HepG2 cells, and CHO cells. LDL particles derived from any source are of use in the above-described assays. In particular assays, the LDL particles are fresh particles derived from blood. This can be accomplished by any method available to the skilled artisan including, but not limited to, the method of Havel et al., 1955 *J. Clin. Invest.* 34: 1345-1353. The LDL particles may be labeled with fluorescence. The labeled LDL particles may have incorporated therein visible wavelength excited fluorophore 3,3'-dioctadecylindocarbocyanine iodide (dil(3)) to form the highly fluorescent LDL derivative dil(3)-LDL. Any label which enables the skilled artisan to detect LDL in the cellular lysate may be used. An LDL analog may be used that would only become detectable (e.g., become fluorescent or fluoresce at a different wavelength, etc.) when metabolized intracellularly or, for instance, if it were to become associated with (or dissociated from) other molecules in the process of becoming internalized (e.g. a FRET assay, in which an LDL analog would become associated with a secondary fluor, or else be dissociated from a quencher). Any means available in the art for detecting internalization of labeled LDL particles can be employed. The incubation time for the LDL particles and PCSK9 with the cells is an amount of time sufficient to allow LDL particle uptake by the cells. This time may be within the range of 5 minutes to 360 minutes. The concentration of PCSK9 added to the cells may be in the range of 1 nM to 5 μM and, in specific methods, be in the range of 0.1 nM to 3 μM. One specific means by which the skilled artisan can determine a range of concentrations for a particular PCSK9 protein is to develop a dose response curve in the LDL-uptake assay. A concentration of PCSK9 can be selected that promotes close to maximal loss of LDL-uptake and is still in the linear range of the dose response curve. Typically, this concentration is ~5 times the EC-50 of the protein extracted from the dose response curve. The concentrations can vary by protein.

Broadly, PCSK9-specific antagonists as defined herein selectively recognize and specifically bind to PCSK9. An antibody is typically said to specifically bind an antigen when the dissociation constant is $\leqq 1$ μM, preferably $\leqq 100$ nM and most preferably $\leqq 10$ nM. Use of the terms "selective" or "specific" herein, further, refers to the fact that the disclosed antagonists do not show significant binding to proteins other than PSCK9, except in those specific instances where the antagonist is supplemented or designed to confer an additional, distinct specificity to the PCSK9-specific binding portion (as, for example, in bispecific or bifunctional molecules where the molecule is designed to bind two molecules or effect two functions, at least one of which is to specifically bind PCSK9). In specific embodiments, PCSK9-specific antagonists bind to human and/or murine PCSK9 with a $K_D$ of $1.2\times10^{-6}$ M or less. In more specific embodiments, PCSK9-specific antagonists bind to human and/or murine PCSK9 with a $K_D$ of $5\times10^{-7}$ M or less, of $2\times10^{-7}$ M or less, or of $1\times10^{-7}$ M or less. In additional embodiments, PCSK9-specific antagonists bind to human and/or murine PCSK9 with a $K_D$ of $1\times10^{-8}$ M or less. In further embodiments, PCSK9-specific antagonists bind to human and/or murine PCSK9 with a $K_D$ of $5\times10^{-9}$ M or less, or of $1\times10^{-9}$ M or less. In select embodiments, PCSK9-specific antagonists bind to human and/or murine PCSK9 with a $K_D$ of $1\times10^{-10}$ M or less, a $K_D$ of $1\times10^{-11}$ M or less, or a $K_D$ of $1\times10^{-12}$ M or less. In specific embodiments, PCSK9-specific antagonists do not bind proteins other than PCSK9 at the above $K_D$s. $K_D$ refers to the dissociation constant obtained from the ratio of $K_d$ (the dissociation rate of a particular binding molecule-target protein interaction) to $K_a$ (the association rate of the particular binding molecule-target protein interaction), or $K_d/K_a$ which is expressed as a molar concentration (M). $K_D$ values can be determined using methods well established in the art. A preferred method for determining the $K_D$ of a binding molecule is by using surface plasmon resonance, for example employing a biosensor system such as a Biacore™ (GE Healthcare Life Sciences) system.

PCSK9-specific antagonists disclosed herein have been shown to dose-dependently inhibit human and/or murine PCSK9 dependent effects on LDL uptake. Accordingly, PCSK9-specific antagonists as disclosed herein are characterized by their ability to counteract PCSK9-dependent inhibition of LDL uptake into cells. This uptake of LDL into cells by the LDL receptor is referred to herein as "cellular LDL uptake". In specific embodiments, PCSK9-specific antagonists counteract or antagonize human and/or murine PCSK9-dependent inhibition of LDL uptake into cells, exhibiting an $IC_{50}$ of less than $1.0\times10^{-6}$ M, or, in order of preference, less than $1\times10^{-7}$ M, $1\times10^{-8}$ M, $1\times10^{-9}$ M, $1\times10^{-10}$ M, $1\times10^{-11}$ M and $1\times10^{-12}$ M. The extent of inhibition by any PCSK9-specific antagonist may be measured quantitatively in statistical comparison to a control, or via any alternative method available in the art for assessing a negative effect on, or inhibition of, PCSK9 function (i.e., any method capable of assessing antagonism of PCSK9 function). In specific embodiments, the inhibition is at least about 10% inhibition. In other embodiments, the inhibition is at least 20%, 30%, 40%, 50%, 60%, 70,%, 80%, 90%, or 95%. Accordingly, PCSK9-specific antagonists capable of effecting these levels of inhibition of PCSK9 function form particular embodiments hereof.

A PCSK9-specific antagonist in accordance herewith can be any binding molecule that specifically binds human and/or murine PCSK9 protein including, but not limited to, antibody molecules as defined below, any PCSK9-specific binding structure, any polypeptide or nucleic acid structure that specifically binds PCSK9, and any of the foregoing incorporated into various protein scaffolds; including but not limited to, various non-antibody-based scaffolds, and various structures capable of affording or allowing for selective binding to PCSK9 including but not limited to small modular immunopharmaceuticals (or "SMIPs"; see, Haan & Maggos, 2004 *Biocentury* January 26); Immunity proteins (see, e.g., Chak et al., 1996 *Proc. Natl. Acad. Sci. USA* 93:6437-6442); cytochrome b562 (see Ku and Schultz, 1995 *Proc. Natl. Acad. Sci. USA* 92:6552-6556); the peptide α2p8 (see Barthe et al., 2000 *Protein Sci.* 9:942-955); avimers (Avidia; see Silverman et al., 2005 *Nat. Biotechnol.* 23:1556-1561); DARPins (Molecular Partners; see Binz et al., 2003 *J. Mol. Biol.* 332:489-503; and Forrer et al., 2003 *FEBS Lett.* 539:2-6); Tetranectins (see, Kastrup et al., 1998 *Acta. Crystallogr. D. Biol. Crystallogr.* 54:757-766); Adnectins (Adnexus; see, Xu et al., 2002 *Chem. Biol.* 9:933-942), Anticalins (Pieris; see Vogt & Skerra, 2004 *Chemobiochem.* 5:191-199; Beste et al., 1999 *Proc. Natl. Acad. Sci. USA* 96:1898-1903; Lamla & Erdmann, 2003 *J. Mol. Biol.* 329:381-388; and Lamla & Erdmann, 2004 *Protein Expr. Purif* 33:39-47); A-domain proteins (see North & Blacklow, 1999 *Biochemistry* 38:3926-3935), Lipocalins (see Schlehuber & Skerra, 2005 *Drug Discov. Today* 10:23-33); Repeat-motif proteins such as Ankyrin repeat proteins (see Sedgwick & Smerdon, 1999 *Trends Biochem. Sci.* 24:311-316; Mosavi et al., 2002 *Proc. Natl. Acad. Sci. USA* 99:16029-16034; and Binz et al., 2004 *Nat. Biotechnol.* 22:575-582); Insect Defensin A (see Zhao et al., 2004 *Peptides* 25:629-635); Kunitz domains (see Roberts et al., 1992 *Proc. Natl. Acad. Sci. USA* 89:2429-2433; Roberts et al., 1992 *Gene* 121:9-15; Dennis & Lazarus, 1994 *J. Biol. Chem.* 269:22129-22136; and Dennis & Lazarus, 1994

*J. Biol. Chem.* 269:22137-22144); PDZ-Domains (see Schneider et al., 1999 *Nat. Biotechnol.* 17:170-175); Scorpion toxins such as Charybdotoxin (see Vita et al., 1998 *Biopolymers* 47:93-100); 10$^{th}$ fibronectin type III domain (or 10Fn3; see Koide et al., 1998 *J. Mol. Biol.* 284:1141-1151, and Xu et al., 2002 *Chem. Biol.* 9:933-942); CTLA-4 (extracellular domain; see Nuttall et al., 1999 *Proteins* 36:217-227; and Irving et al., 2001 *J. Immunol. Methods* 248:31-45); Knottins (see Souriau et al., 2005 *Biochemistry* 44:7143-7155 and Lehtio et al., 2000 *Proteins* 41:316-322); Neocarzinostatin (see Heyd et al. 2003 *Biochemistry* 42:5674-5683); carbohydrate binding module 4-2 (CBM4-2; see Cicortas et al., 2004 *Protein Eng Des. Sel.* 17:213-221); Tendamistat (see McConnell & Hoess, 1995 *J. Mol. Biol.* 250:460-470, and Li et al., 2003 *Protein Eng.* 16:65-72); T cell receptor (see Holler et al., 2000 *Proc. Natl. Acad. Sci. USA* 97:5387-5392; Shusta et al., 2000 *Nat. Biotechnol.* 18:754-759; and Li et al., 2005 *Nat. Biotechnol.* 23:349-354); Affibodies (Affibody; see Nord et al., 1995 *Protein Eng.* 8:601-608; Nord et al., 1997 *Nat. Biotechnol.* 15:772-777; Gunneriusson et al., 1999 *Protein Eng.* 12:873-878); and other selective binding proteins or scaffolds recognized in the literature; see, e.g., Binz & Plückthun, 2005 *Curr. Opin. Biotech.* 16:1-11; Gill & Damle, 2006 *Curr. Opin. Biotechnol.* 17:1-6; Hosse et al., 2006 *Protein Science* 15:14-27; Binz et al., 2005 *Nat. Biotechnol.* 23:1257-1268; Hey et al., 2005 *Trends in Biotechnol.* 23:514-522; Binz & Plückthun, 2005 *Curr. Opin. Biotech.* 16:459-469; Nygren & Skerra, 2004 *J. Immunolog. Methods* 290:3-28; Nygren & Uhlen, 1997 *Curr. Opin. Struct. Biol.* 7:463-469; the disclosures of which are incorporated herein by reference. Antibodies and the use of antigen-binding fragments is well defined and understood in the literature. The use of alternative scaffolds for protein binding is well appreciated in the scientific literature as well, see, e.g., Binz & Plückthun, 2005 *Curr. Opin. Biotech.* 16: 1-11; Gill & Damle, 2006 *Curr. Opin. Biotechnol.* 17:1-6; Hosse et al., 2006 *Protein Science* 15:14-27; Binz et al., 2005 *Nat. Biotechnol.* 23:1257-1268; Hey et al., 2005 *Trends in Biotechnol.* 23:514-522; Binz & Plückthun, 2005 *Curr. Opin. Biotech.* 16:459-469; Nygren & Skerra, 2004 *J. Immunolog. Methods* 290:3-28; Nygren & Uhlen, 1997 *Curr. Opin. Struct. Biol.* 7:463-469; the disclosures of which are incorporated herein by reference. Accordingly, non-antibody-based scaffolds or antagonist molecules in accordance herewith exhibiting selectivity for PCSK9 that counteract PCSK9-dependent inhibition of cellular LDL-uptake form important embodiments of the present invention. Aptamers (nucleic acid or peptide molecules capable of selectively binding a target molecule) are one specific example. They can be selected from random sequence pools or identified from natural sources such as riboswitches. Peptide aptamers, nucleic acid aptamers (e.g., structured nucleic acid, including both DNA and RNA-based structures) and nucleic acid decoys can be effective for selectively binding and inhibiting proteins of interest; see, e.g., Hoppe-Seyler & Butz, 2000 *J. Mol. Med.* 78:426-430; Bock et al., 1992 *Nature* 355:564-566; Bunka & Stockley, 2006 *Nat. Rev. Microbiol.* 4:588-596; Martell et al., 2002 *Molec. Ther.* 6:30-34; Jayasena, 1999 *Clin. Chem.* 45:1628-1650; the disclosures of which are incorporated herein by reference.

Given 1B20's significant neutralizing activity, it is clearly of interest to identify other PCSK9-specific antagonists that bind to PCSK9 in the same manner as 1B20. One means of identifying antagonists and particularly antibodies that bind to the same region or epitope as 1B20 or an overlapping epitope is through a competition or similar assay where the candidate antibody or binding molecule would have to outcompete 1B20 for the epitope. Competitive antagonists encompassed herein are molecules that inhibit (i.e., prevent or interfere with 1B20 binding in comparison to a control) or reduce 1B20 binding by at least 50%, 60%, 70%, and 80% in order of increasing preference (even more preferably, at least 90% and, most preferably, at least 95%) at 1 μM or less with 1B20 at or below its $K_D$, and in particular those molecules that antagonize (i) PCSK9 binding to the LDL receptor, (ii) PCSK9 internalization into cells, or (iii) both PCSK9 binding to the LDL receptor and PCSK9 internalization into cells. Competition between binding members may be readily assayed in vitro for example using ELISA and/or by monitoring the interaction of the antibodies with PCSK9 in solution. The exact means for conducting the analysis is not critical. PCSK9 may be immobilized to a 96-well plate or may be placed in a homogenous solution. In specific embodiments, the ability of unlabeled candidate antibody(ies) to block the binding of labeled 1B20 can be measured using radioactive, enzyme or other labels. In the reverse assay, the ability of unlabeled antibodies to interfere with the interaction of labeled 1B20 with PCSK9 wherein said 1B20 and PCSK9 are already bound is determined. In specific embodiments, (i) PCSK9 is contacted with labeled 1B20 (an antibody molecule which comprises a VL comprising SEQ ID NO: 27 and a VH comprising SEQ ID NO: 11); (ii) PCSK9 is contacted with the candidate antibody or pool of antibodies; and (iii) antibodies capable of interrupting or preventing complexes between PCSK9 and 1B20 are identified. The readout in such an example is through measurement of bound label. 1B20 and the candidate antibody(ies) may be added in any order or at the same time.

Antibodies identified as 1B20 competitors in the above or other suitable assays may be tested for the ability to antagonize or neutralize (i) PCSK9 binding to the LDL receptor; and/or (ii) PCSK9 internalization into cells. These parameters may be measured through the use of assays similar to that employed or described in the current specification. In specific embodiments, the inhibition demonstrated by the competing antibody is at least about 10% inhibition. In other embodiments, the inhibition is at least 20%, 30%, 40%, 50%, 60%, 70%, 80%, 90% or 95%.

The present invention specifically encompasses PCSK9-specific antagonists and particularly monoclonal antibody molecules (and their corresponding amino acid and nucleic acid sequences) that selectively bind to the same epitope as 1B20 or an overlapping epitope interfering with 1B20's binding to PCSK9. Monoclonal antibodies that specifically bind to the epitope of 1B20 or an overlapping epitope antagonize or neutralize (i) PCSK9 binding to the LDL receptor; (ii) PCSK9 internalization into cells, or (iii) both. A monoclonal antibody molecule in accordance herewith may be an intact (complete or full length) antibody, a substantially intact antibody, or a portion or fragment of an antibody comprising an antigen-binding portion, e.g., a Fab fragment, Fab' fragment or F(ab')2 fragment of a murine antibody or of a chimeric antibody or of a humanized antibody or of a human antibody. Monoclonal, as used herein, refers to a homogeneous or substantially homogeneous (or pure) antibody population (i.e., at least about 90%, 91%, 92%, 93%, 94%, 95%, 96%, more preferably at least about 97% or 98%, or most preferably at least 99% of the antibodies in the population are identical and would compete in an ELISA assay for the same antigen or epitope. In specific embodiments of the present invention, the present invention provides monoclonal antibodies that (i) compete for binding to PCSK9 with a 1B20 antibody molecule, reducing 1B20 binding by at least 50% at 1 μM or less with 1B20 at or below its $K_D$, (ii) block PCSK9 binding to the LDL receptor, (iii) inhibit PCSK9 internalization into the cell, and (iv) comprise a specific antigen-binding region, VH, VL, set of CDRs or heavy CDR3, heavy and/or light chain or any variant of these components described herein.

In any of the above assays for identifying antibodies binding the same or overlapping epitope region as 1B20, binding of the known binder (i.e., 1B20 antibody molecule) as compared to the binding of the candidate binder should be distinguishable. This can (but need not) be accomplished through the use of labels on either or both molecules as will be readily appreciated by the skilled artisan. Labels, as used herein, refer to another molecule or agent incorporated into/affixed to the antibody molecule. In one embodiment, the label is a detectable marker, e.g., a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

A 1B20 antibody used for the competition assays may be any antibody molecule which is of the 1B20 description provided herein (i.e. any antibody molecule selective for PCSK9 which comprises a VL comprising SEQ ID NO: 27 and a VH comprising SEQ ID NO: 11). Examples of such antibodies include without limitation (i) a Fab which comprises a light chain comprising SEQ ID NO: 1 and an Fd chain comprising amino acids 1-221 of SEQ ID NO: 9 (or SEQ ID NO: 9); (ii) a full length antibody molecule which comprises a light chain comprising SEQ ID NO: 26 and a heavy chain comprising SEQ ID NO: 25.

Expression and selection of any of the PCSK9-specific antagonists described in the present application may be achieved using suitable technologies including, but not limited to phage display (see, e.g., International Application Number WO 92/01047, Kay et al., 1996 *Phage Display of Peptides and Proteins: A Laboratory Manual*, San Diego: Academic Press), yeast display, bacterial display, T7 display, and ribosome display (see, e.g., Lowe & Jermutus, 2004 *Curr. Pharm. Biotech.* 517-527).

Particular PCSK9-specific antagonists forming part of the present invention are antibody molecules or antibodies. "Antibody molecule" or "Antibody" as described herein refers to an immunoglobulin-derived structure with selective binding to human and/or murine PCSK9 including, but not limited to, a full length or whole antibody, an antigen binding fragment (a fragment derived, physically or conceptually, from an antibody structure), a derivative of any of the foregoing, a fusion of any of the foregoing with another polypeptide, or any alternative structure/composition which incorporates any of the foregoing for purposes of selectively binding to/inhibiting the function of PCSK9.

"Whole" antibodies or "full length" antibodies refer to proteins that comprise two heavy (H) and two light (L) chains inter-connected by disulfide bonds which comprise: (1) in terms of the heavy chains, a variable region (abbreviated herein as "$V_H$") and a heavy chain constant region which comprises three domains, $C_{H1}$, $C_{H2}$, and $C_{H3}$; and (2) in terms of the light chains, a light chain variable region (abbreviated herein as "$V_L$") and a light chain constant region which comprises one domain, $C_L$.

Antibody fragments and, more specifically, antigen binding fragments are molecules possessing an antibody variable region or segment thereof (which comprises one or more of the disclosed CDR 3 domains, heavy and/or light within framework regions of heavy and/or light chains, as appropriate), which confers selective binding to PCSK9, and particularly human and/or murine PCSK9. Antibody fragments containing such an antibody variable region include, but are not limited to the following antibody molecules: a Fab, a $F(ab')_2$, a Fd, a Fv, a scFv, bispecific antibody molecules (antibody molecules comprising a PCSK9-specific antibody or antigen binding fragment as disclosed herein linked to a second functional moiety having a different binding specificity than the antibody, including, without limitation, another peptide or protein such as an antibody, or receptor ligand), a bispecific single chain Fv dimer, an isolated CDR3, a minibody, a 'scAb', a dAb fragment, a diabody, a triabody, a tetrabody, a minibody, and artificial antibodies based upon protein scaffolds, including but not limited to fibronectin type III polypeptide antibodies (see, e.g., U.S. Pat. No. 6,703,199 and International Application Numbers WO 02/32925 and WO 00/34784) or cytochrome B; see, e.g., Nygren et al., 1997 *Curr. Opinion Struct. Biol.* 7:463-469; the disclosures of which are incorporated herein by reference. The antibody portions or binding fragments may be natural, or partly or wholly synthetically produced. Such antibody portions can be prepared by various means known by one of skill in the art, including, but not limited to, conventional techniques, such as papain or pepsin digestion.

The term "isolated" as used herein in reference to antibody molecules, PCSK9-specific antagonists in general, encoding nucleic acid or other describes a property as it pertains to the disclosed PCSK9-specific antagonists, nucleic acid or other that makes them different from that found in nature. The difference can be, for example, that they are of a different purity than that found in nature, or that they are of a different structure or form part of a different structure than that found in nature. A structure not found in nature, for example, includes recombinant human immunoglobulin structures including, but not limited to, recombinant human immunoglobulin structures with optimized CDRs. Other examples of structures not found in nature are PCSK9-specific antagonists or nucleic acid substantially free of other cellular material. Isolated PCSK9-specific antagonists are generally free of other protein-specific antagonists having different protein specificities (i.e., possess an affinity for other than PCSK9).

In one particular aspect, the present invention provides isolated PCSK9-specific antagonists which antagonize PCSK9 function. In particular embodiments, said PCSK9-specific antagonists inhibit human and/or murine PCSK9's antagonism of cellular LDL uptake by interfering with PCSK9 binding to the LDL receptor and resultant PCSK9 cell internalization. Disclosed PCSK9-specific antagonists, thus, form desirable molecules for lowering plasma LDL-cholesterol levels; see, e.g., Cohen et al., 2005 *Nat. Genet.* 37:161-

165 (wherein significantly lower plasma LDL cholesterol levels were noted in individuals heterozygous for a nonsense mutation in allele PCSK9); Rashid et al., 2005 *Proc. Natl. Acad. Sci. USA* 102:5374-5379 (wherein PCSK9-knockout mice evidenced increased numbers of LDLRs in hepatocytes, accelerated plasma LDL clearance, and significantly lower plasma cholesterol levels); and Cohen et al., 2006 *N. Engl. J. Med.* 354:1264-1272 (wherein humans heterozygous for mutated, loss of function, PCSK9 exhibited a significant reduction in the long-term risk of developing atherosclerotic heart disease).

Through repeat experiments, 1B20 antibody molecules as disclosed herein dose-dependently inhibited the effects of both human and/or murine PCSK9 on LDL uptake. In specific embodiments, the present invention, thus, encompasses isolated PCSK9-specific antagonists and, in more specific embodiments, antibody molecules comprising the heavy and/or light chain variable regions (SEQ ID NO: 11 and 27, respectively) contained within these 1B20 antibody molecules or the heavy and/or light chains, e.g., amino acids 1-221 of SEQ ID NO: 9 (or SEQ ID NO: 9) and SEQ ID NO: 1, respectively, or SEQ ID NOs: 25 and 26, respectively, as well as equivalents (characterized as having one or more conservative amino acid substitutions that do not degrade the PCSK9-selective property of 1B20) or homologs thereof. Particular embodiments comprise isolated PCSK9-specific antagonists that comprise the CDR domains disclosed herein or sets of heavy and/or light chain CDR domains disclosed herein, or equivalents thereof, characterized as having one or more conservative amino acid substitutions.

Use of the terms "domain" or "region" herein simply refers to the respective portion of the antibody molecule wherein the sequence or segment at issue will reside or, in the alternative, currently resides.

In specific embodiments, the present invention provides isolated PCSK9-specific antagonists and, in more specific embodiments, antibody molecules comprising a heavy chain variable region which comprises SEQ ID NO: 11; equivalents thereof characterized as having one or more conservative amino acid substitutions, and homologs thereof. The disclosed antagonists should counteract or inhibit human and/or murine PCSK9-dependent inhibition of cellular LDL uptake. In specific embodiments, the present invention provides homologs of the disclosed antagonists characterized as being at least 90% identical over the heavy chain variable region to SEQ ID NO: 11; said antagonists which inhibit human and/or murine PCSK9-dependent inhibition of cellular LDL uptake by at least 10%.

In specific embodiments, the present invention provides isolated PCSK9-specific antagonists and, in more specific embodiments, antibody molecules comprising a light chain variable region which comprises SEQ ID NO: 27; equivalents thereof characterized as having one or more conservative amino acid substitutions, and homologs thereof. The disclosed antagonists should counteract or inhibit human and/or murine PCSK9-dependent inhibition of cellular LDL uptake. In specific embodiments, the present invention provides homologs of the disclosed antagonists characterized as being at least 90% identical over the light chain variable region to SEQ ID NO: 27; said antagonists which inhibit human and/or murine PCSK9-dependent inhibition of cellular LDL uptake by at least 10%.

In specific embodiments, the present invention provides isolated PCSK9-specific antibody molecules which comprise a heavy chain variable region comprising SEQ ID NO: 11 and a light chain variable region comprising SEQ ID NO: 27; or equivalents thereof characterized as having one or more conservative amino acid substitutions in the prescribed sequences. Specific embodiments are said antagonists which inhibit human and/or murine PCSK9-dependent inhibition of cellular LDL uptake by at least 10%. In specific embodiments, the present invention provides homologs of the disclosed antagonists characterized as being at least 90% identical over the heavy and light chain variable regions to SEQ ID NOs: 11 and 27, respectively; said antagonists which inhibit human and/or murine PCSK9-dependent inhibition of cellular LDL uptake by at least 10%.

In particular embodiments, the present invention provides isolated PCSK9-specific antagonists and, in more specific embodiments, PCSK9 antibody molecules that comprise variable heavy CDR3 sequence SEQ ID NO: 17; and equivalents thereof characterized as having one or more conservative amino acid substitutions; specific embodiments of which inhibit human and/or murine PCSK9-dependent inhibition of cellular LDL uptake by at least 10%. Specific embodiments provide isolated antagonists which additionally comprise in the heavy chain variable region CDR1 and/or CDR2 sequences comprising SEQ ID NO: 13 and/or SEQ ID NO: 15, respectively; or equivalents thereof characterized as having one or more conservative amino acid substitutions in any one or more of the CDR sequences. In specific embodiments, the present invention provides homologs of the disclosed antagonists characterized as being at least 90% identical over the CDR3 sequences or within each of the CDR1, CDR2 and CDR3 sequences to SEQ ID NO: 17 or SEQ ID NOs: 13, 15 and 17, respectively, as appropriate; said antagonists which inhibit human and/or murine PCSK9-dependent inhibition of cellular LDL uptake by at least 10%.

In particular embodiments, the present invention provides isolated PCSK9-specific antagonists and, in more specific embodiments, antibody molecules which comprise variable light CDR3 sequence which comprises SEQ ID NO: 7; and equivalents thereof characterized as having one or more conservative amino acid substitutions; specific embodiments of which inhibit human and/or murine PCSK9-dependent inhibition of cellular LDL uptake by at least 10%. Specific embodiments provide isolated antagonists which additionally comprise in the light chain variable region CDR1 and/or CDR2 sequences comprising SEQ ID NO: 3 and/or SEQ ID NO: 5, respectively; or an equivalent thereof characterized as having one or more conservative amino acid substitutions in any one or more of the CDR sequences. In specific embodiments, the present invention provides homologs of the disclosed antagonists characterized as being at least 90% identical over the CDR3 sequences or within each of the CDR1, CDR2 and CDR3 sequences to SEQ ID NO: 7 or SEQ ID NOs: 3, 5 and 7, respectively, as appropriate; said antagonists which inhibit human and/or murine PCSK9-dependent inhibition of cellular LDL uptake by at least 10%.

In particular embodiments, the present invention provides isolated PCSK9-specific antagonists and, in more specific embodiments, antibody molecules which comprise heavy chain variable region CDR3 sequence and light chain variable region CDR3 sequence comprising SEQ ID NOs: 17 and 7, respectively; or equivalents thereof characterized as having one or more conservative amino acid substitutions in any one or more of the CDR3 sequences; specific embodiments of which inhibit human and/or murine PCSK9-dependent inhibition of cellular LDL uptake by at least 10%. In specific embodiments, the present invention provides homologs of the disclosed antagonists characterized as being at least 90% identical over the heavy and light chain variable region CDR3 sequences to SEQ ID NOs: 17 and 7, respectively; said antagonists which inhibit human and/or murine PCSK9-dependent inhibition of cellular LDL uptake by at least 10%.

Specific embodiments provide isolated PCSK9-specific antagonists and, in more specific embodiments, antibody molecules which comprise heavy chain variable region CDR1, CDR2, and CDR3 sequences and light chain variable region CDR1, CDR2, and CDR3 sequences comprising SEQ ID NOs: 13, 15, 17, 3, 5 and 7, respectively; and equivalents thereof characterized as having one or more conservative amino acid substitutions in any one or more of the CDR sequences; specific embodiments of which inhibit human and/or murine PCSK9-dependent inhibition of cellular LDL uptake by at least 10%. In specific embodiments, the present invention provides homologs of the disclosed antagonists characterized as being at least 90% identical over the heavy and light chain variable region CDR1, CDR2 and CDR3 sequences to SEQ ID NOs: 13, 15, 17, 3, 5 and 7, respectively; said antagonists which inhibit human and/or murine PCSK9-dependent inhibition of cellular LDL uptake by at least 10%.

One particular aspect of the present invention encompasses isolated PCSK9-specific antagonists and, in more specific embodiments, antibody molecules which are variants of that disclosed above which comprise a heavy chain variable region CDR3 sequence of SEQ ID NO: 39 (or, in particular embodiments, SEQ ID NO: 98) wherein the CDR3 sequence is not SEQ ID NO: 17; specific embodiments of which inhibit human and/or murine PCSK9-dependent inhibition of cellular LDL uptake by at least 10%. Further embodiments hereof additionally comprise heavy chain variable region CDR1 sequence of SEQ ID NO: 37 wherein the variant sequence is not SEQ ID NO: 13 and/or heavy chain variable region CDR2 sequence of SEQ ID NO: 38 (or, in particular embodiments, SEQ ID NO: 97) wherein the variant sequence is not SEQ ID NO: 15; specific embodiments of which inhibit human and/or murine PCSK9-dependent inhibition of cellular LDL uptake by at least 10%. In other embodiments, the present invention encompasses heavy chain variable region sequence comprising CDR1, CDR2, and CDR3 sequence which, respectively, comprises SEQ ID NOs: 37, 38 and 39 (or in particular embodiments, SEQ ID NOs: 37, 97, and 98) in the respective regions, which are, respectively, not SEQ ID NOs: 13, 15 and 17; specific embodiments of which inhibit human and/or murine PCSK9-dependent inhibition of cellular LDL uptake by at least 10%.

Another aspect of the present invention encompasses isolated PCSK9-specific antagonists and, in more specific embodiments, antibody molecules which are variants of that disclosed above which comprise a light chain variable region CDR3 sequence of SEQ ID NO: 42 (or, in particular embodiments, SEQ ID NO: 101) wherein the CDR3 sequence is not SEQ ID NO: 7; specific embodiments of which inhibit human and/or murine PCSK9-dependent inhibition of cellular LDL uptake by at least 10%. Further embodiments hereof additionally comprise light chain variable region CDR1 sequence of SEQ ID NO: 40 (or, in particular embodiments, SEQ ID NO: 99) wherein the variant sequence is not SEQ ID NO: 3 and/or light chain variable region CDR2 sequence of SEQ ID NO: 41 (or, in particular embodiments, SEQ ID NO: 100) wherein the variant sequence is not SEQ ID NO: 5; specific embodiments of which inhibit human and/or murine PCSK9-dependent inhibition of cellular LDL uptake by at least 10%. In other embodiments, the present invention encompasses light chain variable region sequence comprising CDR1, CDR2 and CDR3 sequence which, respectively, comprises SEQ ID NOs: 40, 41 and 42 (or, in particular embodiments, SEQ ID NOs: 99, 100 and 101) in the respective regions, which are, respectively, not SEQ ID NOs: 3, 5 and 7; specific embodiments of which inhibit human and/or murine PCSK9-dependent inhibition of cellular LDL uptake by at least 10%.

Additional distinct embodiments encompass isolated PCSK9-specific antagonists which comprise: (a) a heavy chain variable region comprising CDR1, CDR2 and CDR3 sequence, wherein (i) the CDR1 sequence comprises SEQ ID NO: 13 or SEQ ID NO: 37; SEQ ID NO: 37 being different in sequence from SEQ ID NO: 13; (ii) the CDR2 sequence comprises SEQ ID NO: 15, SEQ ID NO: 38 or SEQ ID NO: 97; SEQ ID NOs: 38 and 97 being different in sequence from SEQ ID NO: 15; and (iii) the CDR3 sequence comprises SEQ ID NO: 17, SEQ ID NO: 39 or SEQ ID NO: 98; SEQ ID NO: 39 and SEQ ID NO: 98 being different in sequence from SEQ ID NO: 17; and/or (b) a light chain variable region comprising CDR1, CDR2 and CDR3 sequence, wherein (i) the CDR1 sequence comprises SEQ ID NO: 3 or SEQ ID NO: 40; SEQ ID NO: 40 being different in sequence from SEQ ID NO: 3; (ii) the CDR2 sequence comprises SEQ ID NO: 5, SEQ ID NO: 41 or SEQ ID NO: 100; SEQ ID NOs: 41 and 100 being different in sequence from SEQ ID NO: 5; and (iii) the CDR3 sequence comprises SEQ ID NO: 7, SEQ ID NO: 42 or SEQ ID NO: 101; SEQ ID NO: 42 and SEQ ID NO: 101 being different in sequence from SEQ ID NO: 7; specific embodiments of which inhibit human and/or murine PCSK9-dependent inhibition of cellular LDL uptake by at least 10%.

Other aspects of the present invention encompass isolated PCSK9-specific antagonists and, in more specific embodiments, antibody molecules which are variants of that disclosed above which comprise (i) a heavy chain variable region sequence comprising CDR1, CDR2, and CDR3 sequence which, respectively, comprises SEQ ID NOs: 37, 38 and 39 (or, in particular embodiments, SEQ ID NOs: 37, 97 and 98) in the respective regions, which are, respectively, not SEQ ID NOs:13, 15 and 17; and (ii) a light chain variable region sequence comprising CDR1, CDR2 and CDR3 sequence which, respectively, comprises SEQ ID NOs: 40, 41 and 42 (or, in particular embodiments, SEQ ID NOs: 99, 100 and 101) in the respective regions, which are, respectively, not SEQ ID NOs: 3, 5 and 7; specific embodiments of which inhibit human and/or murine PCSK9-dependent inhibition of cellular LDL uptake by at least 10%.

In specific embodiments herein the CDRs are in place of the corresponding regions of 1B20 with out without conservative amino acid substitutions; specific embodiments of which inhibit human and/or murine PCSK9-dependent inhibition of cellular LDL uptake by at least 10%. In particular embodiments, the present invention encompasses isolated PCSK9-specific antagonists and, in more specific embodiments, antibody molecules comprising heavy and/or light chain variable regions comprising SEQ ID NOs: 44 and 43 (or, in particular embodiments, SEQ ID NOs: 109 and 108), respectively; said variants SEQ ID NOs which are not SEQ ID NOs: 11 and 27, respectively; specific embodiments of which inhibit human and/or murine PCSK9-dependent inhibition of cellular LDL uptake by at least 10%.

Specific embodiments include any isolated PCSK9-specific antagonist and, in more specific embodiments, antibody molecules which comprise heavy chain variable region sequence found in any of SEQ ID NOs: 45-96 and 102-107, optionally comprising a light chain variable region sequence disclosed herein (e.g., SEQ ID NO: 27); specific embodiments of which inhibit human and/or murine PCSK9-dependent inhibition of cellular LDL uptake by at least 10%.

Particular embodiments are isolated PCSK9-specific antagonists which comprise the above-described VH and VL regions in a full length antibody. Specific embodiments herein further comprise a series of amino acids selected from the group consisting of: SEQ ID NO: 21 (IgG1), SEQ ID NO: 22 (IgG2), SEQ ID NO: 23 (IgG4) and SEQ ID NO: 24 (IgG2 m4).

Conservative amino acid substitutions, as one of ordinary skill in the art will appreciate, are substitutions that replace an amino acid residue with one imparting similar or better (for the intended purpose) functional and/or chemical characteristics. Antagonists bearing such conservative amino acid substitutions can be tested for retained or better activity using functional assays available in the art or described herein. PCSK9-specific antagonists possessing one or more conservative amino acid substitutions which retain the ability to selectively bind to human PCSK9 and antagonize PCSK9 functioning at a level the same or better than 1B20 antibody molecules as described herein are referred to herein as "functional equivalents" of the disclosed antagonists and form specific embodiments of the present invention. Conservative amino acid substitutions are often ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Such modifications are not designed to significantly reduce or alter the binding or functional inhibition characteristics of the PCSK9-specific antagonist, albeit they may improve such properties. The purpose for making a substitution is not significant and can include, but is by no means limited to, replacing a residue with one better able to maintain or enhance the structure of the molecule, the charge or hydrophobicity of the molecule, or the size of the molecule. For instance, one may desire simply to substitute a less desired residue with one of the same polarity or charge. Such modifications can be introduced by standard techniques known in the art, such as site-directed mutagenesis and PCR-mediated mutagenesis. One specific means by which those of skill in the art accomplish conservative amino acid substitutions is alanine scanning mutagenesis as discussed in, for example, MacLennan et al., 1998 *Acta Physiol. Scand. Suppl.* 643:55-67, and Sasaki et al., 1998 *Adv. Biophys.* 35:1-24.

In another aspect, the present invention provides isolated PCSK9-specific antagonists and, in more specific embodiments, antibody molecules which comprise heavy and/or light chain variable regions comprising amino acid sequences that are homologous to the corresponding amino acid sequences of the disclosed antibodies, wherein the antibody molecules inhibit PCSK9-dependent inhibition of cellular LDL uptake. Specific embodiments are antagonists which comprise heavy and/or light chain variable regions which are at least 90% identical to disclosed heavy and/or light chain variable regions, respectively. Reference to "at least 90% identical" includes at least 90, 91, 92, 93, 94, 95, 96, 97, 98, 99 and 100% identical sequences along the full length of the molecule disclosed herein.

PCSK9-specific antagonists with amino acid sequences homologous to the amino acid sequences of antagonists described herein are typically produced to improve one or more of the properties of the antagonist without negatively impacting its specificity for PCSK9. One method of obtaining such sequences, which is not the only method available to the skilled artisan, is to mutate sequence encoding the PCSK9-specific antagonist or specificity-determining region(s) thereof, express an antagonist comprising the mutated sequence(s), and test the encoded antagonist for retained function using available functional assays including those described herein. Mutation may be by site-directed or random mutagenesis. As one of skill in the art will appreciate, however, other methods of mutagenesis can readily bring about the same effect. For example, in certain methods, the spectrum of mutants are constrained by non-randomly targeting conservative substitutions based on either amino acid chemical or structural characteristics, or else by protein structural considerations. In affinity maturation experiments, several such mutations may be found in a single selected molecule, whether they are randomly or non-randomly selected. There are also various structure-based approaches toward affinity maturation as demonstrated in, e.g., U.S. Pat. No. 7,117,096, PCT Pub. Nos.: WO 02/084277 and WO 03/099999; the disclosures of which are incorporated herein by reference.

As used herein, the percent homology between two amino acid or nucleic acid sequences is equivalent to the percent identity between the two sequences, and these two terms will be used interchangeably throughout. As used herein, % identity of two nucleic acid or amino acid sequences is determined using the algorithm of Karlin and Altschul (Proc. Natl. Acad. Sci. USA 90:5873-5877, 1993). Such an algorithm is incorporated into the NBLAST and XBLAST programs of Altschul et al., 1990 *J. Mol. Biol.* 215:403-410. BLAST nucleotide searches are performed with the NBLAST program, score=100, wordlength=12, to obtain nucleic acid sequences homologous to a nucleic acid molecule of the invention. BLAST protein searches are performed with the XBLAST program, score=50, wordlength=3, to obtain amino acid sequences homologous to an amino acid sequence disclosed herein. To obtain gapped alignments for comparison purposes, Gapped BLAST is utilized as described in Altschul et al., 1997 *Nucleic Acids Res.* 25:3389-3402. When utilizing BLAST and Gapped BLAST programs, the default parameters of the respective programs (e.g., XBLAST and NBLAST) are used.

Utilization of components of one or more disclosed PCSK9-specific molecules to produce other binding molecules with similar or better specificity is well within the realm of one skilled in the art. This can be accomplished, for example, using techniques of recombinant DNA technology. One specific example of this involves the introduction of DNA encoding the immunoglobulin variable region, or one or more of the CDRs, of an antibody to the variable region, constant region, or constant region plus framework regions, as appropriate, of a different immunoglobulin. Such molecules form important aspects of the present invention. Specific immunoglobulins or the corresponding sequences, into which particular disclosed sequences may be inserted or, in the alternative, form the essential part of, include but are not limited to the following antibody molecules which form particular embodiments of the present invention: a Fab (monovalent fragment with variable light (VL), variable heavy (VH), constant light (CL) and constant heavy 1 (CH1) domains), a F(ab')2 (bivalent fragment comprising two Fab fragments linked by a disulfide bridge or alternative at the hinge region), a Fd (VH and CH1 domains), a Fv (VL and VH domains), a scFv (a single chain Fv where VL and VH are joined by a linker, e.g., a peptide linker, see, e.g., Bird et al., 1988 *Science* 242:423-426, Huston et al., 1988 *PNAS USA* 85:5879-5883), a bispecific antibody molecule (an antibody molecule comprising a PCSK9-specific antibody or antigen binding fragment as disclosed herein linked to a second functional moiety having a different binding specificity than the antibody, including, without limitation, another peptide or protein such as an antibody, or receptor ligand), a bispecific single chain Fv dimer (see, e.g., PCT/US92/09965), an isolated CDR3, a minibody (single chain-CH3 fusion that self assembles into a bivalent dimer of about 80 kDa), a 'scAb' (an antibody fragment containing VH and VL as well as either CL or CH1), a dAb fragment (VH domain, see, e.g., Ward et al., 1989 *Nature* 341:544-546, and McCafferty et al., 1990 *Nature* 348:552-554; or VL domain; Holt et al., 2003 *Trends in Biotechnology* 21:484-489), a diabody (see, e.g., Holliger et al., 1993 *PNAS USA* 90:6444-6448 and International Application Number WO 94/13804), a triabody, a tetrabody, a minibody (a scFv joined to a CH3; see, e.g., Hu et al., 1996 *Cancer Res.* 56:3055-3061), IgG, IgG1, IgG2, IgG3, IgG4, IgM, IgD, IgA, IgE or any derivatives thereof, and artificial antibodies based upon protein scaffolds, including but not limited to fibronectin type III polypeptide antibodies (see, e.g., U.S. Pat. No. 6,703,199 and International Application Number WO 02/32925) or cytochrome B; see, e.g., Koide et al., 1998 *J. Molec. Biol.* 284:1141-1151, and Nygren et al., 1997 *Current Opinion in Structural Biology* 7:463-469; the disclosures of which are incorporated herein by reference. Certain antibody molecules including, but not limited to, Fv, scFv, diabody molecules or domain antibodies (Domantis) may be stabilized by incorporating disulfide bridges to line the VH and VL domains, see, e.g., Reiter et al., 1996 *Nature Biotech.* 14:1239-1245; the disclosure of which is incorporated herein by reference. Bispecific antibodies may be produced using conventional technologies (see, e.g., Holliger & Winter, 1993 *Current Opinion Biotechnol.* 4:446-449, specific methods of which include production chemically, or from hybrid hybridomas) and other technologies including, but not limited to, the BiTE™ technology (molecules possessing antigen binding regions of different specificity with a peptide linker) and knobs-into-holes engineering (see, e.g., Ridgeway et al., 1996 *Protein Eng.* 9:616-621; the disclosure of which is incorporated herein by reference). Bispecific diabodies may be produced in *E. coli*, and these molecules as other PCSK9-specific antagonists, as one of skill in the art will appreciate, may be selected using phage display in the appropriate libraries (see, e.g., International Application Number WO 94/13804; the disclosure of which is incorporated herein by reference).

Variable domains, into which CDRs of interest are inserted, may be obtained from any germ-line or rearranged human variable domain. Variable domains may also be synthetically produced. The CDR regions can be introduced into the respective variable domains using recombinant DNA technology. One means by which this can be achieved is described in Marks et al., 1992 *Bio/Technology* 10:779-783; the disclosure of which is incorporated herein by reference. A variable heavy domain may be paired with a variable light domain to provide an antigen binding site. In addition, independent regions (e.g., a variable heavy domain alone) may be used to bind antigen. The artisan is well aware, as well, that two domains of an Fv fragment, VL and VH, while perhaps coded by separate genes, may be joined, using recombinant methods, by a synthetic linker that enables them to be made as a single protein chain in which the VL and VH regions pair to form monovalent molecules (scFvs).

Specific embodiments provide the CDR(s) in germline framework regions. Framework regions, including but not limited to human framework regions, are known to those of skill in the art (e.g., a human or non-human framework). The framework regions may be naturally occurring or consensus framework regions. In one aspect, the framework region of an antibody of the invention is human (see, e.g., Clothia et al., 1998 *J. Mol. Biol.* 278:457-479 for a listing of human framework regions; said disclosure of which is incorporated herein by reference in its entirety). Specific embodiments herein provide heavy chain variable CDR3 SEQ ID NO: 17 into VH5__3 in place of the relevant CDR. Specific embodiments herein provide heavy chain variable CDR1, CDR2 and/or CDR3 sequences (SEQ ID NO:s 13, 15 and 17, respectively) into VH5__3 in place of the relevant CDRs. Specific embodiments herein provide light chain variable CDR3 SEQ ID NO: 7 into VK4__3 in place of the relevant CDR. Specific embodiments herein provide light chain variable CDR1, CDR2 and/or CDR3 sequences (SEQ ID NO:s 3, 5 and 7, respectively) into VK4__3 in place of the relevant CDRs. Specific embodiments further provide heavy chain variable CDR3SEQ ID NO: 17 and light chain variable CDR3SEQ ID NO: 7 into VH5__3 and VK4__3 germline sequences, respectively. Further embodiments provide heavy chain variable CDR1, CDR2 and/or CDR3 sequences (SEQ ID NO:s 13, 15 and 17, respectively) into VH5__3 in place of the relevant CDRs; and light chain variable CDR1, CDR2 and/or CDR3 sequences (SEQ ID NO:s 3, 5 and 7, respectively) into VK4__3 in place of the relevant CDRs.

The present invention encompasses antibody molecules that are human, humanized, deimmunized, chimeric and primatized. The invention also encompasses antibody molecules produced by the process of veneering; see, e.g., Mark et al., 1994 Handbook of Experimental Pharmacology, vol. 113: The pharmacology of monoclonal Antibodies, Springer-Verlag, pp. 105-134; the disclosure of which is incorporated herein by reference. "Human" in reference to the disclosed antibody molecules specifically refers to antibody molecules having variable and/or constant regions derived from human germline immunoglobulin sequences, wherein said sequences may, but need not, be modified/altered to have certain amino acid substitutions or residues that are not encoded by human germline immunoglobulin sequence. Such mutations can be introduced by methods including, but not limited to, random or site-specific mutagenesis in vitro, or by somatic mutation in vivo. Specific examples of mutation techniques discussed in the literature are that disclosed in Gram et al., 1992 *PNAS USA* 89:3576-3580; Barbas et al., 1994 *PNAS USA* 91:3809-3813, and Schier et al., 1996 *J. Mol. Biol.* 263:551-567; the disclosures of which are incorporated herein by reference. These are only specific examples and do not represent the only available techniques. There are a plethora of mutation techniques in the scientific literature which are available to, and widely appreciated by, the skilled artisan. "Humanized" in reference to the disclosed antibody molecules refers specifically to antibody molecules wherein CDR sequences derived from another mammalian species, such as a mouse, are grafted onto human framework sequences. "Primatized" in reference to the disclosed antibody molecules refers to antibody molecules wherein CDR sequences of a non-primate are inserted into primate framework sequences, see, e.g., WO 93/02108 and WO 99/55369; the disclosures of which are incorporated herein by reference.

Specific antibodies of the present invention are monoclonal antibodies and, in particular embodiments, are in one of the following antibody formats: IgD, IgA, IgE, IgM, IgG 1, IgG2, IgG3, IgG4 or any derivative of any of the foregoing. The language "derivatives thereof" or "derivatives" in this respect includes, inter alia, (i) antibodies and antibody molecules with conservative modifications in one or both variable regions (i.e., VH and/or VL), (ii) antibodies and antibody molecules with manipulations in the constant regions of the heavy and/or light chains, and/or (iii) antibodies and antibody molecules that contain additional chemical moieties which are not normally a part of the immunoglobulin molecule (e.g., pegylation).

Manipulations of the variable regions can be within one or more of the VH and/or VL CDR regions. Site-directed mutagenesis, random mutagenesis or other method for generating sequence or molecule diversity can be utilized to create mutants which can subsequently be tested for a particular functional property of interest in available in vitro or in vivo assays including those described herein.

Antibodies of the present invention also include those in which modifications have been made to the framework residues within VH and/or VL to improve one or more properties of the antibody of interest. Typically, such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. Such "backmutated" antibodies are also intended to be encompassed by the invention. Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al; the disclosure of which is incorporated herein by reference.

In addition or alternative to modifications made within the framework or CDR regions, antibodies of the invention may be engineered to include modifications within the Fc or constant regions, where present, typically to alter one or more functional properties of the antibody, such as serum half-life, complement fixation, Fc receptor binding, and/or antigen-dependent cellular cytotoxicity.

The concept of generating "hybrids" or "combinatorial" IgG forms comprising various antibody isotypes to hone in on desired effector functionality has generally been described; see, e.g., Tao et al., 1991 *J. Exp. Med.* 173:1025-1028. A specific embodiment of the present invention encompasses antibody molecules that possess specific manipulations in the Fc region which have been found to result in reduced or altered binding to FcγR receptors, C1q or FcRn on the part of the antibody. The present invention, therefore, encompasses antibodies in accordance with the present description that do not provoke (or provoke to a lesser extent) antibody-dependent cellular cytotoxicity ("ADCC"), complement-mediated cytotoxicity ("CMC"), or form immune complexes, while retaining normal pharmacokinetic ("PK") properties. Specific embodiments of the present invention provide an antibody molecule as defined in accordance with the present invention which comprises, as part of its immunoglobulin structure, SEQ ID NO: 24 and, in particular embodiments, residues 107-326 of SEQ ID NO: 24 as part of the immunoglobulin structure. The present invention encompasses antibody molecules which comprise: (i) a light chain comprising SEQ ID NO: 1, and (ii) a heavy chain comprising SEQ ID NO: 11 in sequence with (adjacent to) or followed by a series of amino acids selected from the group consisting of: SEQ ID NO: 21 (IgG1), SEQ ID NO: 22 (IgG2), SEQ ID NO: 23 (IgG4) and SEQ ID NO: 24 (IgG2 m4). FIG. 6 illustrates a comparison of sequence comprising SEQ ID NO: 24, particularly IgG2 m4, with IgG1, IgG2, and IgG4. Amino acid sequences for mature, secreted anti-PCSK9 IgG2m4 heavy and light chains can be found as SEQ ID NOs: 25 and 26, respectively. Antibody molecules encoded at least in part by said sequence are encompassed herein.

Specific PCSK9-specific antagonists may carry a detectable label, or may be conjugated to a toxin (e.g., a cytotoxin), a radioactive isotope, a radionuclide, a liposome, a targeting moiety, a biosensor, a cationic tail, or an enzyme (e.g., via a peptidyl bond or linker). Such PCSK9-specific antagonist compositions form an additional aspect of the present invention.

In another aspect, the present invention provides isolated nucleic acid encoding disclosed PCSK9-specific antagonists. "Isolated" as mentioned prior refers to the property of the thing referred to that makes them different from that found in nature. The difference can be, for example, that they are of a different purity than that found in nature, or that they are of a different structure or form part of a different structure than that found in nature. An example of nucleic acid not found in nature is, for example, nucleic acid substantially free of other cellular material. The nucleic acid may be present in whole cells, in a cell lysate, or in a partially purified or substantially pure form. In specific instances, a nucleic acid may be isolated when purified away from other cellular components or other contaminants, e.g., other cellular nucleic acids or proteins, for example, using standard techniques, including without limitation, alkaline/SDS treatment, CsCl banding, column chromatography, agarose gel electrophoresis and other suitable methods known in the art. The nucleic acid may include DNA (inclusive of cDNA) and/or RNA. Nucleic acids of the present invention can be obtained using standard molecular biology techniques. For antibodies expressed by hybridomas (e.g., hybridomas prepared from transgenic mice carrying human immunoglobulin genes), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

The present invention encompasses isolated nucleic acid encoding disclosed variable heavy and/or light chains and select components thereof, particularly the disclosed variable or respective CDR regions and, in particular CDR3. In specific embodiments hereof, the CDR(s) are provided within antibody framework regions and, in particular embodiments, human framework regions. Specific embodiments provide isolated nucleic acid encoding the CDR(s) into germline framework regions including, but not limited to, human germline framework regions. Specific embodiments herein provide isolated nucleic acid encoding heavy chain CDR SEQ ID NO: 17 (in specific embodiments, said nucleic acid of which comprises SEQ ID NO: 18) into VH5_3 in place of the nucleic acid encoding the relevant CDR. Specific embodiments herein provide nucleic acid encoding heavy chain variable CDR1, CDR2 and/or CDR3 sequences SEQ ID NOs: 13, 15 and 17, respectively (and, in particular embodiments, said nucleic acid of which comprises SEQ ID NOs: 14, 16 and 18, respectively) into VH5_3 in place of the relevant CDRs. Specific embodiments herein provide isolated nucleic encoding light chain CDR SEQ ID NO: 7 (in specific embodiments, said nucleic acid of which comprises SEQ ID NO: 8) into VK4_3 in place of the nucleic acid encoding the relevant CDR. Specific embodiments herein provide nucleic acid encoding light chain variable CDR1, CDR2 and/or CDR3 sequences SEQ ID NOs: 3, 5 and 7, respectively (and, in particular embodiments, said nucleic acid of which comprises SEQ ID NOs: 4, 6 and 8, respectively) into VK4__3 in place of the relevant CDRs. Specific embodiments further provide heavy chain variable CDR3 SEQ ID NO: 17 (and, in particular embodiments, said nucleic acid of which comprises SEQ ID NO: 18) and light chain variable CDR3 SEQ ID NO: 7 (and, in particular embodiments, said nucleic acid of which comprises SEQ ID NO: 8) into VH5__3 and VK4__3 germline sequences, respectively. Further embodiments provide heavy chain variable CDR1, CDR2 and/or CDR3 sequences SEQ ID NOs: 13, 15 and 17, respectively (and, in particular embodiments, said nucleic acid of which comprises SEQ ID NOs: 14, 16 and 18, respectively) into VH5__3 in place of the relevant CDRs; and light chain variable CDR1, CDR2 and/or CDR3 sequences SEQ ID NOs: 3, 5 and 7, respectively (and, in particular embodiments, said nucleic acid of which comprises SEQ ID NOs: 4, 6 and 8, respectively) into VK4__3 in place of the relevant CDRs.

The isolated nucleic acid encoding the variable regions can be provided within any desired antibody molecule format including, but not limited to, the following: $F(ab')_2$, a Fab, a Fv, a scFv, bispecific antibody molecules (antibody molecules comprising a PCSK9-specific antibody or antigen binding fragment as disclosed herein linked to a second functional moiety having a different binding specificity than the antibody, including, without limitation, another peptide or protein such as an antibody, or receptor ligand), a bispecific single chain Fv dimer, a minibody, a dAb fragment, diabody, triabody or tetrabody, a minibody, IgG, IgG1, IgG2, IgG3, IgG4, IgM, IgD, IgA, IgE or any derivatives thereof.

Specific embodiments provide isolated nucleic acid which encodes PCSK9-specific antagonists and, in more specific embodiments, antibody molecules comprising a heavy chain variable domain which comprises SEQ ID NO: 11; specific embodiments of which comprise nucleic acid sequence SEQ ID NO: 12. Specific embodiments of the present invention provide isolated nucleic acid encoding PCSK9-specific antagonists and, in more specific embodiments, antibody molecules, which additionally comprise: (i) nucleic acid encoding heavy chain CDR1 amino acid sequence SEQ ID NO: 13 (specific embodiments of which comprise nucleic acid SEQ ID NO: 14) and/or (ii) nucleic acid encoding heavy chain CDR2 amino acid sequence SEQ ID NO: 15 (specific embodiments of which comprise nucleic acid SEQ ID NO: 16). Specific embodiments provide isolated nucleic acid encoding PCSK9-specific antagonists and, in more specific embodiments, antibody molecules comprising a light chain variable domain which comprises SEQ ID NO: 27; specific embodiments of which comprise nucleic acid sequence SEQ ID NO: 28. Specific embodiments of the present invention provide isolated nucleic acid encoding PCSK9-specific antagonists and, in more specific embodiments, antibody molecules, which additionally comprise: (i) nucleic acid encoding light chain CDR1 amino acid sequence SEQ ID NO: 3 (specific embodiments of which comprise nucleic acid SEQ ID NO: 4) and/or (ii) nucleic acid encoding light chain CDR2 amino acid sequence SEQ ID NO: 5 (specific embodiments of which comprise nucleic acid SEQ ID NO: 6). Specific embodiments provide isolated nucleic acid encoding PCSK9-specific antagonists and, in more specific embodiments, antibody molecules which comprise a heavy chain variable domain which comprises SEQ ID NO: 11; specific embodiments of which comprise nucleic acid sequence SEQ ID NO: 12; and a light chain variable domain which comprises SEQ ID NO: 27; specific embodiments of which comprise nucleic acid sequence SEQ ID NO: 28. Specific embodiments provide isolated nucleic acid encoding (i) heavy chain CDR1, CDR2 and/or CDR3 sequences (SEQ ID NOs: 13, 15 and 17, respectively; specific embodiments of which comprise nucleic acid SEQ ID NOs: 14, 16 and/or 18, respectively) preferably in a framework region (including but not limited to a human framework region); and (ii) light chain CDR1, CDR2 and/or CDR3 sequences (SEQ ID NO: 3, 5 and 7, respectively; specific embodiments of which comprise nucleic acid SEQ ID NOs: 4, 6 and/or 8, respectively) preferably in a framework region (including but not limited to a human framework region). The present invention further provides in specific embodiments, homologs of the antagonists disclosed above, characterized as being at least 90% identical over the heavy and/or light chain variable regions, or the CDR regions, as appropriate, whichever is present to the corresponding sequences of 1B20.

Additional embodiments provide isolated nucleic acid encoding PCSK9-specific antagonists and, in more specific embodiments, antibody molecules which comprise a light chain comprising SEQ ID NO: 1 (specific embodiments of which comprise nucleic acid SEQ ID NO: 2) and a heavy chain or Fd chain comprising amino acids 1-221 of SEQ ID NO: 9, or SEQ ID NO: 9 (specific embodiments of which comprise nucleic acid 1-663 of SEQ ID NO: 10, or SEQ ID NO: 10; respectively). Further embodiments provide isolated nucleic acid encoding PCSK9-specific antagonists and, in more specific embodiments, antibody molecules which comprise a light chain comprising SEQ ID NO: 26 (specific embodiments of which comprise SEQ ID NO: 30) and a heavy chain comprising SEQ ID NO: 25 (specific embodiments of which comprise SEQ ID NO: 29). The present invention further provides in specific embodiments, homologs of the antagonists disclosed above, characterized as being at least 90% identical over the heavy and/or light chains to the corresponding sequences of 1B20.

Specific embodiments of the present invention encompass nucleic acid encoding antibody molecules that possess manipulations in the Fc region which result in reduced or altered binding to FcγR receptors, C1 q or FcRn on the part of the antibody. One specific embodiment of the present invention is isolated nucleic acid which encodes for antibody molecules comprising as part of their immunoglobulin structure SEQ ID NO: 24 and, in particular embodiments, residues 107-326 of SEQ ID NO: 24. In specific embodiments, synthetic PCSK9-specific antagonists can be produced by expression from nucleic acid generated from oligonucleotides synthesized and assembled within suitable expression vectors; see, e.g., Knappick et al., 2000 *J. Mol. Biol.* 296:57-86, and Krebs et al., 2001 *J. Immunol. Methods* 254:67-84.

The present invention encompasses nucleic acid encoding antibody molecules which comprise: (i) nucleic acid encoding a light chain comprising SEQ ID NO: 1 (specific embodiments of which comprise nucleic acid SEQ ID NO: 2), and (ii) nucleic acid encoding a heavy chain comprising SEQ ID NO: 11 (specific embodiments of which comprise nucleic acid SEQ ID NO: 12) followed in sequence by (adjacent to) a set of nucleotides encoding for a set of amino acids selected from the group consisting of: SEQ ID NO: 21 (IgG1), SEQ ID NO: 22 (IgG2), SEQ ID NO: 23 (IgG4) and SEQ ID NO: 24 (IgG2 m4). Nucleotide sequences for mature, secreted anti-PCSK9 IgG2m4 heavy and light chains can be found as SEQ ID NOs: 29 and 30, respectively. Plasmid sequences comprising heavy and light chain 1B20 anti-PCSK9 IgG2m4 antibody molecules can be found as SEQ ID NOs: 35 and 36, respectively. Nucleic acid encoding such antibody molecules form important embodiments hereof.

Also included within the present invention are isolated nucleic acids comprising nucleotide sequences which are at least about 90% identical and more preferably at least about 95% identical to the full length of the nucleotide sequences described herein, and which nucleotide sequences encode PCSK9-specific antagonists which inhibit PCSK9-dependent inhibition of cellular LDL uptake by at least 10%.

Reference to "at least about 90% identical" throughout the application includes at least about 90, 91, 92, 93, 94, 95, 96, 97, 98, 99 or 100% identical.

The invention further provides isolated nucleic acid at least a portion of which hybridizes to the complement of nucleic acid consisting of SEQ ID NO: 12 and/or SEQ ID NO: 28 under stringent hybridization conditions, said nucleic acid of which confers upon antibody molecules the ability to specifically bind PCSK9 and antagonize PCSK9 function, and PCSK9-specific antagonists expressed employing said nucleic acid. Methods for hybridizing nucleic acids are well-known in the art; see, e.g., Ausubel, *Current Protocols in Molecular Biology*, John Wiley & Sons, N.Y., 6.3.1-6.3.6, 1989. Stringent hybridization conditions involve hybridizing at 68° C. in 5×SSC/5×Denhardt's solution (or equivalent)/1.0% SDS, and washing in 0.2×SSC/0.1% SDS at room temperature. Moderately stringent conditions include washing in 3×SSC at 42° C. The parameters of salt concentration and temperature can be varied to achieve the optimal level of identity between the probe and the target nucleic acid. The skilled artisan can manipulate various hybridization and/or washing conditions to specifically target nucleic acid in the hybridizing portion that is at least 80, 85, 90, 95, 98, or 99% identical to SEQ ID NO: 12 and/or SEQ ID NO: 28. Basic parameters affecting the choice of hybridization conditions and guidance for devising suitable conditions are set forth by Sambrook et al., Molecular Cloning. A Laboratory Manual, Cold Spring Harbor Laboratory Press, Cold Spring Harbor, N.Y., chapters 9 and 11, 1989 and Ausubel et al. (eds), *Current Protocols in Molecular Biology*, John Wiley & Sons, Inc., sections 2.10 and 6.3-6.4, 1995 (the disclosures of which are incorporated herein by reference), and can be readily determined by those having ordinary skill in the art. PCSK9 antagonists having one or more variable regions comprising nucleic acid which hybridizes to the complement of nucleic acid consisting of SEQ ID NO: 12 and/or SEQ ID NO: 28 under stringent hybridization conditions should be effective in antagonizing one or more functions of PCSK9. Said antagonists and encoding nucleic acid, thus, form important embodiments of the present invention.

In another aspect, the present invention provides vectors comprising the nucleic acid disclosed herein. Vectors in accordance with the present invention include, but are not limited to, plasmids and other expression constructs (e.g., phage or phagemid, as appropriate) suitable for the expression of the desired antibody molecule at the appropriate level for the intended purpose; see, e.g., Sambrook & Russell, *Molecular Cloning: A Laboratory Manual:* 3$^{rd}$ Edition, Cold Spring Harbor Laboratory Press; the disclosure of which is incorporated herein by reference. For most cloning purposes, DNA vectors may be used. Typical vectors include plasmids, modified viruses, bacteriophage, cosmids, yeast artificial chromosomes, bacterial artificial chromosomes, and other forms of episomal or integrated DNA. It is well within the purview of the skilled artisan to determine an appropriate vector for a particular gene transfer, generation of a recombinant PCSK9-specific antagonist, or other use. In specific embodiments, in addition to a recombinant gene, the vector may also contain an origin of replication for autonomous replication in a host cell, appropriate regulatory sequences, such as a promoter, a termination sequence, a polyadenylation sequence, an enhancer sequence, a selectable marker, a limited number of useful restriction enzyme sites, and/or other sequences as appropriate and the potential for high copy number. Examples of expression vectors for the production of protein-specific antagonists are well known in the art; see, e.g., Persic et al., 1997 *Gene* 187:9-18; Boel et al., 2000 *J. Immunol. Methods* 239:153-166, and Liang et al., 2001 *J. Immunol. Methods* 247:119-130; the disclosures of which are incorporated herein by reference. If desired, nucleic acid encoding the antagonist may be integrated into the host chromosome using techniques well known in the art; see, e.g., Ausubel, *Current Protocols in Molecular Biology*, John Wiley & Sons, 1999, and Marks et al., International Application Number WO 95/17516. Nucleic acid may also be expressed on plasmids maintained episomally or incorporated into an artificial chromosome; see, e.g., Csonka et al., 2000 *J. Cell Science* 113:3207-3216; Vanderbyl et al., 2002 *Molecular Therapy* 5:10. Specifically with regards to antibody molecules, the antibody light chain gene and the antibody heavy chain gene can be inserted into separate vectors or, more typically, both genes may be inserted into the same expression vector. Nucleic acid encoding any PCSK9-specific antagonist or component thereof can be inserted into an expression vector using standard methods (e.g., ligation of complementary restriction sites on the nucleic acid fragment and vector, or blunt end ligation if no restriction sites are present). Another specific example of how this may be carried out is through use of recombinational methods, e.g. the Clontech "InFusion" system, or Invitrogen "TOPO" system (both in vitro), or intracellularly (e.g. the Cre-Lox system). Specifically with regards to antibody molecules, the light and heavy chain variable regions can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector comprising nucleic acid encoding a PCSK9-specific antagonist can encode a signal peptide that facilitates secretion of the antagonist from a host cell. The nucleic acid can be cloned into the vector such that the nucleic acid encoding a signal peptide is linked in-frame adjacent to the PCSK9-specific antagonist-encoding nucleic acid. The signal peptide may be an immunoglobulin or a non-immunoglobulin signal peptide. Any technique available to the skilled artisan may be employed to introduce the nucleic acid into the host cell; see, e.g., Morrison, 1985 *Science,* 229:1202. Methods of subcloning nucleic acid molecules of interest into expression vectors, transforming or transfecting host cells containing the vectors, and methods of making substantially pure protein comprising the steps of introducing the respective expression vector into a host cell, and cultivating the host cell under appropriate conditions are well known. The PCSK9-specific antagonist so produced may be harvested from the host cells in conventional ways. Techniques suitable for the introduction of nucleic acid into cells of interest will depend on the type of cell being used. General techniques include, but are not limited to, calcium phosphate transfection, DEAE-Dextran, electroporation, liposome-mediated transfection and transduction using viruses appropriate to the cell line of interest (e.g., retrovirus, vaccinia, baculovirus, or bacteriophage).

In another aspect, the present invention provides isolated cell(s) comprising nucleic acid encoding disclosed PCSK9-specific antagonists. A variety of different cell lines are contemplated herein and can be used for the recombinant production of PCSK9-specific antagonists, including but not limited to those from prokaryotic organisms (e.g., *E. coli,*

*Bacillus*, and *Streptomyces*) and from eukaryotic (e.g., yeast, Baculovirus, and mammalian); see, e.g., Breitling et al., Recombinant antibodies, John Wiley & Sons, Inc. and Spektrum Akademischer Verlag, 1999; the disclosure of which is incorporated herein by reference. Plant cells, including transgenic plants, and animal cells, including transgenic animals (other than humans), comprising the nucleic acid or antagonists disclosed herein are also contemplated as part of the present invention. Suitable mammalian cells or cell lines including, but not limited to, those derived from Chinese Hamster Ovary (CHO cells, including but not limited to DHFR-CHO cells (described in Urlaub and Chasin, 1980 *Proc. Natl. Acad. Sci. USA* 77:4216-4220) used, for example, with a DHFR selectable marker (e.g., as described in Kaufman and Sharp, 1982 *Mol. Biol.* 159:601-621), NSO myeloma cells (where a GS expression system as described in WO 87/04462, WO 89/01036, and EP 338,841 may be used), COS cells, SP2 cells, HeLa cells, baby hamster kidney cells, YB2/0 rat myeloma cells, human embryonic kidney cells, human embryonic retina cells, and others comprising the nucleic acid or antagonists disclosed herein form additional embodiments of the present invention; the preceding cited disclosures of which are incorporated herein by reference. Specific embodiments of the present invention comprising nucleic acid encoding disclosed PCSK9-specific antagonists include, but are not limited to, *E. coli*; see, e.g., Pluckthun, 1991 *Bio/Technology* 9:545-551, or yeast, such as *Pichia*, and recombinant derivatives thereof (see, e.g., Li et al., 2006 *Nat. Biotechnol.* 24:210-215); the preceding disclosures of which are incorporated herein by reference. Specific embodiments of the present invention relate to eukaryotic cells comprising nucleic acid encoding the disclosed PCSK9-specific antagonists, see, Chadd & Chamow, 2001 *Current Opinion in Biotechnology* 12:188-194, Andersen & Krummen, 2002 *Current Opinion in Biotechnology* 13:117, Larrick & Thomas, 2001 *Current Opinion in Biotechnology* 12:411-418; the disclosures of which are incorporated herein by reference. Specific embodiments of the present invention relate to mammalian cells comprising nucleic acid encoding the disclosed PCSK9-specific antagonists which are able to produce PCSK9-specific antagonists with proper post translational modifications. Post translational modifications include, but are by no means limited to, disulfide bond formation and glycosylation. Another type of post translational modification is signal peptide cleavage. Preferred embodiments herein have the appropriate glycosylation; see, e., Yoo et al., 2002 *J. Immunol. Methods* 261:1-20; the disclosure of which is incorporated herein by reference. Naturally occurring antibodies contain at least one N-linked carbohydrate attached to a heavy chain. Id. Different types of mammalian host cells can be used to provide for efficient post-translational modifications. Examples of such host cells include Chinese Hamster Ovary (CHO), HeLa, C6, PC12, and myeloma cells; see, Yoo et al., 2002 *J. Immunol. Methods* 261: 1-20, and Persic et al., 1997 *Gene* 187:9-18; the disclosures of which are incorporated herein by reference.

In another aspect, the present invention provides isolated cell(s) comprising a polypeptide of the present invention.

In another aspect, the present invention provides a method of making a PCSK9-specific antagonist of the present invention, which comprises incubating a cell comprising nucleic acid encoding the PCSK9-specific antagonist, or a heavy and/or light chain or a fragment thereof (e.g., VH and/or VL, or one or more of the disclosed heavy and/or light chain variable region CDRs) of a desired PCSK9-specific antagonist (dictated by the desired antagonist) with specificity for human and/or murine PCSK9 under conditions that allow the expression of the PCSK9-specific antagonist, or the expression and assembly of said heavy and/or light chains or fragment into a PCSK9-specific antagonist, and isolating said PCSK9-specific antagonist from the cell. One example by which to generate particular desired heavy and/or light chain sequence or fragment is to first amplify (and modify) the germline heavy and/or light chain variable sequences or fragment using PCR. Germline sequence for human heavy and/or light variable regions are readily available to the skilled artisan, see, e.g., the "Vbase" human germline sequence database, and Kabat, E. A. et al., 1991 *Sequences of Proteins of Immunological Interest*, Fifth Edition, U.S. Department of Health and Human Services, NIH Publication No. 91-3242; Tomlinson, I. M. et al., 1992 "The Repertoire of Human Germline VH Sequences Reveals about Fifty Groups of VH Segments with Different Hypervariable Loops" *J. Mol. Biol.* 227:776-798; and Cox, J. P. L. et al., 1994 "A Directory of Human Germ-line Vκ Segments Reveals a Strong Bias in their Usage" *Eur. J. Immunol.* 24:827-836; the disclosures of which are incorporated herein by reference. Mutagenesis of germline sequences may be carried out using standard methods, e.g., PCR-mediated mutagenesis where the mutations are incorporated into PCR primers, or site-directed mutagenesis. If full-length antibodies are desired, sequence is available for the human heavy chain constant region genes; see, e.g., Kabat. E. A. et al., 1991 *Sequences of Proteins of Immunological Interest*, Fifth Edition, U.S. Department of Health and Human Services, NIH Publication No. 91-3242. Fragments containing these regions may be obtained, for example, by standard PCR amplification. Alternatively, the skilled artisan can avail him/herself of vectors already encoding heavy and/or light chain constant regions.

Available techniques exist to recombinantly produce other antibody molecules which retain the specificity of an original antibody. A specific example of this is where DNA encoding the immunoglobulin variable region or the CDRs is introduced into the constant regions, or constant regions and framework regions, or simply the framework regions, of another antibody molecule; see, e.g., EP-184,187, GB 2188638, and EP-239400; the disclosures of which are incorporated herein by reference. Cloning and expression of antibody molecules, including chimeric antibodies, are described in the literature; see, e.g., EP 0120694 and EP 0125023; the disclosures of which are incorporated herein by reference.

Antibody molecules in accordance with the present invention may, in one instance, be raised and then screened for characteristics identified herein using known techniques. Basic techniques for the preparation of monoclonal antibodies are described in the literature, see, e.g., Kohler and Milstein (1975, *Nature* 256:495-497); the disclosure of which is incorporated herein by reference. Fully human monoclonal antibodies can be produced by available methods. These methods include, but are by no means limited to, the use of genetically engineered mouse strains which possess an immune system whereby the mouse antibody genes have been inactivated and in turn replaced with a repertoire of functional human antibody genes, while leaving other components of the mouse immune system unchanged. Such genetically engineered mice allow for the natural in vivo immune response and affinity maturation process which results in high affinity, full human monoclonal antibodies. This technology is well known in the art and is fully detailed in various publications, including but not limited to U.S. Pat. Nos. 5,545,806; 5,569,825; 5,625,126; 5,633,425; 5,789,650; 5,877,397; 5,661,016; 5,814,318; 5,874,299; 5,770,249 (assigned to GenPharm International and available through Medarex, under the umbrella of the "UltraMab Human Antibody Development System"); as well as U.S. Pat. Nos. 5,939,598; 6,075,181; 6,114,598; 6,150,584 and related family members (assigned to Abgenix, disclosing their XenoMouse® technology); the disclosures of which are incorporated herein by reference. See also reviews from Kellerman and Green, 2002 *Curr. Opinion in Biotechnology* 13:593-597, and Kontermann & Stefan, 2001 *Antibody Engineering*, Springer Laboratory Manuals; the disclosures of which are incorporated herein by reference.

Alternatively, a library of PCSK9-specific antagonists in accordance with the present invention may be brought into contact with PCSK9, and ones able to demonstrate specific binding selected. Functional studies can then be carried out to ensure proper functionality, e.g., inhibition of PCSK9-dependent inhibition of cellular LDL uptake. There are various techniques available to the skilled artisan for the selection of protein-specific molecules from libraries using enrichment technologies including, but not limited to, phage display (e.g., see technology from Cambridge Antibody Technology ("CAT") disclosed in U.S. Pat. Nos. 5,565,332; 5,733,743; 5,871,907; 5,872,215; 5,885,793; 5,962,255; 6,140,471; 6,225,447; 6,291,650; 6,492,160; 6,521,404; 6,544,731; 6,555,313; 6,582,915; 6,593,081, as well as other U.S. family members and/or applications which rely on priority filing GB 9206318, filed May 24, 1992; see also Vaughn et al., 1996, *Nature Biotechnology* 14:309-314), ribosome display (see, e.g., Hanes and Pluckthün, 1997 *Proc. Natl. Acad. Sci.* 94:4937-4942), bacterial display (see, e.g., Georgiou, et al., 1997 *Nature Biotechnology* 15:29-34) and/or yeast display (see, e.g., Kieke, et al., 1997 *Protein Engineering* 10:1303-1310); the preceding disclosures of which are incorporated herein by reference. A library, for example, can be displayed on the surface of bacteriophage particles, with nucleic acid encoding the PCSK9-specific antagonist or fragment thereof expressed and displayed on its surface. Nucleic acid may then be isolated from bacteriophage particles exhibiting the desired level of activity and the nucleic acid used in the development of desired antagonist. Phage display has been thoroughly described in the literature; see, e.g., Kontermann & Stefan, supra, and International Application Number WO 92/01047; the disclosures of which are incorporated herein by reference. Specifically with regard to antibody molecules, individual heavy or light chain clones in accordance with the present invention may also be used to screen for complementary heavy or light chains, respectively, capable of interaction therewith to form a molecule of the combined heavy and light chains; see, e.g., International Application Number WO 92/01047. Any method of panning which is available to the skilled artisan may be used to identify PCSK9-specific antagonists. Another specific method for accomplishing this is to pan against the target antigen in solution, e.g. biotinylated, soluble PCSK9, and then capture the PCSK9-specific antagonist-phage complexes on streptavidin-coated magnetic beads, which are then washed to remove nonspecifically-bound phage. The captured phage can then be recovered from the beads in the same way they would be recovered from the surface of a plate, (e.g. DTT) as described herein.

PCSK9-specific antagonists may be purified by techniques available to one of skill in the art. Titers of the relevant antagonist preparation, ascites, hybridoma culture fluids, or relevant sample may be determined by various serological or immunological assays which include, but are not limited to, precipitation, passive agglutination, enzyme-linked immunosorbent antibody ("ELISA") techniques and radioimmunoassay ("RIA") techniques.

The present invention relates in part to methods employing PCSK9-specific antagonists described herein for antagonizing PCSK9 function; said methods of which are further described below. Use of the term "antagonizing" throughout the present application refers to the act of opposing, inhibiting, counteracting, neutralizing or curtailing one or more functions of PCSK9. Inhibition or antagonism of one or more of PCSK9-associated functional properties can be readily determined according to methodologies known to the art (see, e.g., Barak & Webb, 1981 *J. Cell Biol.* 90:595-604; Stephan & Yurachek, 1993 *J Lipid Res.* 34:325330; and McNamara et al., 2006 *Clinica Chimica Acta* 369:158-167) as well as those described herein. Inhibition or antagonism will effectuate a decrease in PCSK9 activity relative to that seen in the absence of the antagonist or, for example, that seen when a control antagonist of irrelevant specificity is present. Preferably, a PCSK9-specific antagonist in accordance with the present invention antagonizes PCSK9 functioning to the point that there is a decrease of at least 10%, of the measured parameter including but not limited to the activities disclosed herein, and more preferably, a decrease of at least 20%, 30%, 40%, 50%, 60%, 70%, 80%, 90% and 95% of the measured parameter. Such inhibition/antagonism of PCSK9 functioning is particularly effective in those instances where PCSK9 functioning is contributing at least in part to a particular phenotype, disease, disorder or condition which is negatively impacting the subject.

In one aspect, the present invention provides a method for antagonizing the activity of PCSK9, which comprises contacting a cell, population of cells or tissue sample capable of being affected by PCSK9 (i.e., which expresses and/or comprises LDL receptors) with a PCSK9-specific antagonist disclosed herein under conditions that allow said antagonist to bind to PCSK9 when present and inhibit PCSK9's inhibition of cellular LDL uptake. Specific embodiments of the present invention include such methods wherein the cell is a human cell. Additional embodiments of the present invention include such methods wherein the cell is a murine cell.

In another aspect, the present invention provides a method for antagonizing the activity of PCSK9 in a subject, which comprises administering to the subject a therapeutically effective amount of a PCSK9-specific antagonist of the present invention. In specific embodiments, the methods for antagonizing PCSK9 function are for the treatment of a PCSK9-associated disease, disorder or condition or, alternatively, a disease, disorder or condition that could benefit from the effects of a PCSK9 antagonist. The medicament would be useful in a subject(s) exhibiting a condition associated with PCSK9 activity, or a condition where the functioning of PCSK9 is contraindicated for a particular subject. In select embodiments, the condition may be hypercholesterolemia, coronary heart disease, metabolic syndrome, acute coronary syndrome or related conditions.

The present invention, thus, contemplates the use of PCSK9-specific antagonists described herein in various methods of treatment where antagonizing PCSK9 function is desirable. The method of treatment can be prophylactic or therapeutic in nature. In specific embodiments, the present invention relates to a method of treatment for a condition associated with/attributed to PCSK9 activity, or a condition where the functioning of PCSK9 is contraindicated for a particular subject, which comprises administering to the subject a therapeutically effective amount of a PCSK9-specific antagonist of the present invention. In select embodiments, the condition may be hypercholesterolemia, coronary heart disease, metabolic syndrome, acute coronary syndrome or related conditions.

Methods of treatment in accordance with the present invention comprise administering to an individual a therapeutically (or prophylactically) effective amount of a PCSK9-specific antagonist of the present invention. Use of the terms "therapeutically effective" or "prophylactically effective" in reference to an amount refers to the amount necessary at the intended dosage to achieve the desired therapeutic/prophylactic effect for the period of time desired. The desired effect may be, for example, amelioration of at least one symptom associated with the treated condition. These amounts will vary, as the skilled artisan will appreciate, according to various factors, including but not limited to the disease state, age, sex and weight of the individual, and the ability of the PCSK9-specific antagonist to elicit the desired effect in the individual. The response may be documented by in vitro assay, in vivo non-human animal studies, and/or further supported from clinical trials.

The PCSK9-specific antagonist may be administered as a pharmaceutical composition. The present invention, thus, provides a pharmaceutically acceptable composition comprising a PCSK9-specific antagonist of the invention and a pharmaceutically acceptable carrier including but not limited to an excipient, diluent, stabilizer, buffer, or alternative designed to facilitate administration of the antagonist in the desired format and amount to the treated individual.

The pharmaceutical composition may be formulated by any number of strategies known in the art, see, e.g., McGoff and Scher, 2000 *Solution Formulation of Proteins/Peptides*: In—McNally, E. J., ed. Protein Formulation and Delivery. New York, N.Y.: Marcel Dekker; pp. 139-158; Akers & Defilippis, 2000, *Peptides and Proteins as Parenteral Solutions*. In—Pharmaceutical Formulation Development of Peptides and Proteins. Philadelphia, Pa.: Taylor and Francis; pp. 145-177; Akers et al., 2002, *Pharm. Biotechnol.* 14:47-127. A pharmaceutically acceptable composition suitable for patient administration will contain an effective amount of the PCSK9-specific antagonist in a formulation which both retains biological activity while also promoting maximal stability during storage within an acceptable temperature range.

The antagonist-based pharmaceutically acceptable composition may, in particular embodiments, be in liquid or solid form, or in the form of gas particles or aerosolized particles. Any technique for production of liquid or solid formulations may be utilized. Such techniques are well within the realm of the abilities of the skilled artisan. Solid formulations may be produced by any available method including, but not limited to, lyophilization, spray drying, or drying by supercritical fluid technology. Solid formulations for oral administration may be in any form rendering the antagonist accessible to the patient in the prescribed amount and within the prescribed period of time. The oral formulation can take the form of a number of solid formulations including, but not limited to, a tablet, capsule, or powder. Solid formulations may alternatively be lyophilized and brought into solution prior to administration for either single or multiple dosing according to methods well known to the skilled artisan. Antagonist compositions should generally be formulated within a biologically relevant pH range and may be buffered to maintain a proper pH range during storage. Both liquid and solid formulations generally require storage at lower temperatures (e.g., 2-8° C.) in order to retain stability for longer periods. Formulated antagonist compositions, especially liquid formulations, may contain a bacteriostat to prevent or minimize proteolysis during storage, including but not limited to effective concentrations (e.g., ≦1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component. Additional components may be added to either a buffered liquid or solid antagonist formulation, including but not limited to sugars as a cryoprotectant (including but not limited to polyhydroxy hydrocarbons such as sorbitol, mannitol, glycerol, and dulcitol and/or disaccharides such as sucrose, lactose, maltose, or trehalose) and, in some instances, a relevant salt (including but not limited to NaCl, KCl, or LiCl). Such antagonist formulations, especially liquid formulations slated for long term storage, will rely on a useful range of total osmolarity to both promote long term stability at temperatures of, for example, 2-8° C. or higher, while also making the formulation useful for parenteral injection. As appropriate, preservatives, stabilizers, buffers, antioxidants and/or other additives may be included. The formulations may contain a divalent cation (including but not limited to MgCl2, CaCl2, and MnCl2); and/or a non-ionic surfactant (including but not limited to Polysorbate-80 (Tween 80™), Polysorbate-60 (Tween 60™), Polysorbate-40 (Tween 40™), and Polysorbate-20 (Tween 20™), polyoxyethylene alkyl ethers, including but not limited to Brij 58™, Brij35™, as well as others such as Triton X-100™, Triton X-114™, NP40™, Span 85 and the Pluronic series of non-ionic surfactants (e.g., Pluronic 121)). Any combination of such components form specific embodiments of the present invention.

Pharmaceutical compositions in liquid format may include a liquid carrier, e.g., water, petroleum, animal oil, vegetable oil, mineral oil, or synthetic oil. The liquid format may also include physiological saline solution, dextrose or other saccharide solution or glycols, such as ethylene glycol, propylene glycol or polyethylene glycol.

Preferably, the pharmaceutical composition may be in the form of a parenterally acceptable aqueous solution that is pyrogen-free with suitable pH, tonicity, and stability. Pharmaceutical compositions may be formulated for administration after dilution in isotonic vehicles, for example, Sodium Chloride Injection, Ringer's Injection, or Lactated Ringer's Injection.

One aspect of the present invention is a pharmaceutical composition which comprises: (i) about 50 to about 200 mg/mL of protein including but not limited to the PCSK9-specific antagonists described herein; (ii) a polyhydroxy hydrocarbon (including but not limited to sorbitol, mannitol, glycerol and dulcitol) and/or a disaccharide (including but not limited to sucrose, lactose, maltose and trehalose); the total of said polyhydroxy hydrocarbon and/or disaccharide being about 1% to about 6% weight per volume ("w/v") of the formulation; (iii) about 5 mM to about 200 mM of histidine, imidazole, phosphate or acetic acid which serves as a buffering agent to prevent pH drift over the shelf life of the pharmaceutical composition and as a tonicity modifier; (iv) about 5 mM to about 200 mM of arginine, proline, phenylalanine, alanine, glycine, lysine, glutamic acid, aspartic acid or methionine to counteract aggregation; (v) about 0.01 M to about 0.1 M of hydrochloric acid ("HCl") in an amount sufficient to achieve a pH in the range of about 5.5 to about 7.5; and (vi) a liquid carrier including but not limited to sterile water, petroleum, animal oil, vegetable oil, mineral oil, synthetic oil, physiological saline solution, dextrose or other saccharide solution or glycols, such as ethylene glycol, propylene glycol or polyethylene glycol; wherein said pharmaceutical composition has a pH in the range of about 5.5 to about 7.5; and wherein said pharmaceutical composition optionally comprises about 0.01% to about 1% w/v of the formulation of a non-ionic surfactant (including but not limited to Polysorbate-80 (Tween 80™), Polysorbate-60 (Tween 60™), Polysorbate-40 (Tween 40™), and Polysorbate-20 (Tween 20™), polyoxyethylene alkyl ethers, including but not limited to Brij 58™, Brij35™, as well as others such as Triton X-100™, Triton X-114™, NP40™, Span 85 and the Pluronic series of non-ionic surfactants (e.g., Pluronic 121)).

HCl may be added as free acid, Histidine-HCl or Arginine-HCl. Where supplied as Histidine-HCl or Arginine-HCl, the total amounts of Histidine or Arginine in the HCl form should be that specified above. Accordingly, some or all of the HCl depending on the amounts of Histidine and/or Arginine may be supplied as Histidine-HCl and/or Arginine-HCl; as appropriate. Use of the term "about" with respect to amounts disclosed in the specification means within 10% of the specified numbers provided. A range provided as, for example" in "about 50 to about 200" expressly includes as distinct embodiments each number within said range. As such in the above example, embodiments including but not limited to those having 50, 100, 125, 150 and 200 form specific embodiments herein. Pharmaceutical compositions as disclosed herein have general applicability despite the mode of administration. In specific embodiments, the disclosed pharmaceutical compositions are useful for subcutaneous administration as a liquid or upon reconstitution of a lyophilized form. Proteins that can be employed in the disclosed formulations include any polymeric protein or polypeptide characterized as comprising covalently linked amino acid residues delivered for purposes of effecting a therapeutic benefit. Proteins of use in the present compositions include but are not limited to any antibody molecules as defined herein or any non-antibody or non-immunoglobulin proteins, peptides, pegylated proteins and fusion proteins.

Specific aspects of the present invention relate to the above disclosed pharmaceutical compositions which comprise: (i) about 50 to about 200 mg/mL of protein including but not limited to the PCSK9-specific antagonists described herein; (ii) about 1% to about 6% (in particular embodiments from about 2% to about 6%) w/v mannitol, trehalose or sucrose; (iii) about 10 mM to about 100 mM of histidine; (iv) about 25 mM to about 100 mM of arginine or proline; (v) about 0.02 M to about 0.05M of hydrochloric acid ("HCl") in an amount sufficient to achieve a pH in the range of about 5.8 to about 7; and (vi) a liquid carrier including but not limited to sterile water, petroleum, animal oil, vegetable oil, mineral oil, synthetic oil, physiological saline solution, dextrose or other saccharide solution or glycols, such as ethylene glycol, propylene glycol or polyethylene glycol; wherein said pharmaceutical composition has a pH in the range of about 5.8 to about 7; and wherein said pharmaceutical composition optionally comprising about 0.01% to about 1% w/v of the formulation of a non-ionic surfactant (including but not limited to Polysorbate-80 (Tween 80™), Polysorbate-60 (Tween 60™), Polysorbate-40 (Tween 40™), and Polysorbate-20 (Tween 20™), polyoxyethylene alkyl ethers, including but not limited to Brij 58™, Brij35™, as well as others such as Triton X-100™, Triton X-114™, NP40™, Span 85 and the Pluronic series of non-ionic surfactants (e.g., Pluronic 121)).

Specific embodiments provide pharmaceutical compositions which comprise: (i) 50 to 200 mg/mL of protein including but not limited to the PCSK9-specific antagonists described herein; (ii) about 1% to about 6% (in particular embodiments from about 2% to about 6%) w/v mannitol, trehalose or sucrose; (iii) about 10 mM to about 150 mM of histidine; (iv) about 10 mM to about 150 mM of arginine or proline; (v) about 0.03 M to about 0.05 M of hydrochloric acid ("HCl") in an amount sufficient to achieve a pH in the range of about 5.8 to about 6.5; and (vi) a liquid carrier including but not limited to sterile water, petroleum, animal oil, vegetable oil, mineral oil, synthetic oil, physiological saline solution, dextrose or other saccharide solution or glycols, such as ethylene glycol, propylene glycol or polyethylene glycol; wherein said pharmaceutical composition has a pH in the range of about 5.8 to about 6.5; and wherein said pharmaceutical composition optionally comprising about 0.01% to about 1% w/v of Polysorbate-80 (Tween 80™) or Polysorbate-20 (Tween 20™).

Specific embodiments herein provide pharmaceutical compositions which comprise: (i) 50 to 200 mg/mL of protein including but not limited to the PCSK9-specific antagonists described herein; (ii) about 1% to about 6% (in particular embodiments from about 2% to about 6%) w/v sucrose; (iii) about 25 mM to about 100 mM of histidine; (iv) about 25 mM to about 100 mM of arginine; (v) about 0.040 M to about 0.045 M of hydrochloric acid ("HCl") in an amount sufficient to achieve a pH of about 6; and (vi) sterile water; wherein said pharmaceutical composition has a pH of about 6; and wherein said pharmaceutical composition optionally comprising about 0.01% to about 1% w/v of Polysorbate-80 (Tween 80™) or Polysorbate-20 (Tween 20™). In specific embodiments thereof, the levels of histidine and arginine are within 25 mM of each other and, in other embodiments are the same.

Specific embodiments herein provide pharmaceutical compositions which comprise (i) 50 to 200 mg/mL of protein including but not limited to the PCSK9-specific antagonists described herein; (ii) sucrose, histidine and arginine in one of the following amounts: (a) about 1% w/v sucrose, about 10 mM histidine and about 25 mM arginine; (b) about 2% w/v sucrose, about 25 mM histidine and about 25 mM arginine; (c) about 3% w/v sucrose, about 50 mM histidine and about 50 mM arginine; or (d) about 6% w/v sucrose, about 100 mM histidine and about 100 mM arginine; (iii) about 0.04 mol or, alternatively, about 1.46 g of HCl; and (iv) sterile water; wherein said pharmaceutical composition has a pH of about 6; and wherein said pharmaceutical composition optionally comprising about 0.01% to about 1% w/v of Polysorbate-80 (Tween 80™) or Polysorbate-20 (Tween 20™). Specific embodiments herein are wherein the amounts of sucrose, histidine and arginine in (ii) above are that described in (c) or (d). Specific embodiments employing pharmaceutical formulations as described above wherein the amounts of sucrose, histidine and arginine are that specified in (ii) (c) were found to provide an osmolality similar to the physiological value of 300 mOsm and provided stability in both the liquid and lyophilized form.

Specific embodiments herein provide pharmaceutical compositions as described which comprise 50 to 200 mg/ml of any one of the various PCSK9-specific antagonists described herein. For purposes of exemplification of one distinct embodiment thereof, and not to be construed as a limitation, is the following: a pharmaceutical formulation as described above which comprises: a PCSK9-specific antagonist which comprises: (a) a light chain comprising SEQ ID NO: 26; and (b) a heavy chain comprising SEQ ID NO: 25; wherein said PCSK9-specific antagonist is an antibody molecule that antagonizes PCSK9's inhibition of cellular LDL uptake.

Particular embodiments herein are pharmaceutical compositions according to the above description which are lyophilized and reconstituted. In specific embodiments, said protein concentration in said lyophilized and reconstituted solution is up to 2-fold higher than in the pre-lyophilized composition. In specific embodiments, the protein or PCSK9-specific antagonist concentration in the lyophilized and/or reconstituted pharmaceutical composition is in the range of about 50 mg/mL to about 300 mg/mL. Diluents useful for reconstituting the lyophilized pharmaceutical compositions include but are not limited to sterile water, bacteriostatic water for injection ("BWFI"), phosphate-buffered saline, a sterile saline solution, physiological saline solution, Ringer's solution or dextrose solution and may in specific embodiments contain 0.01-1% (w/v) of Polysorbate-80 (Tween 80™) or Polysorbate-20 (Tween 20™). In specific embodiments, lyophilized powder can be reconstituted with 1/60.2× original volume (or 0.167 mL) up to 1× (1 mL).

Exemplary embodiments of the present invention are pharmaceutical compositions as described herein which are stable. Other embodiments of the present invention are pharmaceutical compositions as described herein which are stable to lyophilization and reconstitution. Various methods are available to the skilled artisan to prepare lyophilized compositions; see, e.g., Martin & Mo, 2007 "Stability Considerations for Lyophilized Biologics" Amer. Pharm. Rev. "Stable" as used herein refers to the property of the protein or PCSK9-specific antagonist to retain its physical or chemical stability, conformational integrity, or its ability to exhibit less denaturation, protein clipping, aggregation, fragmentation, acidic variant formation or loss of biological activity compared with a control sample at a temperature in the range of 4-37° C. for at least about 30 days. Other embodiments remain stable for up to 3 months, 6 months, 12 months, 2 years or longer periods at the above temperatures. In specific embodiments the formulation exhibits no significant changes at 2-8° C. for at least 6 months, and preferably 12 months, 2 years or longer, in order of preference. Specific embodiments experience less than 10% or, in particular embodiments, less than 5% of denaturation, protein clipping, aggregation, fragmentation, acidic variant formation or loss of biological activity compared with a control sample at a temperature in the range of 25-45° C. (or alternatively 2-8° C.) for at least about 30 days, 3 months, 6 months, 12 months, 2 years or longer. Stability of the formulations can be tested via several means known to the skilled artisan including, but not limited to Size Exclusion Chromatography (SEC-HPLC) to measure aggregation and fragmentation, Dynamic Light Scattering (DLS) to measure particle size of concentrated samples, capillary SDS-PAGE to measure fragmentation and capillary iso-electric focusing (cIEF) or cation exchange chromatography ("CEX") to measure acidic variants formation. Techniques suitable for the analysis of protein stability are well understood by those of skill in the art: see review in Peptide and Protein Drug Delivery, 247-301, Vincent Lee Ed., Marcel Dekker, Inc., New York, N.Y., Pubs. (1991) and Jones, 1993 *Adv. Drug Delivery Rev.* 10:29-90.

Pharmaceutical compositions as described herein should be sterile. There are various techniques available to the skilled artisan to accomplish this including, but not limited to, filtration through sterile filtration membranes. In specific embodiments, employing lyophilized and reconstituted compositions, this may be done prior to or following lyophilization and reconstitution.

Dosing of antagonist therapeutics is well within the realm of the skilled artisan, see, e.g., Lederman et al., 1991 *Int. J. Cancer* 47:659-664; Bagshawe et al., 1991 *Antibody, Immunoconjugates and Radiopharmaceuticals* 4:915-922, and will vary based on a number of factors including but not limited to the particular PCSK9-specific antagonist utilized, the patient being treated, the condition of the patient, the area being treated, the route of administration, and the treatment desired. A physician or veterinarian of ordinary skill can readily determine and prescribe the effective therapeutic amount of the antagonist. Dosage ranges may be from about 0.01 to 100 mg/kg, and more usually 0.05 to 25 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. For purposes of illustration, and not limitation, in specific embodiments, a dose of 5 mg to 2.0 g may be utilized to deliver the antagonist systemically. In specific embodiments, the concentration of the dose provided will be in the range of about 8 mg/mL to about 200 mg/mL. In other embodiments, a dose contemplated for use in the present invention is from about 50 mg/mL to about 150 mg/mL. In specific embodiments, the dose will be from about 0.1 mL to about 1.5 mL and in specific embodiments is 1 mL. Optimal precision in achieving concentrations of antagonist within a range that yields efficacy without toxicity requires a regimen based on the kinetics of the drug's availability to the target site(s). This involves a consideration of the distribution, equilibrium, and elimination of the PCSK9-specific antagonist. Antagonists described herein may be used alone at appropriate dosages. Alternatively, co-administration or sequential administration of other agents may be desirable. It will be possible to present a therapeutic dosing regime for the PCSK9-specific antagonists of the present invention in conjunction with alternative treatment regimes. For example, PCSK9-specific antagonists may be used in combination or in conjunction with other drugs (therapeutic and/or prophylactic), including but not limited to cholesterol-lowering drugs, for example, cholesterol absorption inhibitors (e.g., Zetia®) and cholesterol synthesis inhibitors (e.g., Zocor® and Vytorin®). The present invention contemplates such combinations and they form an important embodiment hereof. Accordingly, the present invention relates to methods of treatment as described above where the PCSK9-specific antagonist is administered/delivered simultaneously with, following or prior to another drug or drugs (therapeutic and/or prophylactic), including but not limited to cholesterol-lowering drugs, cholesterol absorption inhibitors and cholesterol absorption inhibitors.

Individuals (subjects) capable of treatment as described herein include primates, human and non-human, and include any non-human mammal or vertebrate of commercial or domestic veterinary importance.

The PCSK9-specific antagonist may be administered to an individual by any route of administration appreciated in the art, including but not limited to oral administration, administration by injection (specific embodiments of which include intravenous, subcutaneous, intraperitoneal or intramuscular injection), or administration by inhalation, intranasal, or topical administration, either alone or in combination with other agents designed to assist in the treatment of the individual. The PCSK9-specific antagonist may also be administered by injection devices, injector pens, needleless devices; and subcutaneous patch delivery systems. The route of administration should be determined based on a number of considerations appreciated by the skilled artisan including, but not limited to, the desired physiochemical characteristics of the treatment. Treatment may be provided on a daily, weekly, biweekly, or monthly basis, or any other regimen that delivers the appropriate amount of PCSK9-specific antagonist to the individual at the prescribed times such that the desired treatment is effected and maintained. The formulations may be administered in a single dose or in more than one dose at separate times.

Also contemplated are methods of using the disclosed antagonists in the manufacture of a medicament for treatment of a PCSK9-associated disease, disorder or condition or, alternatively, a disease, disorder or condition that could benefit from the effects of a PCSK9 antagonist. The medicament would be useful in a subject(s) exhibiting a condition associated with PCSK9 activity, or a condition where the functioning of PCSK9 is contraindicated fr a particular subject. In select embodiments, the condition may be hypercholesterolemia, coronary heart disease, metabolic syndrome, acute coronary syndrome or related conditions.

PCSK9-specific antagonists disclosed herein may also be used as a method of diagnosis of PCSK9. In select embodiments, the present invention encompasses methods of identifying or quantifying the level of PCSK9 present in a sample (including but not limited to a biological sample, e.g., serum or blood) which comprises contacting the sample with a PCSK9-specific antagonist described herein and detecting or quantifying, respectively, binding to PCSK9. The PCSK9-specific antagonist may be used in various assay formats known to the skilled artisan and may form part of a kit (the general features of a kit of which are further described below).

The present invention further provides for the administration of disclosed anti-PCSK9 antagonists for purposes of gene therapy. Through such methods, cells of a subject are transformed with nucleic acid encoding a PCSK9-specific antagonist of the invention. Subjects comprising the nucleic acids then produce the PCSK9-specific antagonists endogenously. Previously, Alvarez, et al, *Clinical Cancer Research* 6:3081-3087, 2000, introduced single-chain anti-ErbB2 antibodies to subjects using a gene therapy approach. The methods disclosed by Alvarez, et al, supra, may be easily adapted for the introduction of nucleic acids encoding an anti-PCSK9 antibody of the invention to a subject.

Nucleic acids encoding any PCSK9-specific antagonist may be introduced to a subject.

The nucleic acids may be introduced to the cells of a subject by any means known in the art. In preferred embodiments, the nucleic acids are introduced as part of a viral vector. Examples of preferred viruses from which the vectors may be derived include lentiviruses, herpes viruses, adenoviruses, adeno-associated viruses, vaccinia virus, baculovirus, alphavirus, influenza virus, and other recombinant viruses with desirable cellular tropism.

Various companies produce viral vectors commercially, including, but by no means limited to, Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Methods for constructing and using viral vectors are known in the art (see, e.g., Miller, et al, *BioTechniques* 7:980-990, 1992). Preferably, the viral vectors are replication defective, that is, they are unable to replicate autonomously, and thus are not infectious, in the target cell. Preferably, the replication defective virus is a minimal virus, i.e., it retains only the sequences of its genome which are necessary for encapsidating the genome to produce viral particles. Defective viruses, which entirely or almost entirely lack viral genes, are preferred. Use of defective viral vectors allows for administration to cells in a specific, localized area, without concern that the vector can infect other cells. Thus, a specific tissue can be specifically targeted.

Examples of vectors comprising attenuated or defective DNA virus sequences include, but are not limited to, a defective herpes virus vector (Kanno et al, *Cancer Gen. Ther.* 6:147-154, 1999; Kaplitt et al, *J. Neurosci. Meth.* 71:125-132, 1997 and Kaplitt et al, *J. Neuro Onc.* 19:137-147, 1994).

Adenoviruses are eukaryotic DNA viruses that can be modified to efficiently deliver a nucleic acid of the invention to a variety of cell types. Attenuated adenovirus vectors, such as the vector described by Strafford-Perricaudet et al, *J. Clin. Invest.* 90:626-630, 1992 are desirable in some instances. Various replication defective adenovirus and minimum adenovirus vectors have been described (PCT Publication Nos. WO94/26914, WO94/28938, WO94/28152, WO94/12649, WO95/02697 and WO96/22378). The replication defective recombinant adenoviruses according to the invention can be prepared by any technique known to a person skilled in the art (Levrero et al, *Gene* 101:195, 1991; EP 185573; Graham, *EMBO J.* 3:2917, 1984; Graham et al, *J. Gen. Virol.* 36:59, 1977).

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The use of vectors derived from the AAVs for transferring genes in vitro and in vivo has been described (see Daly, et al, *Gene Ther.* 8:1343-1346, 2001, Larson et al, *Adv. Exp. Med. Bio.* 489:45-57, 2001; PCT Publication Nos. WO 91/18088 and WO 93/09239; U.S. Pat. Nos. 4,797,368 and 5,139,941 and EP 488528B1).

In another embodiment, the gene can be introduced in a retroviral vector, e.g., as described in U.S. Pat. Nos. 5,399,346, 4,650,764, 4,980,289, and 5,124,263; Mann et al, *Cell* 33:153, 1983; Markowitz et al, *J. Virol.,* 62:1120, 1988; EP 453242 and EP 178220. The retroviruses are integrating viruses which infect dividing cells.

Lentiviral vectors can be used as agents for the direct delivery and sustained expression of nucleic acids encoding a PCSK9-specific antagonist of the invention in several tissue types, including brain, retina, muscle, liver and blood. The vectors can efficiently transduce dividing and nondividing cells in these tissues, and maintain long-term expression of the PCSK9-specific antagonist. For a review, see Zufferey et al, *J. Virol.* 72:9873-80, 1998 and Kafri et al, *Curr. Opin. Mol. Ther.* 3:316-326, 2001. Lentiviral packaging cell lines are available and known generally in the art. They facilitate the production of high-titer lentivirus vectors for gene therapy. An example is a tetracycline-inducible VSV-G pseudotyped lentivirus packaging cell line which can generate virus particles at titers greater than $10^6$ IU/ml for at least 3 to 4 days; see Kafri et al, *J. Virol.* 73:576-584, 1999. The vector produced by the inducible cell line can be concentrated as needed for efficiently transducing nondividing cells in vitro and in vivo.

Sindbis virus is a member of the alphavirus genus and has been studied extensively since its discovery in various parts of the world beginning in 1953. Gene transduction based on alphavirus, particularly Sindbis virus, has been well-studied in vitro (see Straus et al, *Microbiol. Rev.,* 58:491-562, 1994; Bredenbeek et al, *J. Virol.,* 67:6439-6446, 1993; Ijima et al, *Int. J. Cancer* 80:110-118, 1999 and Sawai et al, *Biochim. Biophyr. Res. Comm.* 248:315-323, 1998. Many properties of alphavirus vectors make them a desirable alternative to other virus-derived vector systems being developed, including rapid engineering of expression constructs, production of high-titered stocks of infectious particles, infection of nondividing cells, and high levels of expression (Strauss et al, 1994 supra). Use of Sindbis virus for gene therapy has been described. (Wahlfors et al, *Gene. Ther.* 7:472-480, 2000 and Lundstrom, *J. Recep. Sig. Transduct. Res.* 19(1-4):673-686, 1999.

In another embodiment, a vector can be introduced to cells by lipofection or with other transfection facilitating agents (peptides, polymers, etc.). Synthetic cationic lipids can be used to prepare liposomes for in vivo and in vitro transfection of a gene encoding a marker (Feigner et al, *Proc. Natl. Acad. Sci. USA* 84:7413-7417, 1987 and Wang et al, *Proc. Natl. Acad. Sci. USA* 84:7851-7855, 1987). Useful lipid compounds and compositions for transfer of nucleic acids are described in PCT Publication Nos. WO 95/18863 and WO 96/17823, and in U.S. Pat. No. 5,459,127.

It is also possible to introduce the vector in vivo as a naked DNA plasmid. Naked DNA vectors for gene therapy can be introduced into desired host cells by methods known in the art, e.g., electroporation, microinjection, cell fusion, DEAE dextran, calcium phosphate precipitation, use of a gene gun, or use of a DNA vector transporter (see, e.g., Wilson, et al, *J. Biol. Chem.* 267:963-967, 1992; Williams et al, *Proc. Natl. Acad. Sci. USA* 88:2726-2730, 1991). Other reagents commonly used for transfection of plasmids include, but are by no means limited to, FuGene, Lipofectin, and Lipofectamine. Receptor-mediated DNA delivery approaches can also be used (Wu et al, *J. Biol. Chem.* 263:14621-14624, 1988). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Vilquin et al, *Gene Ther.* 8:1097, 2001; Payen et al, *Exp. Hematol.* 29:295-300, 2001; Mir, *Bioelectrochemistry* 53:1-10, 2001; PCT Publication Nos. WO 99/01157, WO 99/01158 and WO 99/01175).

Pharmaceutical compositions suitable for such gene therapy approaches and comprising nucleic acids encoding an anti-PCSK9 antagonist of the present invention are included within the scope of the present invention.

In another aspect, the present invention provides a method for identifying, isolating, quantifying or antagonizing PCSK9 in a sample of interest using a PCSK9-specific antagonist of the present invention. The PCSK9-specific antagonists may be utilized as research tools in immunochemical assays, such as Western blots, ELISAs, radioimmunoassay, immunohistochemical assays, immunoprecipitations, or other immunochemical assays known in the art (see, e.g., Immunological Techniques Laboratory Manual, ed. Goers, J. 1993, Academic Press) or various purification protocols. The antagonists may have a label incorporated therein or affixed thereto to facilitate ready identification or measurement of the activities associated therewith. One skilled in the art is readily familiar with the various types of detectable labels (e.g., enzymes, dyes, or other suitable molecules which are either readily detectable or cause some activity/result that is readily detectable) which are or may be useful in the above protocols.

An additional aspect of the present invention are kits comprising PCSK9-specific antagonists or pharmaceutical compositions disclosed herein and instructions for use. Kits typically but need not include a label indicating the intended use of the contents of the kit. The term label includes any writing, or recorded material supplied on or with the kit, or which otherwise accompanies the kit. In specific embodiments wherein the pharmaceutical composition is provided lyophilized, the kit may include sterile water or saline for reconstitution of the formulation into liquid form. In specific embodiments, the amount of water or saline is from about 0.1 ml to 1.0 ml.

The following examples are provided to illustrate the present invention without limiting the same hereto:

EXAMPLE 1

Isolation of Recombinant Fab Display Phage 1B20

Recombinant Morphosys HuCAL Gold Fab phage display libraries (see, e.g., Knappik et al., 2000 *J. Mol. Biol.* 296:57-86) were panned against immobilized recombinant human and murine PCSK9 through a process which is briefly described as follows: PCSK9 protein was chemically biotinylated (Pierce, Cat. #21455) per manufacturer's instruction. The Moprhosys phage Fab display libraries were pooled and pre-absorbed three times to blocked strepavidin coated beads (Dynal beads M280). With the goal of isolating cross-reactive Fabs, human (h) and mouse (m) PCSK9 were alternated as follows: rounds 1/2/3 utilized PCSK9 from h/m/h.

For each of the three rounds of panning, the preabsorbed phage library was incubated with preblocked biotinylated PCSK9 (150 nM for first round and 100 nM for subsequent rounds) immobilized to strepavidin coated Dynal beads. The immobilized phage-PCSK9 complexes were washed sequentially with 5 quick washes with PBS/0.05% Tween™ 20 followed by 4 quick washes with PBS and transferred in PBS to a fresh blocked tube. Bound phages were then eluted with 20 mM DTT. TG1 cells were infected with eluted phages. Pooled cultures of phagemid-bearing cells (chloramphenicol-resistant) were grown up and frozen stocks of phagemid-bearing cultures were made. Phage were rescued from culture by co-infection with helper phage, and phage stocks for next round of panning were made.

After the third round of panning phagemid-infected cells were grown overnight and phagemid DNA was prepared.

XbaI-EcoRI inserts from Round 3 phagemid DNA were subcloned into Morphosys Fab expression vector pMORPH_x9_MH to yield plasmid pMORPHx9_MH/PCSK9_6_CX1_B20 (see, e.g., FIG. 1), and a library of Fab expression clones was generated in *E. coli* TG1 F−. Transformants were spread on LB+chloramphenicol+glucose plates and grown overnight to generate bacterial colonies. Individual transformant colonies were picked and placed into wells of two 96-well plates for growth and screening for Fab expression.

EXAMPLE 2

Elisa Screening of Bacterially Expressed Fabs

Cultures of individual transformants were IPTG-induced and grown overnight for Fab expression. Culture supernatants (candidate Fabs) were incubated with purified V5-, His-tagged PCSK9 protein immobilized in wells of 96-well Nunc Maxisorp plates, washed with 0.1% Tween™ 20 in PBS using a plate washer, incubated with HRP-coupled anti-Fab antibody, and washed again with PBS/Tween™ 20. Bound HRP was detected by addition of TMP substrate, and A450 values of wells were read with a plate reader.

Negative controls were included as follows:

Controls for nonspecific Fab binding on each plate were incubated with parallel expressed preparations of anti-EsB, an irrelevant Fab.

Growth medium only.

Positive controls for ELISA and Fab expression were included as follows: EsB antigen was bound to three wells of the plate and subsequently incubated with anti-EsB Fab. To control for Fabs reacting with the V5 or His tags of the recombinant PCSK9 antigen, parallel ELISAs were performed using V5-, His-tagged secreted alkaline phosphatase protein (SEAP) expressed in the same cells as the original PCSK9 antigen and similarly purified. Putative PCSK9-reactive Fabs were identified as yielding >3× background values when incubated with PCSK9 antigen but negative when incubated with SEAP. Clones scoring as PCSK9-reactive in the first round of screening were consolidated onto a single plate, re-grown in triplicate, re-induced with IPTG, and re-assayed in parallel ELISAs vs. PCSK9 and SEAP. Positive and negative controls were included as described above. Clones scoring positive in at least 2 of 3 replicates were carried forward into subsequent characterizations. In cases of known or suspected mixed preliminary clones, cultures were re-purified by streaking for single colonies on 2×YT plates with chloramphenicol, and liquid cultures from three or more separate colonies were assayed again by ELISAs in triplicate as described above.

EXAMPLE 3

DNA Sequence Determination of PCSK9 Elisa-Positive Fab Clones

Bacterial cultures for DNA preps were made by inoculating 1.2 ml 2×YT liquid media with chloramphenicol from master glycerol stocks of positive Fabs, and growing overnight. DNA was prepared from cell pellets centrifuged out of the overnight cultures using the Qiagen Turbo Mini preps performed on a BioRobot 9600. ABI Dye Terminator cycle sequencing was performed on the DNA with Morphosys defined sequencing primers and run on an ABI 3100 Genetic Analyzer, to obtain the DNA sequence of the Fab clones. DNA sequences were compared to each other to determine unique clone sequences and to determine light and heavy chain subtypes of the Fab clones.

EXAMPLE 4

Expression and Purification of Fabs from unique PCSK9 Elisa-Positive Clone

Fabs from ELISA-positive clone 1B20 and the EsB (negative control) Fab were expressed by IPTG-induction in *E. coli* TG1F-cells. Cultures were lysed and the His-tagged Fabs were purified by immobilized metal ion affinity chromatography (IMAC), and proteins were exchanged into 25 mM HEPES pH 7.3/150 mM NaCl by centrifugal diafiltration. Proteins were analyzed by electrophoresis on Caliper LabChip 90 and by conventional SDS-PAGE, and quantified by Bradford protein assay. Purified Fab protein was re-assayed by ELISA in serial dilutions to confirm activity of purified Fab. Positive and Negative controls were run as before. Purified Fab preparations were then analyzed as described below.

EXAMPLE 5

Conversion of 1B20 Fab to Full Length IgG

The DNA sequence encoding the 1B20 light kappa chain variable region was amplified by polymerase chain reaction from plasmid template pMORPHx9_MH/PCSK9__6_CX1_B20, using forward primer 5'-ACAGATGCCAGATGCGATATCGTGATGACCCAGA-3' (SEQ ID NO: 31) and reverse primer 5'-TGCAGCCACCGTACGTTTAATTTCAACTTTCGTACC-3' (SEQ ID NO: 32). The product of this amplification was cloned into plasmid pV 1 JNSA-GS-FB-LCK that had been previously digested with FspI and BmtI, using the InFusion cloning system (Clontech). The resulting plasmid was verified by DNA sequencing across the variable region. Endotoxin-free plasmid preparations were made using the Qiagen Endo-Free plasmid maxiprep kit.

The DNA sequence encoding the heavy gamma chain variable region of pMORPHx9_MH/PCSK9__6_CX1_B20 was amplified by polymerase chain reaction using forward primer 5'-ACAGGTGTCCACTCGCAGGTGCAATTGGTTCAGAGC-3' (SEQ ID NO: 33) and reverse primer 5'-GCCCTTGGTGGATGCTGAGCTAACCGTCACCAGGGT-3' (SEQ ID NO: 34), and the amplified product was cloned into plasmid pV1JNSA-BF-HCG2M4 that had been previously digested with FspI and BmtI. The resulting plasmid was verified by DNA sequencing across the variable region. Endotoxin-free plasmid preparations were made using the Qiagen Endo-Free plasmid maxiprep kit.

Full-length IgG was obtained by co-transfection of HEK293 cells with the 1B20 light chain- and heavy-chain-encoding plasmids, following by Protein A purification of the expressed IgG.

EXAMPLE 6

Kinetic Evaluation of FAB:PCSK9 Interactions with Surface Plasmon Resonance ("SPR")

SPR measurements were performed using a Biacore™ (Pharmacia Biosensor AB, Uppsala, Sweden) 2000 system. Sensor chip CM5 and Amine Coupling Kit for immobilization were from Biacore™.

Anti-Fab IgG (Human specific) (Sigma, catalog #15260) was covalently coupled to surfaces 1 and 2 of a Sensor Chip CM5 via primary amine groups, using the immobilization wizard with the "Aim for immobilization" option using Biacore™ Amine Coupling Kit (cat# BR-1000-50. A target immobilization of 5000 RU was specified. The wizard uses a 7 minute activation with a 1:1 mixture of 100 mM NHS (N-Hydroxysuccinimide) and 400 mM EDC (1-ethyl-3-(3-dimethylaminopropyl)-carbodiimide), injects the ligand in several pulses to achieve the desired level, then deactivates the remaining surface with a 7 minute pulse of ethanolamine.

Anti-PCSK9 Fabs were captured on capture surface 2, and surface 1 was used as a reference for kinetic studies of Fab: PCSK9 interactions. Each Fab was captured by flowing a 500 ng/ml solution at 5 or 10 μl/min for 1-1.5 minutes to reach a target $R_L$ for an R max of 100-150 RU for the reaction. 5-10 concentrations of hPCSK9v5H is or mPCSK9v5H is antigens were flowed across the surface at 30 μl/minute for 3-4 minutes. 15-60 minutes dissociation time was allowed before regeneration of the Anti-Fab surface with a 30 second pulse of 10 mM glycine pH 2.0.

BiaEvaluation Software was used to evaluate the sensograms from the multiple concentration of PCSK9 antigen analyzed with each Fab, to estimate the kinetics constants of the Fab:PCSK9 interactions.

The kinetic constants were determined as follows:

TABLE 2

| 1B20 Fab | hPCSK9v5His | mPCSK9v5His |
|---|---|---|
| $k_a$ (1/Ms) | 6.6E+04 ± 6.1E+03 | 1.41E+05 ± 1.2E+04 |
| $k_d$ (1/s) | 4.8E−05 ± 7.4E−06 | 7.2E−05 ± 2.9E−06 |
| $K_A$ (1/M) | 1.5E+09 ± 3.0E+08 | 2.0E+09 ± 1.5E+08 |
| $K_D$ (M) | 7.4E−10 ± 1.6E−10 | 5.1E−10 ± 3.8E−11 |

EXAMPLE 7

Kinetic Evaluation of IgG:PCSK9 Interactions with Surface Plasmon Resonance ("SPR")

SPR measurements were performed using a Biacore™ (Pharmacia Biosensor AB, Uppsala, Sweden) 2000 system. Sensor chip CM5 and Amine Coupling Kit for immobilization were from Biacore™.

A goat Anti-Human IgG (Caltag, catalog #H10700) was covalently coupled to surfaces 1 and 2 of a Sensor Chip CM5 via primary amine groups, using the immobilization wizard with the "Aim for immobilization" option using Biacore™ Amine Coupling Kit (cat# BR-1000-50. A target immobilization of 5000 RU was specified. The wizard uses a 7 minute activation with a 1:1 mixture of 100 mM NHS (N-Hydroxysuccinimide) and 400 mM EDC (1-ethyl-3-(3-dimethylaminopropyl)-carbodiimide), injects the ligand in several pulses to achieve the desired level, then deactivates the remaining surface with a 7 minute pulse of ethanolamine.

Anti-PCSK9 IgGs were captured on capture surface 2, and surface 1 was used as a reference for kinetic studies of IgG: PCSK9 interactions. IgG was captured by flowing a 10 nM solution at 10 μl/min for 1-1.5 minutes to reach a target $R_L$ for an R max of 100-150 RU for the reaction. 5-10 concentrations of hPCSK9v5H is or mPCSK9v5H is antigens were flowed across the surface at 30 or 60 μl/minute for 4 minutes. 15-60 minutes dissociation time was allowed before regeneration of the Anti-IgG surface with a 60 second pulse of 10 mM Glycine pH 1.7.

BiaEvaluation Software was used to evaluate the sensograms from the multiple concentration of PCSK9 antigen analyzed with each IgG, to estimate the kinetics constants of the IgG:PCSK9 interactions.

The kinetic constants were determined as follows:

TABLE 3

| 1B20 IgG | hPCSK9v5His | mPCSK9v5His |
|---|---|---|
| $k_a$ (1/Ms) | 5.3E+04 ± 6.8E+03 | 8.9E+04 ± 3.2E+03 |
| $k_d$ (1/s) | 4.3E−05 ± 4.5E−06 | 1.2E−04 ± 6.4E−06 |
| $K_A$ (1/M) | 1.4E+09 ± 2.8E+08 | 7.4E+08 ± 4.2E+07 |
| $K_D$ (M) | 8.9E−10 ± 1.6E−10 | 1.4E−09 ± 8.2E−11 |

EXAMPLE 8

PCSK9-LDLR TR-FRET Assay for 1B20

This assay is a variant of the one described in Fisher et al., 2007 *J. Biol. Chem.* 282:20502-20512. AlexaFluor647-labeled PCSK9 (final concentration 10 nM) was combined with varying amounts of 1B20 and to this was added Eu(8044)-labeled LDLR ectodomain to a final concentration of ~4 nM (sufficient to give ~20,000 counts at $Fl_{620}$ nM on the Rubystar) in 10 mM HEPES (pH 7.4), 150 mM NaCl, 0.1 mM $CaCl_2$, 0.05% (w/v) BSA in a total volume of 50 μL using 96 well black Dynatech U bottom plates. After at least 90 minutes of equilibration, samples were read in a Rubystar reader (BMG Corp.) using 20 flashes per well, a 50 usec integration delay, and a 200 usec total integration time. Data were expressed as the ratio of ($Fl_{665}/Fl_{620}$×10000) and an $IC_{50}$ for 1B20 was determined from the inflection point of a sigmoidal dose-response curve using a standard four parameter fit.

Figure 2:
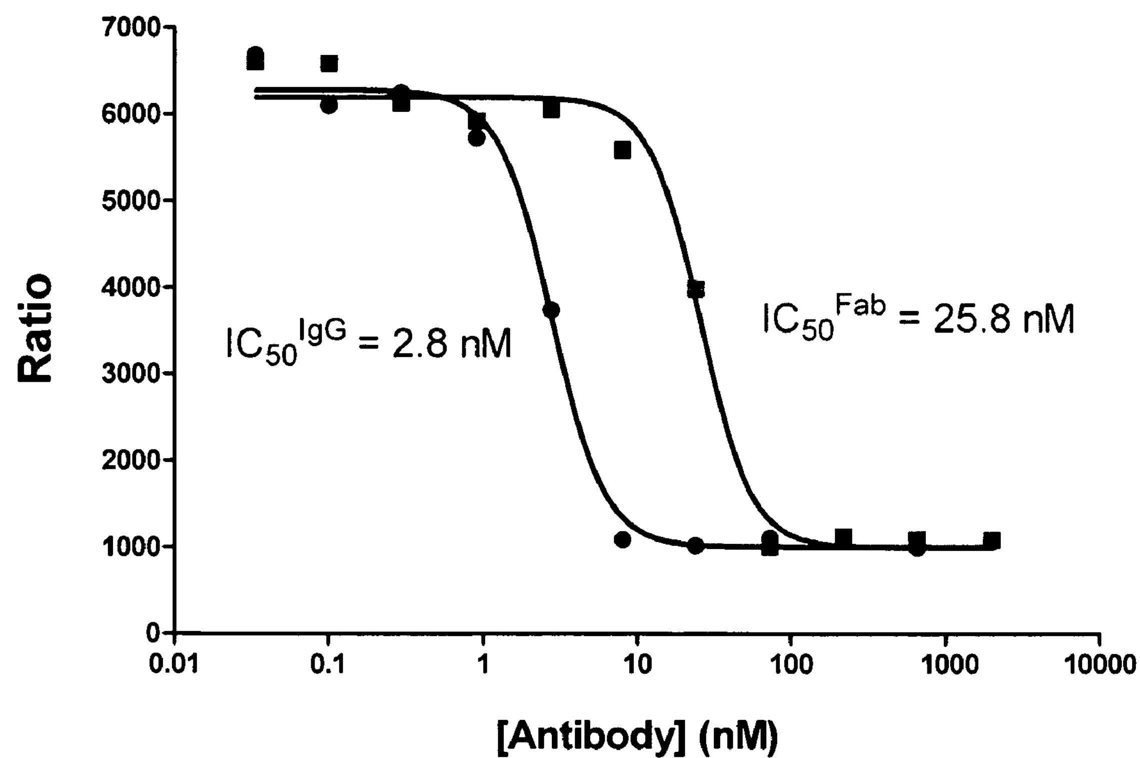
FIG. 2 illustrates the activity of 1B20 in a PCSK9-LDLR interaction TR-FRET assay. Both the Fab and IgG of 1B20 are potent and inhibit the interaction fully. For the experiment, [AF647-PCSK9]=10 nM, [Eu-sLDLR]~4 nM (~20000 counts at $FI_{620}$ nm).

FIG. 2 illustrates the activity of 1B20 in the PCSK9-LDLR interaction TR-FRET assay. Both the Fab and IgG of 1B20 are potent and inhibit the PCSK9-LDLR interaction fully.

EXAMPLE 9

Exopolar Assay

Effects of Exogenous PCSK90N Cellular LDL Uptake

On day 1, 30,000 HEK cells/well were plated in a 96 well polyD-lysine coated plate. On day 2, the media was switched to no-serum containing DMEM media. On day 3, the media was removed and the cells were washed with OptiMEM. Purified PCSK9 was added in 100 μl of DMEM media containing LPDS and dI-LDL. The plates were incubated at 37° C. for 6.5 hrs. The cells were washed quickly in TBS containing 2 mg/ml BSA; then washed in TBS-BSA for 2 minutes; and then washed twice (but quickly) with TBS. The cells were lysed in 100 μl RIPA buffer. Fluorescence was then measured in the plate using an Ex 520, Em 580 nm. The total cellular protein in each well was measured using a BCA Protein Assay and the fluorescence units were then normalized to total protein.

The Exopolar Assay is effective for characterizing variant effects on LDL uptake; see Table 4 below illustrating how the potencies of PCSK9 mutants correlate with plasma LDL-cholesterol in the Exopolar Assay.

TABLE 4

| Mutation | Gain/Loss | LDL-C (mg/dI) | EC-50 (nM) Exopolar |
|---|---|---|---|
| S127R | Gain | 277 | 14 |
| D374Y | Gain | 388 | 1.3 |
| Wild-type | | 140 | 51 |
| R46L | Loss | 116 | 78 |

Results: 1B20, both Fab and IgG, dose-dependently inhibited the effects of both human and murine PCSK9 on LDL uptake; an effect which was reproducibly observed. The amount of PCSK9 added to the cells was ~60-320 nM.

1B20 (Fab) comprises a light chain of SEQ ID NO: 1 (comprising a VL of SEQ ID NO: 27) and a Fd chain of SEQ ID NO: 9 inclusive of linkers and tags (comprising a VH of SEQ ID NO: 11).

1B20 (IgG) comprises a light chain of SEQ ID NO: 26, and a heavy chain comprising SEQ ID NO: 25.

Figure 3:
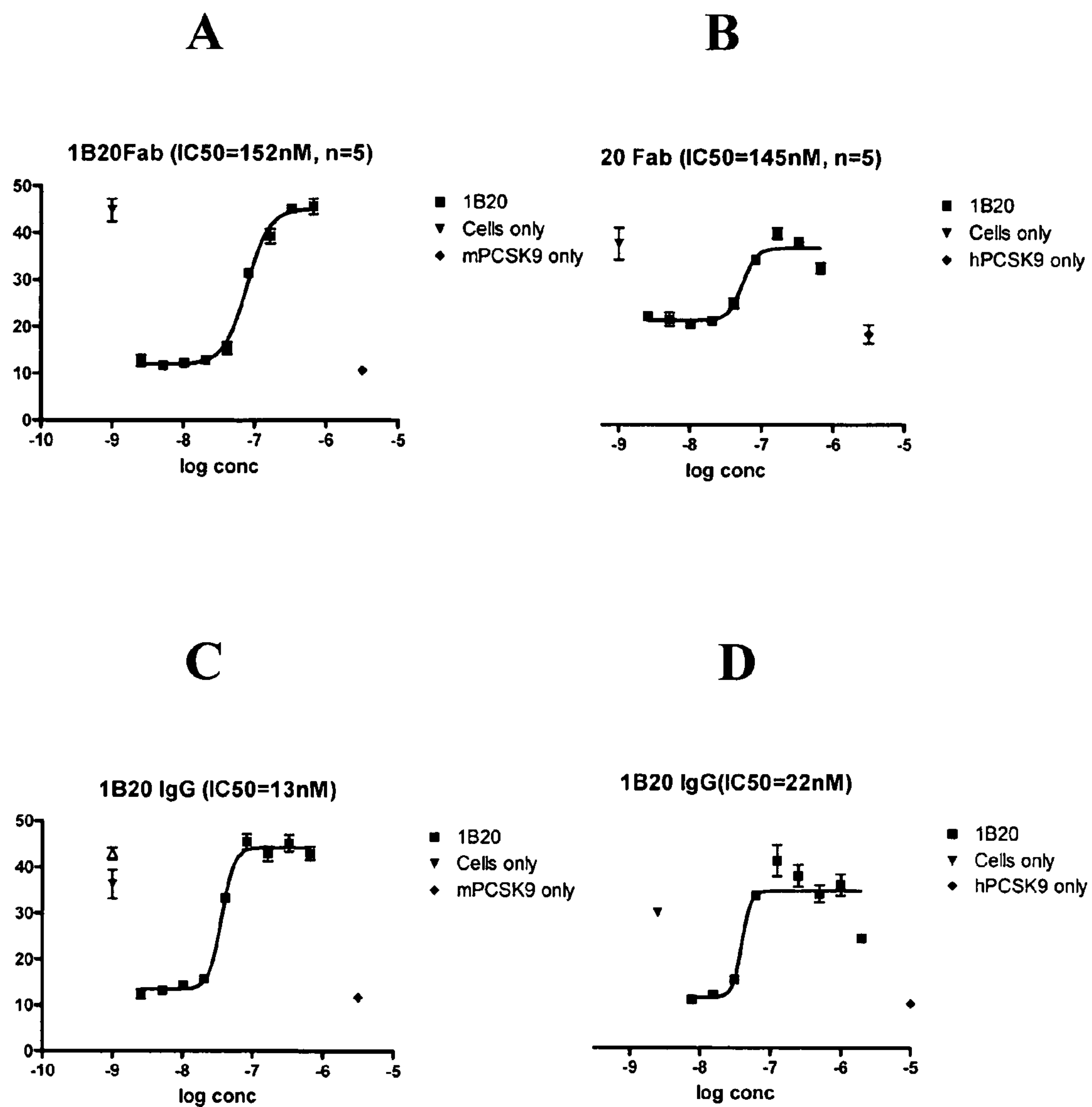
FIGS. 3A-3D illustrate (i) 1B20 (Fab)'s dose-dependent inhibition of murine PCSK9-dependent loss of cellular LDL-uptake (FIG. 3A); (ii) 1B20 (Fab)'s dose-dependent inhibition of human PCSK9-dependent loss of cellular LDL-uptake (FIG. 3B); (iii) 1B20 (IgG)'s dose-dependent inhibition of murine PCSK9-dependent loss of cellular LDL-uptake (FIG. 3C); and (iv) 1B20 (IgG)'s dose-dependent inhibition of human PSCK9-dependent loss of cellular LDL-uptake (FIG. 3D). 1B20 clearly cross-reacts with both human and mouse PCSK9.

FIGS. 3A-3D illustrate (i) 1B20 (Fab)'s dose-dependent inhibition of murine PCSK9-dependent loss of cellular LDL-uptake (FIG. 3A); (ii) 1B20 (Fab)'s dose-dependent inhibition of human PCSK9-dependent loss of cellular LDL-uptake (FIG. 3B); (iii) 1B20 (IgG)'s dose-dependent inhibition of murine PCSK9-dependent loss of cellular LDL-uptake (FIG. 3C); and (iv) 1B20 (IgG)'s dose-dependent inhibition of human PSCK9-dependent loss of cellular LDL-uptake (FIG. 3D).

1B20 clearly cross reacts with both human and mouse PCSK9. FIGS. 3A-3D have two controls: (i) a cell only control, showing the basal level of cellular LDL uptake, and (ii) a PCSK9 (5 μg/ml) control which shows the level of PCSK9-dependent loss of LDL-uptake. The titration experiments which contain 1B20 and PCSK9 were done at a fixed concentration of PCSK9 (5 μg/ml) and increasing concentrations of 1B20 shown in the graphs.

1B20 can inhibit the effect of PCSK9 on cellular LDL uptake. $IC_{50}$s for 1B20 (Fab) are 152 nM (n=5) and 145 nM (n=5) for mouse and human PCSK9 protein, respectively.

$IC_{50}$s for 1B20 (IgG) are 13 nM and 22 nM for mouse and human PCSK9 protein, respectively.

EXAMPLE 10

PCSK9 Cellular Uptake

The assay that follows was carried out according to the methods of Fisher et al., 2007 *J. Biol. Chem.* 282: 20502-12.

Cells treated with Alexa Fluor 647-labeled PCSK9 were imaged as follows. CHO cells were plated on poly-D-lysine-coated 96-well optical CVG sterile black plates (Nunc) at a density of 20,000 cells/well. Cells were plated in F-12K medium (nutrient mixture, Kaighn's modification (1×)) (Invitrogen) containing 100 units of penicillin and 100 μg/ml streptomycin sulfate and supplemented with 10% FBS. Plates were incubated overnight at 37° C. and 5% $CO_2$. The following morning, the medium was removed and replaced with 100 μl of F-12K medium containing 100 units of penicillin and 100 μg/ml streptomycin sulfate. After 18 h, the medium was removed. Purified PCSK9 protein was labeled with Alexa Fluor 647 as described under "Experimental Procedures." Alexa Fluor 647-labeled PCSK9 (1, 5, or 20 μg/ml) was added in 50 μl of F-12K medium containing 10% lipoprotein-deficient serum to the cells. The plates were incubated at 37° C. for 4 h, and the cells were washed quickly with Tris-buffered saline before imaging. To label cellular nuclei, Hoechst 33342 at a final concentration of 0.1 μg/ml was added to each well. The plates were run on an Opera imager (Evotec Technologies GmbH, Hamburg, Germany) with a x40 water immersion objective. Images were captured using excitation wavelengths of 405 nm for fluorescent nuclei and 635 nm for Alexa Fluor 647-labeled PCSK9. For each well, 11 individual fields containing >500 cells were captured for two emission wavelengths. The data were analyzed using a customized algorithm written using the Acapella language (Evotec Technologies GmbH). The algorithm identified and marked the nuclear and cytoplasmic areas of individual cells, followed by measurement of the total cytoplasmic intensity of the cell. The intensity was expressed in arbitrary fluorescent units.

For testing the 1B20 Ab, the identical procedure was used, with HEK293 cells.

Figure 4:
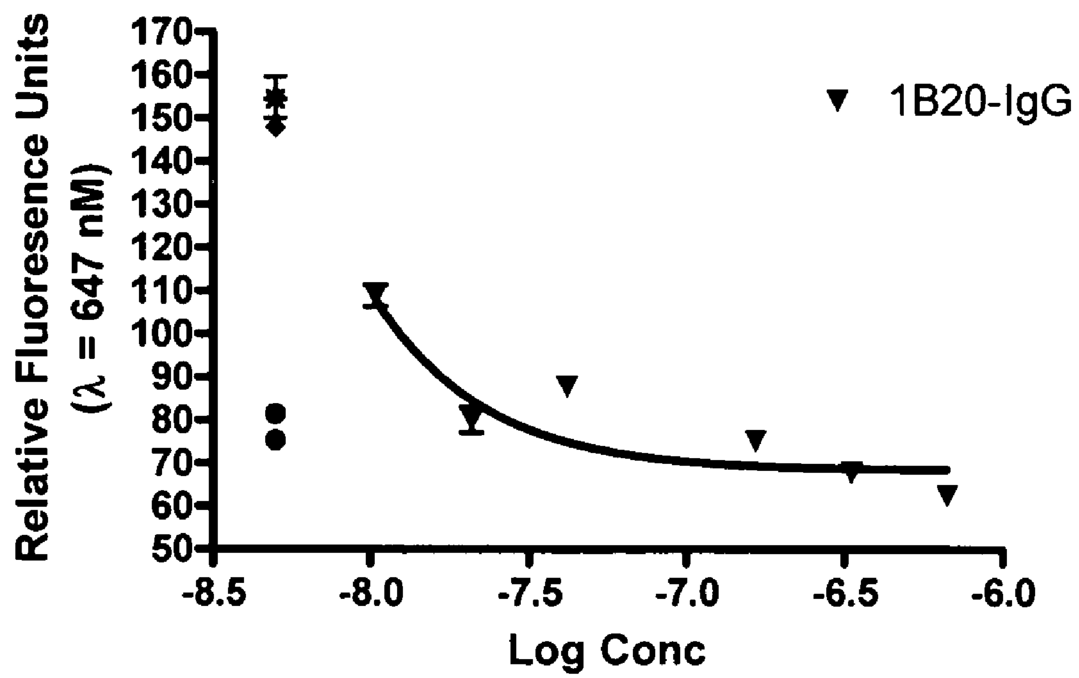
FIG. 4 illustrates inhibition of PCSK9 internalization by 1B20 (IgG). HEK293 cells were plated and AlexaFluor-labeled PCSK9 and LDL were then added to cells and incubated at 37° C. for 4 hrs. Following incubation, the amount of PCSK9 or LDL internalized by cells was determined using cofocal microscopy. Controls included the addition of cells alone (No treatment), and only AF-labeled PCSK9 in addition to 50× (250 μg/ml) unlabeled PCSK9 (50× Cold Wt). In addition to 5 μg/ml wild-type AF-labeled PCSK9 and 10 μg/ml AF-labeled LDL, increasing amounts of the 1B20 IgG was added, resulting in subsequent inhibition of PCSK9 internalization into cells. Together, these studies demonstrate that the 1B20 IgG prevents PCSK9 internalization into cells.

Results: FIG. 4 illustrates inhibition of PCSK9 internalization by the 1B20 IgG.

EXAMPLE 11

In Vivo ASSAY

Whole IgG of human 1B20 was tested in vivo in mice and changes in the level of LDL cholesterol were monitored. The mice used in these studies were (B6×B6-Tg(CETP) $Ldlr^{tml}$) F1 mice which are hemizygous for the transgenic (Tg) expression of human CETP (which mice lack) as well as the disruption of the LDL receptor (tml). These mice are particularly useful because of their human-like lipid profiles and LDL-rich nature.

Each mouse was bled twice, once at the beginning of the study to establish individual baseline levels of LDL cholesterol ("pre") and a second time 3 hours later ("post") to assess what changes took place in LDL levels after treatment. Each mouse received two IV doses of Dulbecco's PBS as a vehicle control, 1B20 IgG (0.5 mg), or 1B20 Fab fragments (0.5 mg) over the course of 3 hours. The 1B20 whole IgG was centrifuged at 230,000×g to remove aggregates immediately prior to injection.

Figure 5:
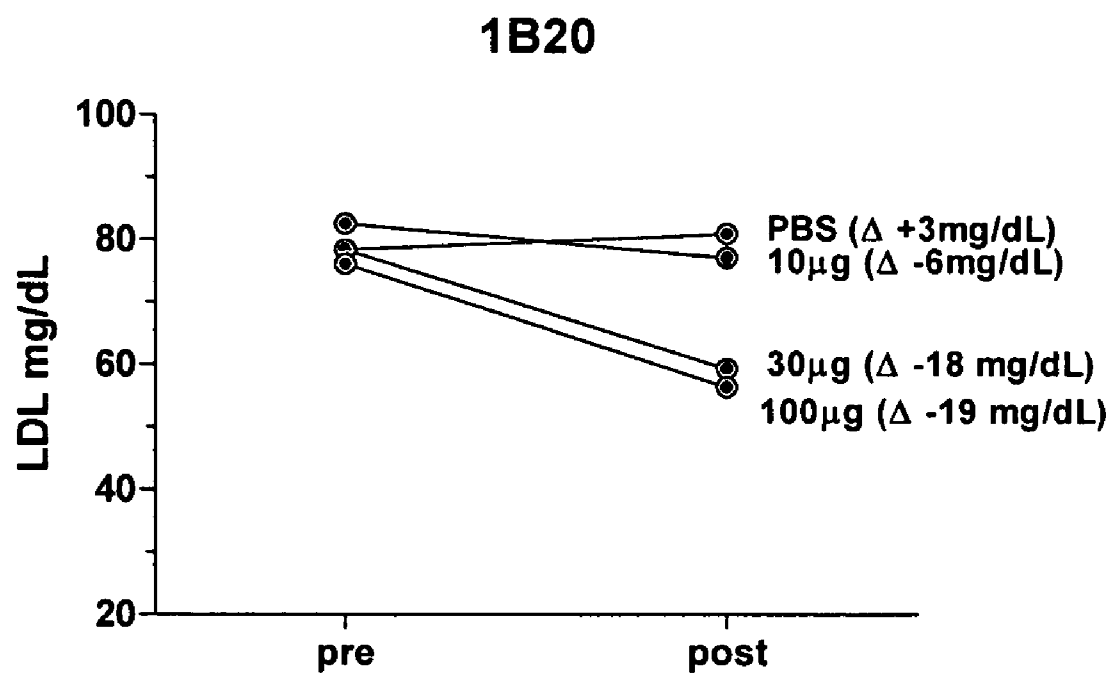
FIG. 5 illustrates the LDL levels for each mouse represented by a set of connected symbols; the change in LDL (postbleed—prebleed) being shown as an average for each treatment group (Δ mg/dL). Treatment with PBS had no effect on LDL measurements (−4 mg/dL, 5% reduction). In contrast, serum LDL was reduced 20% with 1B20 whole IgG (−19 mg/dL).

In FIG. 5, the LDL levels for each mouse are represented by a set of connected symbols and the change in LDL (post-bleed—prebleed) is shown as an average for each treatment group (Δ mg/dL). Treatment with PBS had no effect on LDL measurements (−4 mg/dL, 5% reduction). In contrast, serum LDL was reduced 20% with 1B20 whole IgG (−19 mg/dL).

EXAMPLE 12

1B20 Rhesus PK/PD Study

To characterize pharmacokinetics, pharmacodynamics and target engagement of 1B20, a single dose IV study was conducted in male Rhesus monkeys at 1, 3 and 10 mg/kg respectively (3.8-9.6 kg, n=3 per group). All Rhesus monkeys used in the study were naïve to biologics.

Monkeys were given an IV bolus dose of 1B20 via the cephalic or saphenous vein. Blood samples were collected from the saphenous/femoral vessel at designated time points post dosing and the resulting plasma/serum was stored at −70° C. until analysis.

The dosing solutions of 1B20 were prepared at 10 mg/mL (for 1 mg/kg dose) or 37.1 mg/mL (3 and 10 mg/kg dose) in 100 mM Histidine, 100 mM Arginine, 6% sucrose, pH 6.0. The dosing solutions were stored at 4° C. and kept on wet ice during dosing.

The lipoprotein analysis of the serum samples were carried out as described below. An anti-human IgG ELISA using commercially available reagents was used to quantify 1B20 levels.

Figure 7:
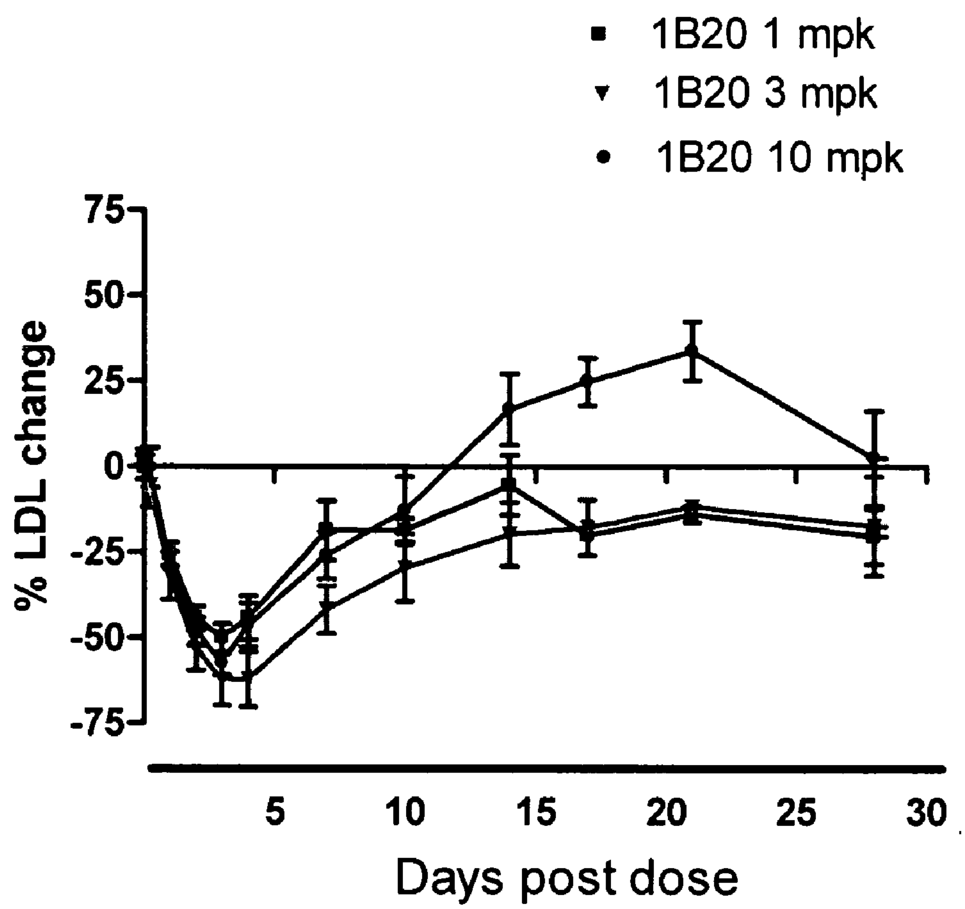
FIG. 7 illustrates 1B20 lowers LDL-C by ~50% in rhesus at 1, 3 and 10 mpk. Plotted are % LDL changes in serum at the different time points tested, post a single IV dose of antibody treatment.
Figure 8:
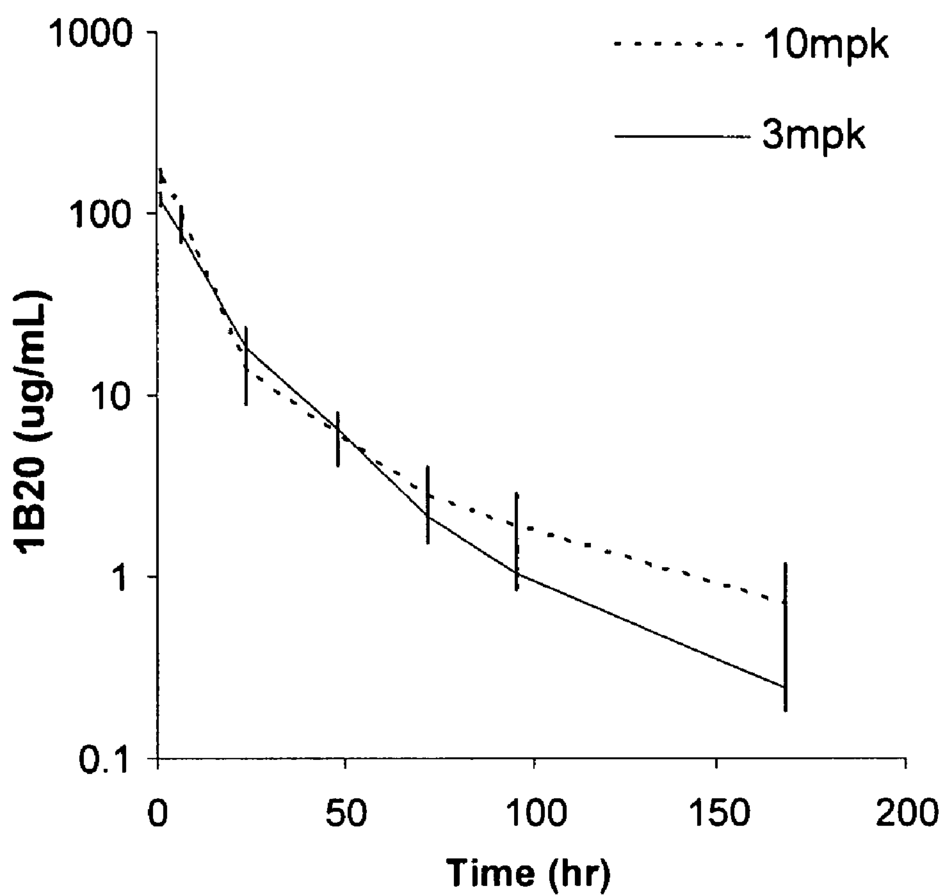
FIG. 8 illustrates the pharmacokinetic profile of 1B20 at the dose levels shown. Plotted is the serum drug (1B20) levels at time points tested following a single IV dose of antibody. The half-life of 1B20 is 39 hr.

As shown in FIG. 7, 1B20 lowered LDL-C by ≧50% at all 3 doses tested and ≧25% LDL-C lowering was observed for ≧8 days. The $t_{1/2}$ of 1B20 (FIG. 8) was 39 hr.

EXAMPLE 13

Lipoprotein Analysis of Plasma/Serum Samples from 1B20 Rhesus PK/PD Study

To generate lipoprotein profiles, plasma or serum was fractionated by chromatography over Superose-6 size exclusion column (GE LifeSciences, Inc.). Total cholesterol levels in the column effluent were continuously measured via in-line mixture with a commercially available enzymatic colorimetric cholesterol detection reagent (Total Cholesterol E, Wako USA) followed by downstream spectrophotometric detection of the reaction products at 600 nm absorbance. The first peak of cholesterol eluted from the column was attributed to VLDL, the second peak to LDL and the third to HDL; the area under each peak was calculated using software provided with the HPLC. To calculate the cholesterol concentration for each lipoprotein fraction, the ratio of the corresponding peak area to total peak area was multiplied by the total cholesterol concentration measured in the sample.

EXAMPLE 14

Formulation

Monoclonal antibodies directed towards different therapeutic targets, including but not limited to mAb1 (that comprising a light chain comprising SEQ ID NO: 26 and a heavy chain comprising SEQ ID NO: 25) were dialyzed into the appropriate formulations and concentrated to a target concentration (50, 100, 125 or 150 mg/mL). Bulk solutions were then dispensed into 3 mL glass vials for stability studies. Studies carried out in liquid form were immediately placed on stability at 2-8° C., 25° C. and 37° C. Lyophilized samples were lyophilized in a lab scale lyophilizer and the resulting lyophilized cake placed on stability stations at the same temperatures as the liquid samples.

Analytical methods included Size Exclusion Chromatography (SEC-HPLC) to measure aggregation and fragmentation, Dynamic Light Scattering (DLS) to measure particle size of concentrated samples, capillary SDS-PAGE to measure fragmentation and capillary iso-electric focusing (cIEF) to measure acidic variants formation.

The liquid stability of mAb1 (the PCSK9-specific antagonist referred to above), as well as that of mAb2, mAb3 and mAb4 (alternate antibodies, two of which are in an IgG2m4 framework disclosed herein and one of which is an IgG1, each one specific to a distinct targets) was enhanced when stored in a formulation of either 3% sucrose, 50 mM histidine, 50 mM arginine, pH 6.0 or 6% sucrose, 100 mM histidine, 100 mM arginine, pH 6.0 compared with other formulations tested, e.g., formulations containing sodium chloride, phosphate or varying lower concentrations of sucrose, histidine and arginine. The lyophilized stability of mAb2 and mAb3 (mAb 1 not tested) was enhanced when stored in a pre-lyophilization formulation of 3% sucrose, 50 mM histidine, 50 mM arginine, pH6.0 and remained stable after reconstitution with 0.5 times the original volume (0.5 ml; 0.5× original concentration of 1 ml), resulting in a formulation of approximately 6% sucrose, 100 mM histidine, 100 mM arginine, pH 6.0 and double protein concentration.

The lyophilized stability of mAb2 and mAb3 (mAb1 not tested) was enhanced when stored in a lyophilized formulation containing 3% sucrose, 50 mM histidine, 50 mM arginine, pH 6.0. Lyophilized samples were then reconstituted with half of the original volume of water, resulting in a formulation of 6% sucrose, 10 mM histidine, 100 mM arginine, pH 6.0 and a protein concentration of 100 mg/mL. Both aggregation and fragmentation were suppressed in the liquid and lyophilized formulations for all mAb's tested.

As illustrated in Table 5 below, the appearance of mAb1 after 1 month of storage at 45° C. was clear in the formulations of 3/50/50 and 6/100/100. 3/100/0 and 2/25/25 appear slightly cloudy. The other formulations tested appeared cloudy. A cloudy appearance can be an indication of visible aggregates being formed or of the solution beginning to separate into two phases.

TABLE 5

Appearance of various formulations after 1 month of storage at 45° C.

| Sample ID* | Temp (° C.) | Appearance |
|---|---|---|
| 10 His/150 NaCl | 45 | Cloudy |
| 6/100/100 | 45 | Clear |
| 6/100/100 PS80 | 45 | Clear |
| 3/50/50 pH 5.0 | 45 | Cloudy, solid precipitate visible |
| 3/50/50 | 45 | Clear |
| 3/100/0 | 45 | Slightly cloudy |
| 2/25/25 | 45 | Slightly cloudy |

*pH = 6.0 except where indicated otherwise.

Increased clipping of mAb1 was observed at pH 5.0 and in the Histidine/NaCl formulation (table 6).

TABLE 6

Changes in clipping events at non-reducing conditions after 3 months of storage.

| Non-Reduced | Difference from Time 0 in Percent Residuals (clipping) | | |
|---|---|---|---|
| Formulation ID | 2-8° C. 3M | 25° C. 3M | 37° C. 3M |
| 10 His/150 NaCl | 0.1 | 0.3 | 5.2 |
| 6/100/100 | 0.15 | 0.3 | 1.1 |
| 6/100/100 PS80 | 0.1 | 0.4 | 1.6 |
| 3/50/50 pH 5.0 | 0.05 | 2.7 | 13.95 |
| 3/50/50 | 0.1 | 0.25 | 2.1 |
| 3/100/0 | 0.2 | 0.3 | 2.8 |
| 2/25/25 | 0.1 | 0.4 | 2.8 |

Highlighted cell indicate significant levels of clipping.

Figure 9:
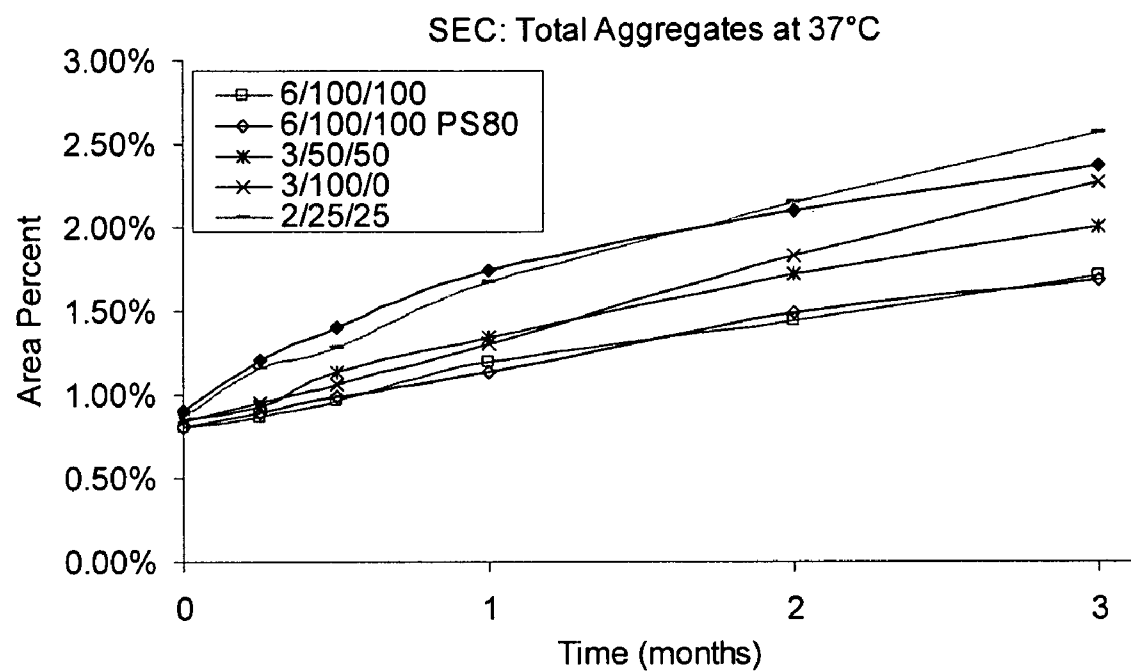
FIG. 9 illustrates the change in total aggregates at 37° C. from time 0 as measured by SEC.

The rate of aggregation of mAb1 at 37° C. is slowed when stored in a liquid formulation of 3% sucrose, 50 mM histidine, 50 mM arginine, pH 6.0 or 6% sucrose, 100 mM histidine, 100 mM arginine, pH 6.0; see FIG. 9.

Figure 10:
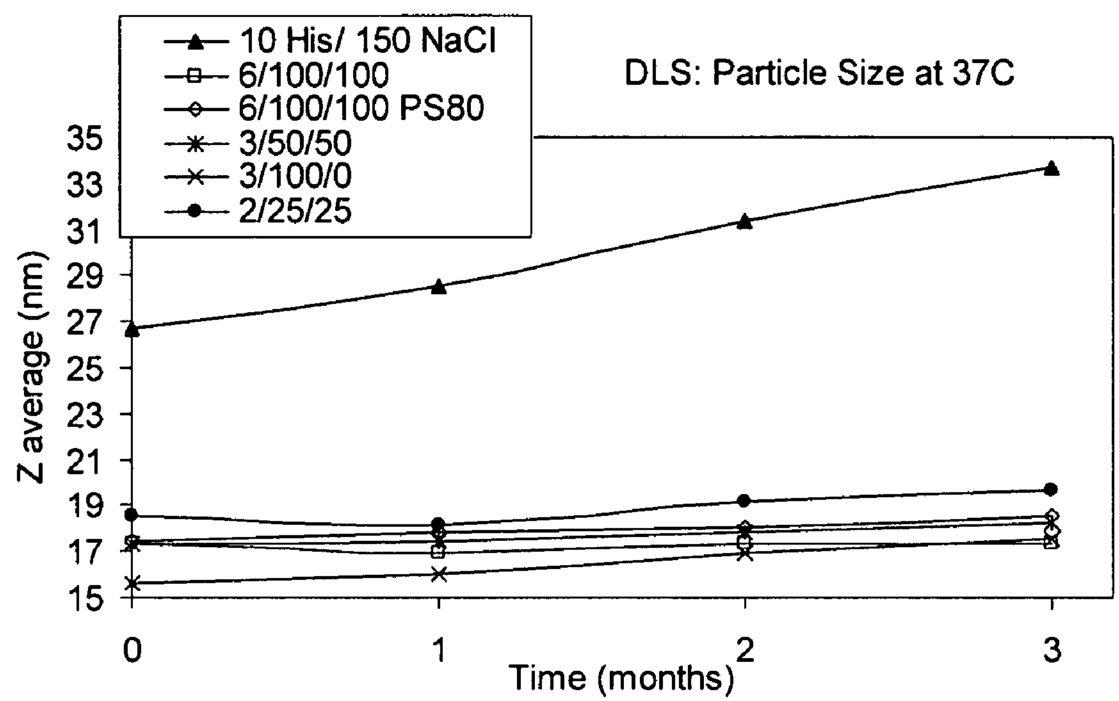
FIG. 10 illustrates Dynamic Light Scattering ("DLS") measurements of MK-2370 in various formulations after one, two and three months of storage at 37° C.

Particle size of mAb1 in histidine/NaCl particle size increased much faster than any formulation containing a combination of sucrose, histidine and arginine. This indicates that the protein is self-associating and/or forming aggregates; see FIG. 10.

Figure 11:
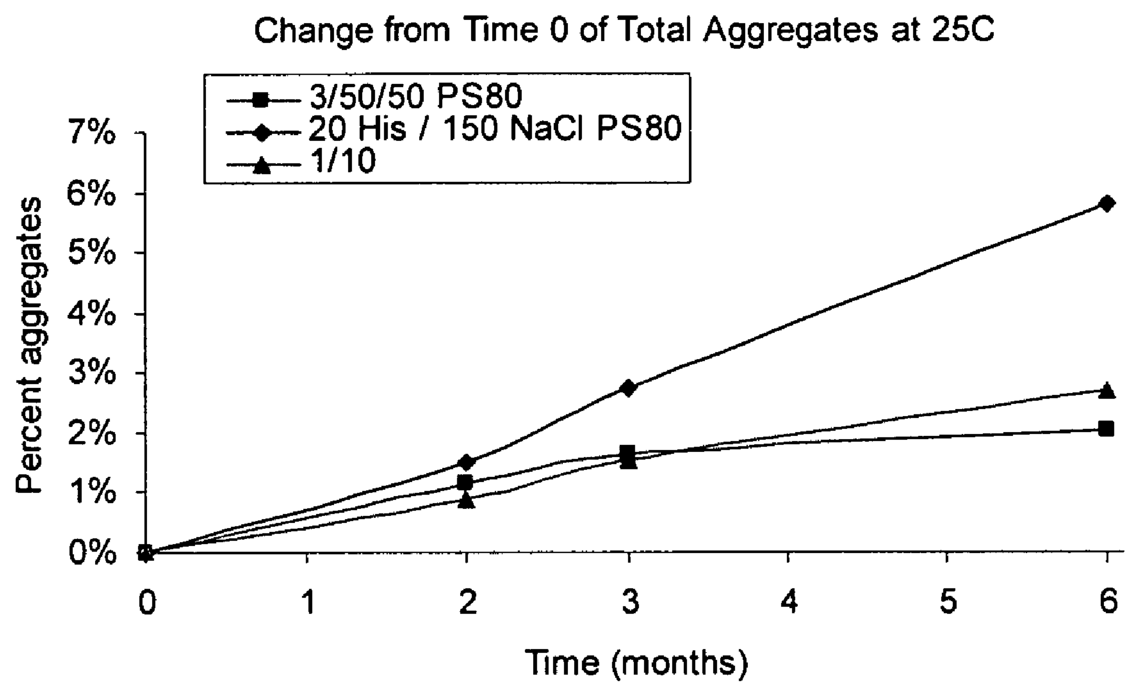
FIG. 11 illustrates the change in total aggregation at 25° C. from time 0 in liquid with a protein concentration of 50 mg/mL as measured by SEC-HPLC.
Figure 12:
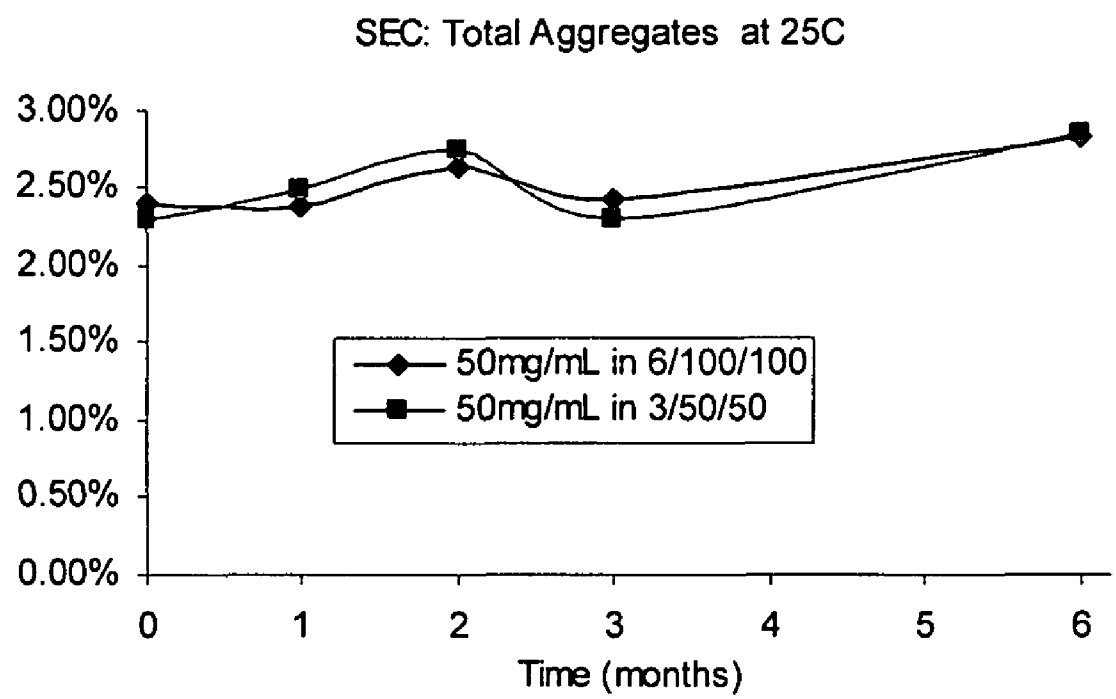
FIG. 12 illustrates the change in total aggregation at 25° C. from time 0 in liquid with a protein concentration of 50 mg/mL as measured by SEC-HPLC.
Figure 13:
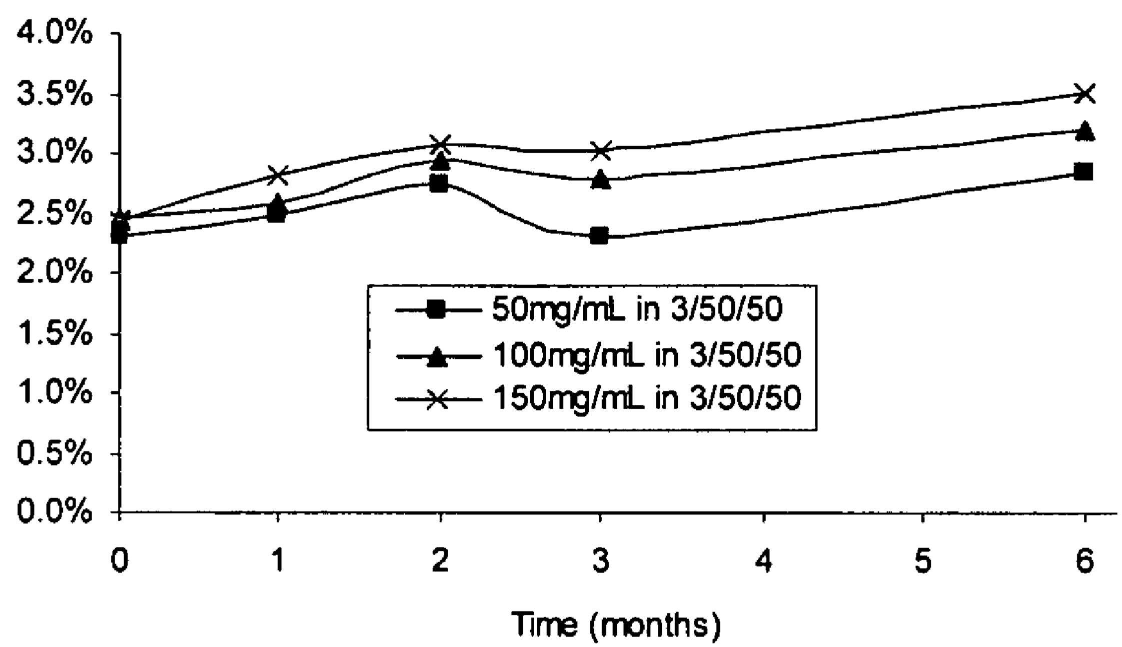
FIG. 13 illustrates total aggregation observed at 50, 100 and 150 mg/mL after 6 months storage at 25° C. in the liquid form.
Figure 14:
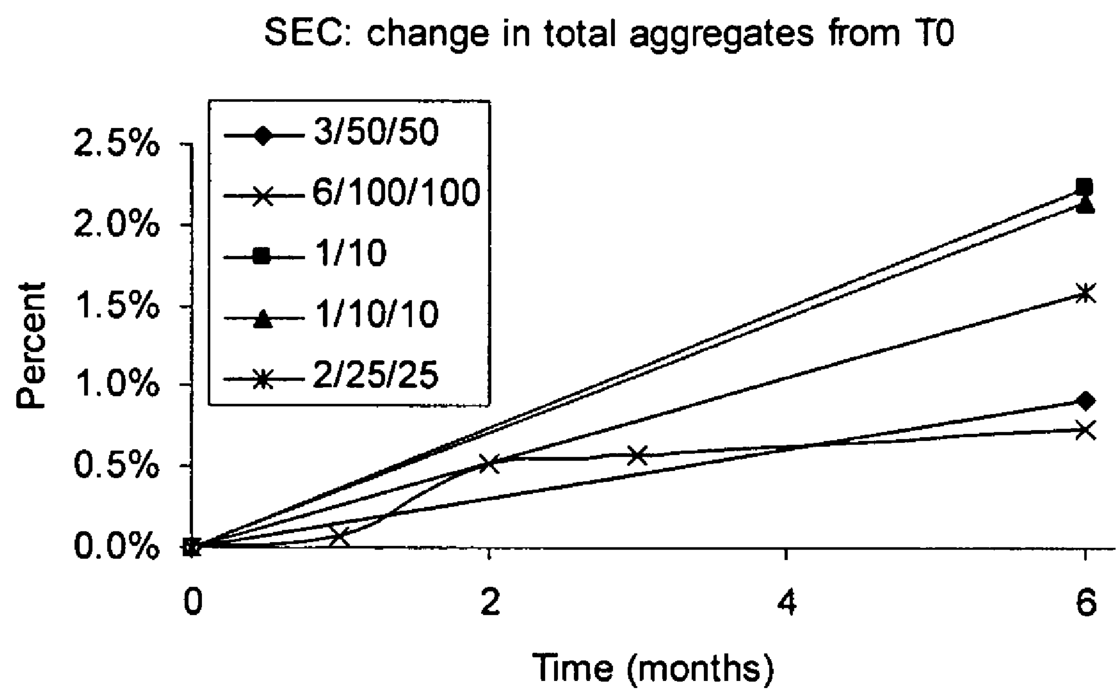
FIG. 14 illustrates the change in total aggregation at 25° C. from time 0 at 50 mg/mL as measured by SEC-HPLC; *6/100/100 data from a different study.

After 6 months of storage at 25° C. at 50 mg/mL, mAb2 contains the least aggregation when stored in a formulation of 3% sucrose, 50 mM histidine, 50 mM arginine (3/50/50) than other formulations tested; see FIG. 11. After the same amount of time at 25° C., the aggregation levels of mAb2 in 3% sucrose, 50 mM histidine, 50 mM arginine, pH 6.0 (3/50/50) and 6% sucrose, 100 mM histidine, 100 mM arginine, pH 6.0 (6/100/100) are identical; see FIG. 12.

mAb2 is stable for up to 6 months at 25° C. in 3% sucrose, 50 mM histidine, 50 mM arginine, pH 6.0 at 50 mg/mL, 100 mg/mL and 150 mg/mL; see FIG. 13.

mAb3 is stable in 3/50/50 and 6/100/100 at 50 mg/mL for 6 months at 25° C. Fewer aggregates were observed in these formulations and in 2/25/25 than in other liquid formulations tested; see FIG. 14.

Figure 15:
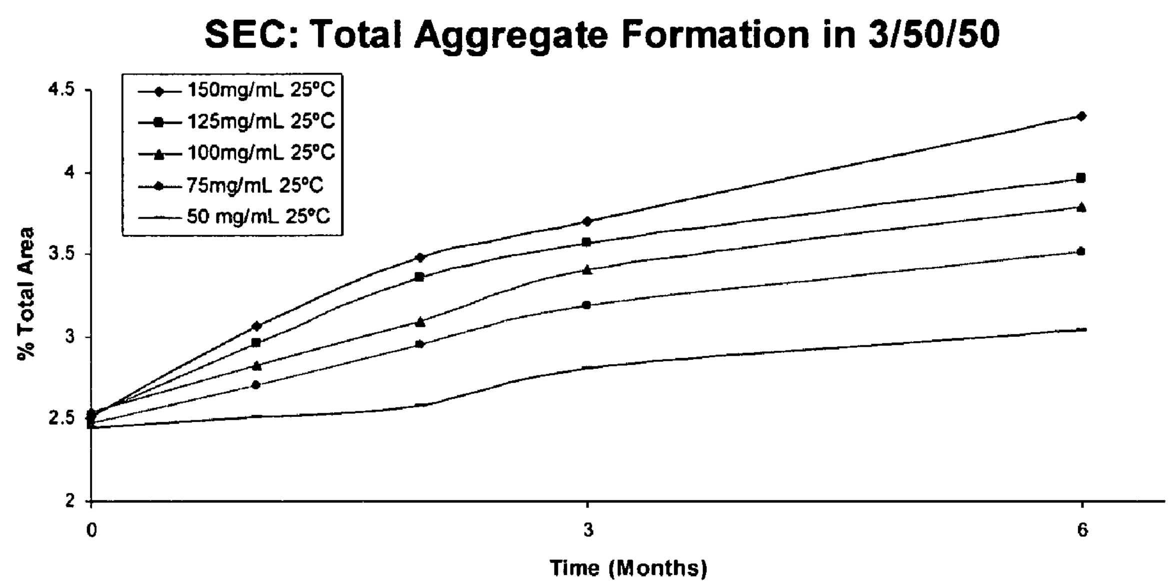
FIG. 15 illustrates total aggregates of various concentrations of mAb3 at 25° C. as measured by SEC-HPLC.

Increased aggregation of mAb3 is observed with increasing concentration in 3/50/50, but the rate of increase at 25° C. is minimal; see FIG. 15.

Figure 16:
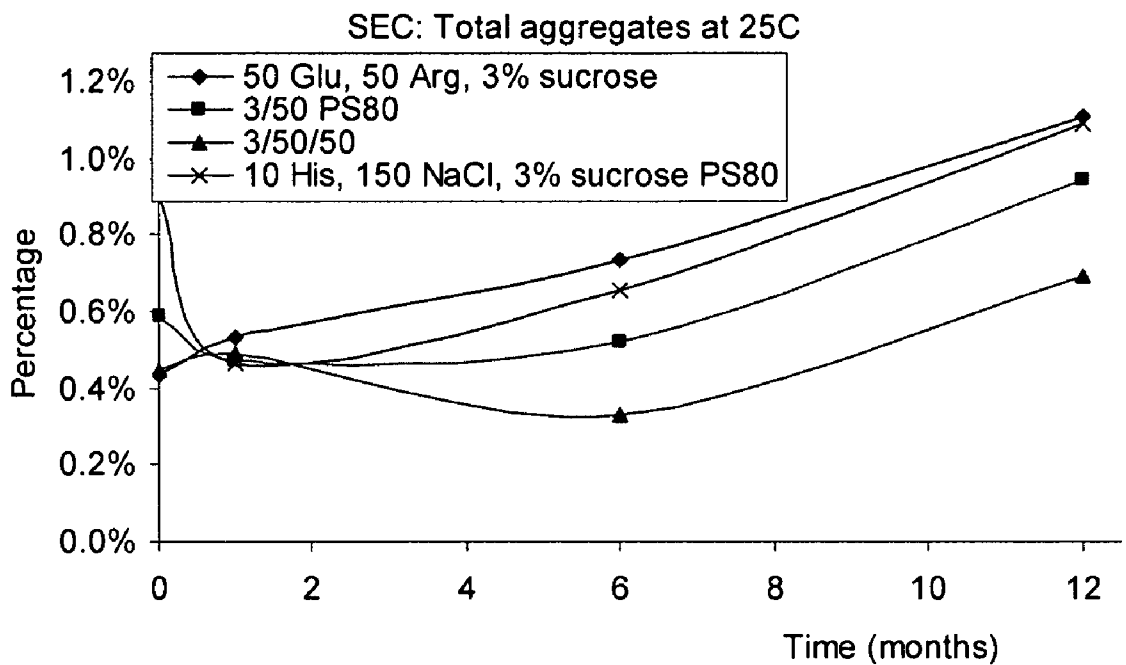
FIG. 16 illustrates total aggregation observed at 25° C. with a protein concentration of 50 mg/mL as measured by SEC-HPLC.
Figure 17:
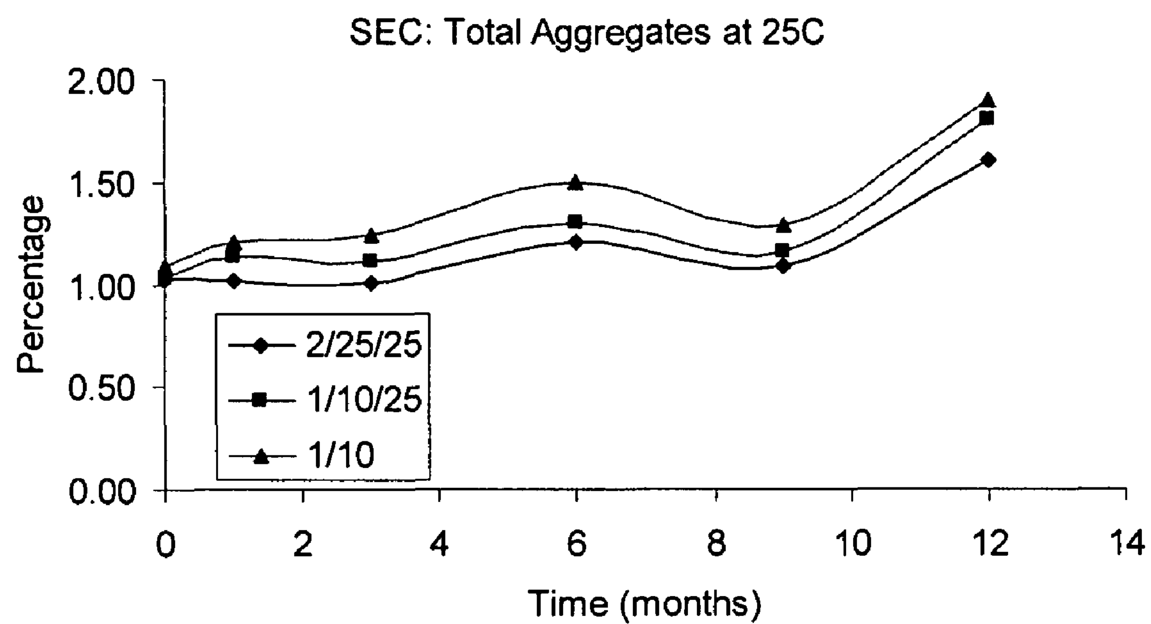
FIG. 17 illustrates total aggregation observed at 25° C. with a protein concentration of 50 mg/mL as measured by SEC-HPLC.

Minimal aggregation of mAb4 observed after storage at 25° C. for 12 months in formulations of 3/50/50 or 2/25/25 compared with other formulations tested; see FIGS. 16 and 17.

Figure 18:
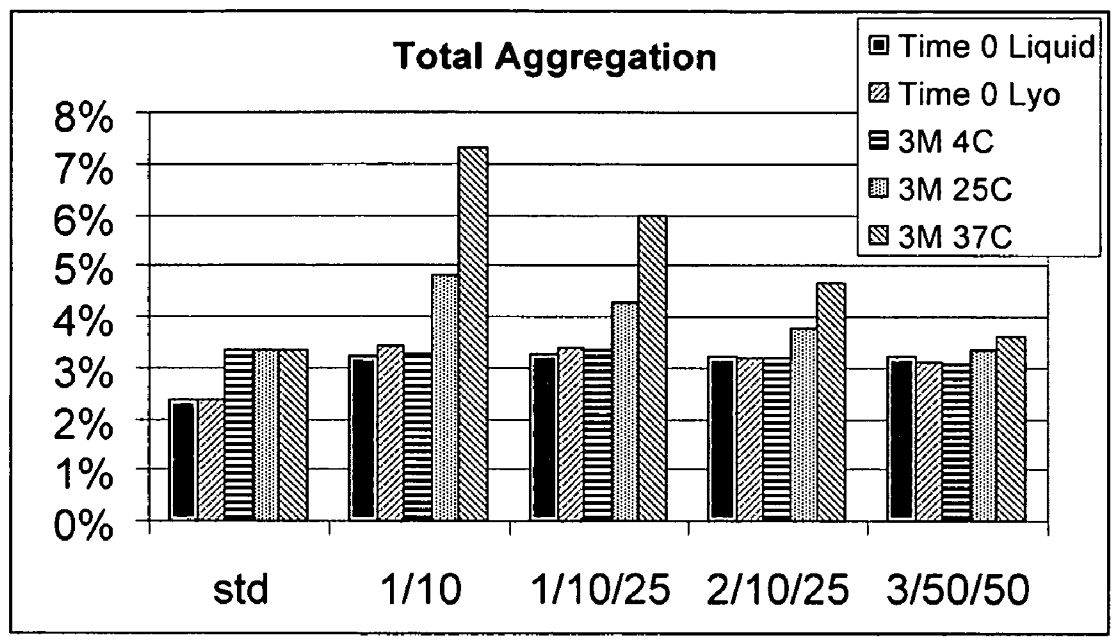
FIG. 18 illustrates the change in total aggregation at various temperature over three months of storage at 50 mg/mL in lyophilized form as measured by SEC-HPLC.
Figure 19:
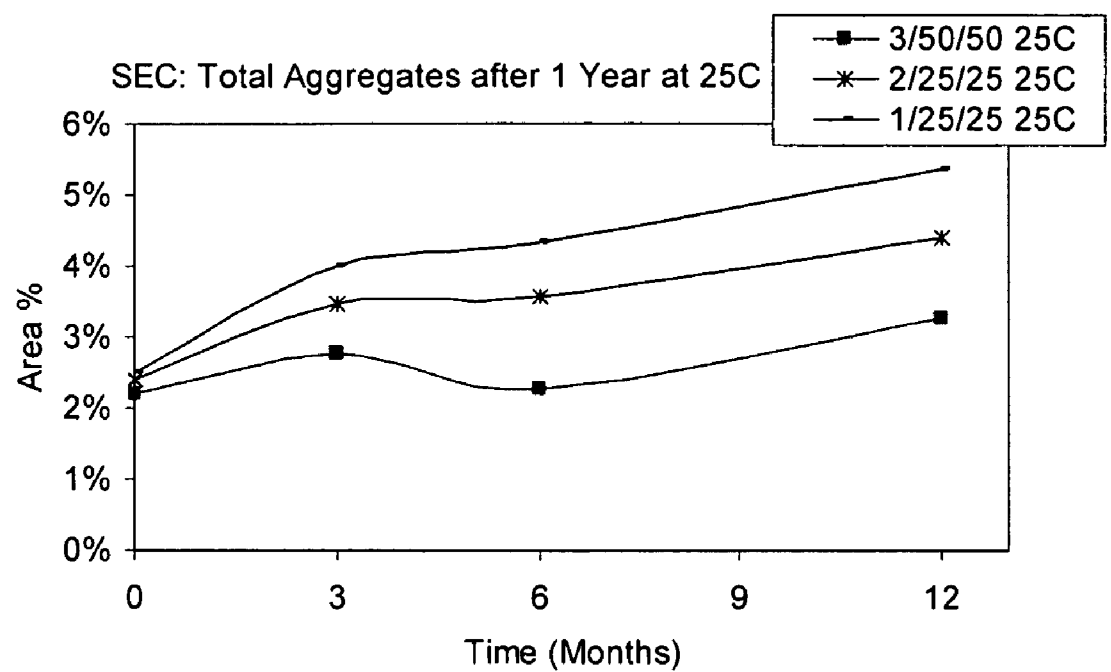
FIG. 19 illustrates total aggregation at 50 mg/mL in lyophilized form as measured by SEC-HPLC.

No aggregation was observed in a lyophilized formulation of 3% sucrose, 50 mM histidine, 50 mM arginine, pH 6.0 at 25° C. in mAb2 (FIG. 18) or mAb3 (FIG. 19). Aggregation increased significantly in other formulations tested.

EXAMPLE 15

Variants

Mutant 1B20 sequences were designed and libraries were generated and screened for 1B20 derivatives. Library optimizations were conducted generally in accordance with U.S. Pat. No. 7,117,096. The libraries were then screened and panned to identify variants with PCSK9-binding. Anti-PCSK9 antibody molecules were identified and are disclosed herein as SEQ ID NOs: 45-96. The following table summarizes the Kd data obtained exhibited by the antibodies from Biacore® analyses.

TABLE 7

| Ab ID | Comprising VH | Kd (nM) |
|---|---|---|
| A6 | SEQ ID NO: 45 | 1.39 |
| G3 | SEQ ID NO: 46 | 1.53 |
| G5 | SEQ ID NO: 47 | 1.65 |
| B2 | SEQ ID NO: 48 | 2.21 |
| E2 | SEQ ID NO: 49 | 2.62 |
| G4 | SEQ ID NO: 50 | 2.90 |
| F4 | SEQ ID NO: 51 | 3.14 |
| B9 | SEQ ID NO: 52 | 3.81 |
| C3 | SEQ ID NO: 53 | 4.50 |
| F2 | SEQ ID NO: 54 | 1.01 |
| F7 | SEQ ID NO: 55 | 1.26 |
| A7 | SEQ ID NO: 56 | 1.28 |
| G8 | SEQ ID NO: 57 | 1.51 |
| H4 | SEQ ID NO: 58 | 1.52 |
| D5 | SEQ ID NO: 59 | 1.60 |
| D4 | SEQ ID NO: 60 | 1.91 |
| B4 | SEQ ID NO: 61 | 2.01 |
| H1 | SEQ ID NO: 62 | 2.01 |
| G2 | SEQ ID NO: 63 | 2.11 |
| A1 | SEQ ID NO: 64 | 2.15 |
| A4 | SEQ ID NO: 65 | 2.15 |
| C2 | SEQ ID NO: 66 | 2.25 |
| H5 | SEQ ID NO: 67 | 2.41 |
| F6 | SEQ ID NO: 68 | 2.68 |
| B6 | SEQ ID NO: 69 | 2.88 |
| B1 | SEQ ID NO: 70 | 3.73 |
| F1 | SEQ ID NO: 71 | 3.47 |
| A8 | SEQ ID NO: 72 | 1.19 |
| B3 | SEQ ID NO: 73 | 1.21 |
| F8 | SEQ ID NO: 74 | 1.35 |
| H8 | SEQ ID NO: 75 | 1.35 |
| B5 | SEQ ID NO: 76 | 1.36 |
| E1 | SEQ ID NO: 77 | 1.36 |
| E8 | SEQ ID NO: 78 | 1.62 |
| C1 | SEQ ID NO: 79 | 1.65 |
| H3 | SEQ ID NO: 80 | 1.89 |
| A9 | SEQ ID NO: 81 | 1.95 |
| G7 | SEQ ID NO: 82 | 2.05 |

TABLE 7-continued

| Ab ID | Comprising VH | Kd (nM) |
|---|---|---|
| C6 | SEQ ID NO: 83 | 2.10 |
| G6 | SEQ ID NO: 84 | 2.20 |
| E4 | SEQ ID NO: 85 | 2.38 |
| F5 | SEQ ID NO: 86 | 2.41 |
| C7 | SEQ ID NO: 87 | 2.53 |
| E3 | SEQ ID NO: 88 | 2.62 |
| D3 | SEQ ID NO: 89 | 2.68 |
| D8 | SEQ ID NO: 90 | 3.21 |
| C8 | SEQ ID NO: 91 | 3.73 |
| E5 | SEQ ID NO: 92 | 4.22 |
| B8 | SEQ ID NO: 93 | 4.47 |
| H7 | SEQ ID NO: 94 | 4.90 |
| A5 | SEQ ID NO: 95 | 6.81 |
| A3 | SEQ ID NO: 96 | 7.93 |

Additional site-directed mutant variants of 1B20 were generated (mutations in the heavy chain) and are disclosed herein as SEQ ID NOs: 102-107. Kds of site-directed mutant variants of 1B20 Fabs were determined using a Bio-Rad ProteOn; with affinity being measured against human PCSK9-V5-His. The methodologies for measuring Fab affinities are essentially the same as previously described for Biacore®.

TABLE 8

| Ab ID | Comprising VH | KD (nM) |
|---|---|---|
| N59K | SEQ ID NO: 102 | 0.013 |
| N59Q | SEQ ID NO: 103 | 0.117 |
| N59R | SEQ ID NO: 104 | 0.049 |
| W101A | SEQ ID NO: 105 | 1.37 |
| W101F | SEQ ID NO: 106 | 1.12 |
| W101Y | SEQ ID NO: 107 | 0.780 |

* Amino acid numbering begins with the first residue of FR1, immediately following signal peptide.

What is claimed is:

1. An isolated PCSK9-specific antagonist antibody or antigen-binding fragment thereof which comprises:

(a) a heavy chain variable region comprising CDR1, 2 and 3 domains; said CDR1 domain comprising the amino acid sequence set forth in SEQ ID NO: 13; said CDR2 domain comprising the amino acid sequence set forth in SEQ ID NO: 15; and said CDR3 domain comprising the amino acid sequence set forth in SEQ ID NO: 17; and (b) a light chain variable region comprising CDR1, 2 and 3 domains; said CDR1 domain comprising the amino acid sequence set forth in SEQ ID NO: 3; said CDR2 domain comprising the amino acid sequence set forth in SEQ ID NO: 5, and said CDR3 domain comprising the amino acid sequence set forth in SEQ ID NO: 7;

wherein said PCSK9-specific antagonist antibody or fragment antagonizes PCSK9-mediated inhibition of cellular LDL uptake.

2. The PCSK9-specific antagonist antibody or antigen-binding fragment thereof Of claim 1 wherein the CDR1, 2 and 3 domains are in a human germline variable region in the respective CDR1, 2 and 3 regions thereof.

3. The PCSK9-specific antagonist antibody or antigen-binding fragment thereof of claim 1 that binds to human PCSK9 with an equilibrium dissociation constant of less than 1200 nM,

4. The PCSK9-specific antagonist antibody or antigen-binding fragment thereof of claim 1 that antagonizes PCSK9-mediated inhibition of cellular LDL uptake at an $IC_{50}$ of less than 500 nM.

5. The PCSK9-specific antagonist antibody or antigen-binding fragment thereof of claim 1 that antagonizes PCSK9-mediated inhibition of cellular uptake by at least 20%.

6. The PCSK9-specific antagonist antibody or antigen-binding fragment thereof of claim 1 which comprises a heavy chain variable region comprising the amino acid sequence set forth in SEQ ID NO: 11 and/or a light chain variable region comprising the amino acid sequence set forth in SEQ ID NO: 27.

7. The PCSK9-specific antagonist antibody or antigen-binding fragtherit thereof of claim 1 which comprises a heavy chain having constant immunoglobulin sequence comprising the amino acid sequence set forth in SEQ ID NO: 24,

8. An isolated PCSK9-specific antagonist antibody or antigen-binding fragment thereof which comprises:

(a) a light chain comprising the amino acid sequence set forth in SEQ ID NO: 26; and (b) a heavy chain comprising the amino acid sequence set forth in SEQ ID NO: 25;

wherein said PCSK9-specific antagonist antibody or fragment antagonizes PCSK9-mediated inhibition of cellular LDL uptake.

9. An isolated PCSK9-specific antagonist antibody or antigen-binding fragment thereof which comprises:

(a) a heavy chain variable region comprising CDR1, 2 and 3 domains; said CDR1 domain comprising the amino acid sequence set forth in SEQ ID NO: 37; said CDR2 domain comprising the amino acid sequence set forth in SEQ ID NO: 38; and said CDR3 domain comprising the amino acid sequence set forth in SEQ ID NO: 39; and a light chain variable region comprising COR1, 2 and 3 domains; said CDR1 domain comprising the amino acid sequence set forth in SEQ ID NO: 40; said CDR2 domain comprising the amino acid sequence set forth in SEQ ID NO: 41, and said CDR3 domain comprising the amino acid sequence set forth in SEQ ID NO: 42;

(b) a heavy chain variable region comprising CDR1, 2 and 3 domains; said CDR1 domain compriing the amino acid sequence set forth in SEQ ID NO: 37; said CDR2 domain comprising the amino acid sequence set forth in SEQ ID NO: 97; and said CDR3 domain comprising the amino acid sequence set forth in SEQ ID NO: 98; and a light chain variable region comprising CDR1, 2 and 3 domains; said CDR1 domain comprising the amino acid sequence set forth in SEQ ID NO: 99; said CDR2 domain comprising the amino acid sequence set forth in SEQ ID NO: 100, and said CDR3 domain comprising the amino acid sequence set forth in SEQ ID NO: 101; or (c) a heavy chain variable region comprising the amino acid sequence set forth in any one of SEQ ID NOs: 45-96 or 102-107 and a light chain variable region comprising the amino acid sequence set forth in SEQ ID NO:27;

wherein said PCSK9-specific antagonist antibody or fragment antagonizes PCSK9-mediated inhibition of cellular LDL uptake.

10. A composition comprising the PCSK9-specific antagonist antibody or antigen-binding fragment thereof of claim 1 and a pharmaceutically acceptable carrier.

11. A composition comprising the PCSK9-specific antagonist antibody or antigen-binding fragment thereof of claim 1 and a further therapeutic drug.

12. The Composition of claim 11 wherein the further therapeutic drug is a cholesterol absorption inhibitor or a cholesterol synthesis inhibitor.

13. A composition comprising the PCSK9-specific antagonist antibody or antigen-binding fragment thereof of claim 9 and a pharmaceutically acceptable carrier.

14. An isolated host cell or population of host cells in vitro or in situ comprising a PCSK9-specific antagonist antibody or antigen-binding fragment thereof of claim 1.

15. The host cell of claim 14 which is a *Pichia* cellor a Chinese hamster ovary cell.

16. An isolated host cell or population of host cells in vitro or in situ comprising a PCSK9-specific antagonist antibody or antigen-binding fragment thereof of claim 9.

17. The host cell of claim 16 which is a *Pichia* cell or a Chinese hamster ovary cell.

18. A method for lowering plasma low density lipoprotein level in a patient which comprises administering the PCSK9-specific antagonist antibody or antigen-binding fragment thereof of claim 1 to the patient.

19. The method of claim 18 wherein the patient is administered a further therapeutic drug.

20. The method of claim 19 wherein the further therapeutic drug is acholesterol absorption inhibitor or a cholesterol synthesis inhibitor.

21. A method for treating a medical condition mediated by PCSK9 activity in a patient comprising administering a therapeutically effective amount of PCSK9-specific antagonist antibody or antigen-binding fragment thereof of claim 1 to the patient.

22. The method of claim 21 wherein the medical condition is hypercholesterolemia, coronary heart disease, metabolic syndrome or acute coronary syndrome.

* * * * *

SEQUENCE LISTING

```
<160> NUMBER OF SEQ ID NOS: 109

<210> SEQ ID NO 1
<211> LENGTH: 220
<212> TYPE: PRT
<213> ORGANISM: Artificial Sequence
<220> FEATURE:
<223> OTHER INFORMATION: LC; 1B20

<400> SEQUENCE: 1

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Ser Phe Pro Ile Thr Phe Gly Gln Gly Thr Lys Val Glu Ile
            100                 105                 110
```

```
Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Ala
    210                 215                 220


<210> SEQ ID NO 2
<211> LENGTH: 660
<212> TYPE: DNA
<213> ORGANISM: Artificial Sequence
<220> FEATURE:
<223> OTHER INFORMATION: LC; 1B20

<400> SEQUENCE: 2

gatatcgtga tgacccagag cccggatagc ctggcggtga gcctgggcga acgtgcgacc     60

attaactgca gaagcagcca gtctgttctt tattcttcta acaataagaa ttatctggct    120

tggtaccagc agaaaccagg tcagccgccg aaactattaa tttattgggc ttctactcgt    180

gaaagcgggg tcccggatcg ttttagcggc tctggatccg gcactgattt taccctgacc    240

atttcgtccc tgcaagctga agacgtggcg gtgtattatt gccagcagta ttcttctttt    300

cctattacct ttggccaggg tacgaaagtt gaaattaaac gtacggtggc tgctccgagc    360

gtgtttattt ttccgccgag cgatgaacaa ctgaaaagcg gcacggcgag cgtggtgtgc    420

ctgctgaaca acttttatcc gcgtgaagcg aaagttcagt ggaaagtaga caacgcgctg    480

caaagcggca acagccagga aagcgtgacc gaacaggata gcaaagatag cacctattct    540

ctgagcagca ccctgaccct gagcaaagcg gattatgaaa aacataaagt gtatgcgtgc    600

gaagtgaccc atcaaggtct gagcagcccg gtgactaaat cttttaatcg tggcgaggcc    660


<210> SEQ ID NO 3
<211> LENGTH: 17
<212> TYPE: PRT
<213> ORGANISM: Artificial Sequence
<220> FEATURE:
<223> OTHER INFORMATION: VL CDR1; 1B20

<400> SEQUENCE: 3

Arg Ser Ser Gln Ser Val Leu Tyr Ser Ser Asn Asn Lys Asn Tyr Leu
 1               5                  10                  15

Ala


<210> SEQ ID NO 4
<211> LENGTH: 51
<212> TYPE: DNA
<213> ORGANISM: Artificial Sequence
<220> FEATURE:
<223> OTHER INFORMATION: VL CDR1; 1B20

<400> SEQUENCE: 4

agaagcagcc agtctgttct ttattcttct aacaataaga attatctggc t              51
```

<210> SEQ ID NO 5
<211> LENGTH: 11
<212> TYPE: PRT
<213> ORGANISM: Artificial Sequence
<220> FEATURE:
<223> OTHER INFORMATION: VL CDR2; 1B20

<400> SEQUENCE: 5

```
Leu Leu Ile Tyr Trp Ala Ser Thr Arg Glu Ser
 1               5                  10
```

<210> SEQ ID NO 6
<211> LENGTH: 33
<212> TYPE: DNA
<213> ORGANISM: Artificial Sequence
<220> FEATURE:
<223> OTHER INFORMATION: VL CDR2; 1B20

<400> SEQUENCE: 6

```
ctattaattt attgggcttc tactcgtgaa agc                                  33
```

<210> SEQ ID NO 7
<211> LENGTH: 8
<212> TYPE: PRT
<213> ORGANISM: Artificial Sequence
<220> FEATURE:
<223> OTHER INFORMATION: VL CDR3; 1B20

<400> SEQUENCE: 7

```
Gln Gln Tyr Ser Ser Phe Pro Ile
 1               5
```

<210> SEQ ID NO 8
<211> LENGTH: 24
<212> TYPE: DNA
<213> ORGANISM: Artificial Sequence
<220> FEATURE:
<223> OTHER INFORMATION: VL CDR3; 1B20

<400> SEQUENCE: 8

```
cagcagtatt cttcttttcc tatt                                            24
```

<210> SEQ ID NO 9
<211> LENGTH: 243
<212> TYPE: PRT
<213> ORGANISM: Artificial Sequence
<220> FEATURE:
<223> OTHER INFORMATION: FD CHAIN; 1B20

<400> SEQUENCE: 9

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Lys Pro Leu Phe Asp Ile Trp Gly Gln Gly
            100                 105                 110
```

```
Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Glu Phe Glu
    210                 215                 220

Gln Lys Leu Ile Ser Glu Glu Asp Leu Asn Gly Ala Pro His His His
225                 230                 235                 240

His His His
```

<210> SEQ ID NO 10
<211> LENGTH: 729
<212> TYPE: DNA
<213> ORGANISM: Artificial Sequence
<220> FEATURE:
<223> OTHER INFORMATION: FD CHAIN; 1B20

<400> SEQUENCE: 10

```
caggtgcaat tggttcagag cggcgcggaa gtgaaaaaac cgggcgaaag cctgaaaatt     60

agctgcaaag gttccggata ttcctttact aattattgga tttcttgggt gcgccagatg    120

cctgggaagg gtctcgagtg gatgggcatt atctatccgg gtgatagcta taccaattat    180

tctccgagct ttcagggcca ggtgaccatt agcgcggata aaagcattag caccgcgtat    240

cttcaatgga gcagcctgaa agcgagcgat acggccatgt attattgcgc gcgtgattat    300

tggtataagc ctctttttga tatttggggc caaggcaccc tggtgacggt tagctcagcg    360

tcgaccaaag gtccaagcgt gtttccgctg gctccgagca gcaaaagcac cagcggcggc    420

acggctgccc tgggctgcct ggttaaagat tatttcccgg aaccagtcac cgtgagctgg    480

aacagcgggg cgctgaccag cggcgtgcat acctttccgg cggtgctgca aagcagcggc    540

ctgtatagcc tgagcagcgt tgtgaccgtg ccgagcagca gcttaggcac tcagacctat    600

atttgcaacg tgaaccataa accgagcaac accaaagtgg ataaaaaagt ggaaccgaaa    660

agcgaattcg agcagaagct gatctctgag gaggatctga acggcgcgcc gcaccatcat    720

caccatcac                                                            729
```

<210> SEQ ID NO 11
<211> LENGTH: 119
<212> TYPE: PRT
<213> ORGANISM: Artificial Sequence
<220> FEATURE:
<223> OTHER INFORMATION: VH; 1B20

<400> SEQUENCE: 11

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
```

-continued

```
        35                  40                  45

Gly Ile Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Lys Pro Leu Phe Asp Ile Trp Gly Gln Gly
            100                 105                 110

Thr Leu Val Thr Val Ser Ser
        115


<210> SEQ ID NO 12
<211> LENGTH: 357
<212> TYPE: DNA
<213> ORGANISM: Artificial Sequence
<220> FEATURE:
<223> OTHER INFORMATION: VH; 1B20

<400> SEQUENCE: 12

caggtgcaat tggttcagag cggcgcggaa gtgaaaaaac cgggcgaaag cctgaaaatt     60

agctgcaaag gttccggata ttcctttact aattattgga tttcttgggt gcgccagatg    120

cctgggaagg gtctcgagtg gatgggcatt atctatccgg gtgatagcta taccaattat    180

tctccgagct ttcagggcca ggtgaccatt agcgcggata aaagcattag caccgcgtat    240

cttcaatgga gcagcctgaa agcgagcgat acggccatgt attattgcgc gcgtgattat    300

tggtataagc ctctttttga tatttggggc caaggcaccc tggtgacggt tagctca       357


<210> SEQ ID NO 13
<211> LENGTH: 10
<212> TYPE: PRT
<213> ORGANISM: Artificial Sequence
<220> FEATURE:
<223> OTHER INFORMATION: VH CDR1; 1B20

<400> SEQUENCE: 13

Gly Tyr Ser Phe Thr Asn Tyr Trp Ile Ser
 1               5                  10


<210> SEQ ID NO 14
<211> LENGTH: 30
<212> TYPE: DNA
<213> ORGANISM: Artificial Sequence
<220> FEATURE:
<223> OTHER INFORMATION: VH CDR1; 1B20

<400> SEQUENCE: 14

ggatattcct ttactaatta ttggatttct                                      30


<210> SEQ ID NO 15
<211> LENGTH: 20
<212> TYPE: PRT
<213> ORGANISM: Artificial Sequence
<220> FEATURE:
<223> OTHER INFORMATION: VH CDR2; 1B20

<400> SEQUENCE: 15

Trp Met Gly Ile Ile Tyr Pro Gly Asp Ser Tyr Thr Asn Tyr Ser Pro
 1               5                  10                  15

Ser Phe Gln Gly
            20
```

<210> SEQ ID NO 16
<211> LENGTH: 60
<212> TYPE: DNA
<213> ORGANISM: Artificial Sequence
<220> FEATURE:
<223> OTHER INFORMATION: VH CDR2; 1B20

<400> SEQUENCE: 16
tggatgggca ttatctatcc gggtgatagc tataccaatt attctccgag ctttcagggc 60

<210> SEQ ID NO 17
<211> LENGTH: 10
<212> TYPE: PRT
<213> ORGANISM: Artificial Sequence
<220> FEATURE:
<223> OTHER INFORMATION: VH CDR3; 1B20

<400> SEQUENCE: 17

Asp Tyr Trp Tyr Lys Pro Leu Phe Asp Ile
1 5 10

<210> SEQ ID NO 18
<211> LENGTH: 30
<212> TYPE: DNA
<213> ORGANISM: Artificial Sequence
<220> FEATURE:
<223> OTHER INFORMATION: VH CDR3; 1B20

<400> SEQUENCE: 18
gattattggt ataagcctct ttttgatatt 30

<210> SEQ ID NO 19
<211> LENGTH: 6
<212> TYPE: PRT
<213> ORGANISM: Artificial Sequence
<220> FEATURE:
<223> OTHER INFORMATION: INTERNAL PROCESSING SITE

<400> SEQUENCE: 19

Ser Ser Val Phe Ala Gln
1 5

<210> SEQ ID NO 20
<211> LENGTH: 6
<212> TYPE: PRT
<213> ORGANISM: Artificial Sequence
<220> FEATURE:
<223> OTHER INFORMATION: INTERNAL PROCESSING SITE

<400> SEQUENCE: 20

Ser Ile Pro Trp Asn Leu
1 5

<210> SEQ ID NO 21
<211> LENGTH: 330
<212> TYPE: PRT
<213> ORGANISM: Artificial Sequence
<220> FEATURE:
<223> OTHER INFORMATION: CONTAINS FC DOMAIN OF IGG1

<400> SEQUENCE: 21

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser

```
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 22
<211> LENGTH: 326
<212> TYPE: PRT
<213> ORGANISM: Artificial Sequence
<220> FEATURE:
<223> OTHER INFORMATION: CONTAINS FC DOMAIN OF IGG2

<400> SEQUENCE: 22

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80
```

```
Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 23
<211> LENGTH: 327
<212> TYPE: PRT
<213> ORGANISM: Artificial Sequence
<220> FEATURE:
<223> OTHER INFORMATION: CONTAINS FC DOMAIN OF IGG4

<400> SEQUENCE: 23

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110
```

```
Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 24
<211> LENGTH: 326
<212> TYPE: PRT
<213> ORGANISM: Artificial Sequence
<220> FEATURE:
<223> OTHER INFORMATION: CONTAINS FC DOMAIN OF IGG2M4

<400> SEQUENCE: 24

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
```

```
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 25
<211> LENGTH: 445
<212> TYPE: PRT
<213> ORGANISM: Artificial Sequence
<220> FEATURE:
<223> OTHER INFORMATION: 1B20 IgG2m4 Heavy Chain

<400> SEQUENCE: 25

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Lys Pro Leu Phe Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Thr Ser
            180                 185                 190
```

```
Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 26
<211> LENGTH: 220
<212> TYPE: PRT
<213> ORGANISM: Artificial Sequence
<220> FEATURE:
<223> OTHER INFORMATION: 1B20 IgG Light Chain

<400> SEQUENCE: 26

Asp Ile Val Met Thr Gln Ser Pro Asp Ser Leu Ala Val Ser Leu Gly
 1               5                  10                  15

Glu Arg Ala Thr Ile Asn Cys Arg Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Ser Phe Pro Ile Thr Phe Gly Gln Gly Thr Lys Val Glu Ile
            100                 105                 110
```

```
Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 27
<211> LENGTH: 114
<212> TYPE: PRT
<213> ORGANISM: Artificial Sequence
<220> FEATURE:
<223> OTHER INFORMATION: VL; 1B20

<400> SEQUENCE: 27

Asp Ile Val Met Thr Gln Ser Pro Asp Ser Leu Ala Val Ser Leu Gly
 1               5                  10                  15

Glu Arg Ala Thr Ile Asn Cys Arg Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Ser Phe Pro Ile Thr Phe Gly Gln Gly Thr Lys Val Glu Ile
            100                 105                 110

Lys Arg


<210> SEQ ID NO 28
<211> LENGTH: 342
<212> TYPE: DNA
<213> ORGANISM: Artificial Sequence
<220> FEATURE:
<223> OTHER INFORMATION: VL; 1B20

<400> SEQUENCE: 28

gatatcgtga tgacccagag cccggatagc ctggcggtga gcctgggcga acgtgcgacc      60

attaactgca gaagcagcca gtctgttctt tattcttcta acaataagaa ttatctggct     120

tggtaccagc agaaaccagg tcagccgccg aaactattaa tttattgggc ttctactcgt     180

gaaagcgggg tcccggatcg ttttagcggc tctggatccg gcactgattt taccctgacc     240

atttcgtccc tgcaagctga agacgtggcg gtgtattatt gccagcagta ttcttctttt     300

cctattacct ttggccaggg tacgaaagtt gaaattaaac gt                        342


<210> SEQ ID NO 29
<211> LENGTH: 1335
<212> TYPE: DNA
```

<213> ORGANISM: Artificial Sequence
<220> FEATURE:
<223> OTHER INFORMATION: 1B20 IgG2m4 Heavy Chain

<400> SEQUENCE: 29

```
caggtgcaat tggttcagag cggcgcggaa gtgaaaaaac cgggcgaaag cctgaaaatt     60
agctgcaaag gttccggata ttcctttact aattattgga tttcttgggt gcgccagatg    120
cctgggaagg gtctcgagtg gatgggcatt atctatccgg gtgatagcta taccaattat    180
tctccgagct ttcagggcca ggtgaccatt agcgcggata aaagcattag caccgcgtat    240
cttcaatgga gcagcctgaa agcgagcgat acggccatgt attattgcgc gcgtgattat    300
tggtataagc ctctttttga tatttggggc caaggcaccc tggtgacggt tagctcagca    360
tccaccaagg gcccatccgt cttccccctg gcgccctgct ccaggagcac ctccgagagc    420
acagccgccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg acctccagca actttggcac gcagacctac    600
acctgcaacg tagatcacaa gcccagcaac accaaggtgg acaagacagt tgagcggaaa    660
tgctgcgtgg agtgcccacc atgcccagca cctccagtgg ccggaccatc agtcttcctg    720
ttccccccaa aacccaagga cactctcatg atctcccgga cccctgaggt cacgtgcgtg    780
gtggtggacg tgagccagga agaccccgag gtccagttca actggtacgt ggatggcgtg    840
gaggtgcata atgccaagac aaagccgcgg gaggagcagt tcaacagcac gttccgtgtg    900
gtcagcgtcc tcaccgtcct gcaccaggac tggctgaacg gcaaggagta caagtgcaag    960
gtctccaaca aaggcctccc gtcctccatc gagaaaacca tctccaaaac caaagggcag   1020
ccccgagagc cacaggtgta caccctgccc ccatcccggg aggagatgac caagaaccag   1080
gtcagcctga cctgcctggt caaaggcttc taccccagcg acatcgccgt ggagtgggag   1140
agcaatgggc agccggagaa caactacaag accacgcctc ccatgctgga ctccgacggc   1200
tccttcttcc tctacagcaa gctaaccgtg gacaagagca ggtggcagca ggggaatgtc   1260
ttctcatgct ccgtgatgca tgaggctctg cacaaccact acacacagaa gagcctctcc   1320
ctgtctcctg gtaaa                                                    1335
```

<210> SEQ ID NO 30
<211> LENGTH: 660
<212> TYPE: DNA
<213> ORGANISM: Artificial Sequence
<220> FEATURE:
<223> OTHER INFORMATION: 1B20 IgG Light Chain

<400> SEQUENCE: 30

```
gatatcgtga tgacccagag cccggatagc ctggcggtga gcctgggcga acgtgcgacc     60
attaactgca gaagcagcca gtctgttctt tattcttcta acaataagaa ttatctggct    120
tggtaccagc agaaaccagg tcagccgccg aaactattaa tttattgggc ttctactcgt    180
gaaagcgggg tcccggatcg ttttagcggc tctggatccg gcactgattt taccctgacc    240
atttcgtccc tgcaagctga agacgtggcg gtgtattatt gccagcagta ttcttctttt    300
cctattacct ttggccaggg tacgaaagtt gaaattaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
```

ctcagcagca ccctgacgct gagcaaagca gactacgaga aacacaaagt ctacgcctgc 600
gaagtcaccc atcagggcct gagctcgccc gtcacaaaga gcttcaacag gggagagtgt 660

<210> SEQ ID NO 31
<211> LENGTH: 34
<212> TYPE: DNA
<213> ORGANISM: Artificial Sequence
<220> FEATURE:
<223> OTHER INFORMATION: Primer

<400> SEQUENCE: 31
acagatgcca gatgcgatat cgtgatgacc caga 34

<210> SEQ ID NO 32
<211> LENGTH: 36
<212> TYPE: DNA
<213> ORGANISM: PArtificial Sequence
<220> FEATURE:
<223> OTHER INFORMATION: Primer

<400> SEQUENCE: 32
tgcagccacc gtacgtttaa tttcaacttt cgtacc 36

<210> SEQ ID NO 33
<211> LENGTH: 36
<212> TYPE: DNA
<213> ORGANISM: Artificial Sequence
<220> FEATURE:
<223> OTHER INFORMATION: Primer

<400> SEQUENCE: 33
acaggtgtcc actcgcaggt gcaattggtt cagagc 36

<210> SEQ ID NO 34
<211> LENGTH: 36
<212> TYPE: DNA
<213> ORGANISM: Artificial Sequence
<220> FEATURE:
<223> OTHER INFORMATION: Primer

<400> SEQUENCE: 34
gcccttggtg gatgctgagc taaccgtcac cagggt 36

<210> SEQ ID NO 35
<211> LENGTH: 8539
<212> TYPE: DNA
<213> ORGANISM: Artificial Sequence
<220> FEATURE:
<223> OTHER INFORMATION: 1B20 IgG2m4 HC Plasmid

<400> SEQUENCE: 35
cgatagattg tcgcacctga ttgcccgaca ttatcgcgag cccatttata cccatataaa 60
tcagcatcca tgttggaatt taatcgcggc ctcgagcaag acgtttcccg ttgaatatgg 120
ctcataacac cccttgtatt actgtttatg taagcagaca gttttattgt tcatgatgat 180
atatttttat cttgtgcaat gtaacatcag agattttgag acacaacgtg gctttccccc 240
cccccccatt attgaagcat ttatcagggt tattgtctca tgagcggata catatttgaa 300
tgtatttaga aaaataaaca aataggggtt ccgcgcacat ttccccgaaa agtgccacct 360
gacgtctaag aaaccattat tatcatgaca ttaacctata aaaataggcg tatcacgagg 420
ccctttcgtc tcgcgcgttt cggtgatgac ggtgaaaacc tctgacacat gcagctcccg 480
gagacggtca cagcttgtct gtaagcggat gccgggagca gacaagcccg tcagggcgcg 540

-continued

```
tcagcgggtg ttggcgggtg tcggggctgg cttaactatg cggcatcaga gcagattgta    600
ctgagagtgc accatatgct taattaacgc ggggcagtgc atgtaatccc ttcagttggt    660
tggtacaact tgccaactgg gccctgttcc acatgtgaca cgggggggga ccaaacacaa    720
aggggttctc tgactgtagt tgacatcctt ataaatggat gtgcacattt gccaacactg    780
agtggctttc atcctggagc agactttgca gtctgtggac tgcaacacaa cattgccttt    840
atgtgtaact cttggctgaa gctcttacac caatgctggg ggacatgtac ctcccagggg    900
cccaggaaga ctacgggagg ctacaccaac gtcaatcaga ggggcctgtg tagctaccga    960
taagcggacc ctcaagaggg cattagcaat agtgtttata aggccccctt gttaacccta   1020
aacgggtagc atatgcttcc cgggtagtag tatatactat ccagactaac cctaattcaa   1080
tagcatatgt tacccaacgg gaagcatatg ctatcgaatt agggttagta aaagggtcct   1140
aaggaacagc gatatctccc accccatgag ctgtcacggt tttatttaca tggggtcagg   1200
attccacgag ggtagtgaac cattttagtc acaagggcag tggctgaaga tcaaggagcg   1260
ggcagtgaac tctcctgaat cttcgcctgc ttcttcattc tccttcgttt agctaataga   1320
ataactgctg agttgtgaac agtaaggtgt atgtgaggtg ctcgaaaaca aggtttcagg   1380
tgacgccccc agaataaaat ttggacgggg ggttcagtgg tggcattgtg ctatgacacc   1440
aatataaccc tcacaaaccc cttgggcaat aaatactagt gtaggaatga aacattctga   1500
atatctttaa caatagaaat ccatggggtg gggacaagcc gtaaagactg gatgtccatc   1560
tcacacgaat ttatggctat gggcaacaca taatcctagt gcaatatgat actggggtta   1620
ttaagatgtg tcccaggcag ggaccaagac aggtgaacca tgttgttaca ctctatttgt   1680
aacaagggga aagagagtgg acgccgacag cagcggactc cactggttgt ctctaacacc   1740
cccgaaaatt aaacggggct ccacgccaat ggggcccata aacaaagaca agtggccact   1800
cttttttttg aaattgtgga gtgggggcac gcgtcagccc ccacacgccg ccctgcggtt   1860
ttggactgta aaataagggt gtaataactt ggctgattgt aaccccgcta accactgcgg   1920
tcaaaccact tgcccacaaa accactaatg gcaccccggg gaatacctgc ataagtaggt   1980
gggcgggcca agataggggc gcgattgctg cgatctggag gacaaattac acacacttgc   2040
gcctgagcgc caagcacagg gttgttggtc ctcatattca cgaggtcgct gagagcacgg   2100
tgggctaatg ttgccatggg tagcatatac tacccaaata tctggatagc atatgctatc   2160
ctaatctata tctgggtagc ataggctatc ctaatctata tctgggtagc atatgctatc   2220
ctaatctata tctgggtagt atatgctatc ctaatttata tctgggtagc ataggctatc   2280
ctaatctata tctgggtagc atatgctatc ctaatctata tctgggtagt atatgctatc   2340
ctaatctgta tccgggtagc atatgctatc ctaatagaga ttagggtagt atatgctatc   2400
ctaatttata tctgggtagc atatactacc caaatatctg gatagcatat gctatcctaa   2460
tctatatctg ggtagcatat gctatcctaa tctatatctg ggtagcatag gctatcctaa   2520
tctatatctg ggtagcatat gctatcctaa tctatatctg ggtagtatat gctatcctaa   2580
tttatatctg ggtagcatag gctatcctaa tctatatctg ggtagcatat gctatcctaa   2640
tctatatctg ggtagtatat gctatcctaa tctgtatccg ggtagcatat gctatcctca   2700
tgcatataca gtcagcatat gatacccagt agtagagtgg gagtgctatc ctttgcatat   2760
gccgccacct cccaaggggg cgtgaatttt cgctgcttgt ccttttcctg cggcgcgccg   2820
tttaaacatt taaatggatc cgcaccatat gcggtgtgaa ataccgcaca gatgcgtaag   2880
gagaaaatac cgcatcagat tggctattgg ccattgcata cgttgtatcc atatcataat   2940
```

-continued

```
atgtacattt atattggctc atgtccaaca ttaccgccat gttgacattg attattgact   3000

agttattaat agtaatcaat tacggggtca ttagttcata gcccatatat ggagttccgc   3060

gttacataac ttacggtaaa tggcccgcct ggctgaccgc ccaacgaccc ccgcccattg   3120

acgtcaataa tgacgtatgt tcccatagta acgccaatag ggactttcca ttgacgtcaa   3180

tgggtggagt atttacggta aactgcccac ttggcagtac atcaagtgta tcatatgcca   3240

agtacgcccc ctattgacgt caatgacggt aaatggcccg cctggcatta tgcccagtac   3300

atgaccttat gggactttcc tacttggcag tacatctacg tattagtcat cgctattacc   3360

atggtgatgc ggttttggca gtacatcaat gggcgtggat agcggtttga ctcacgggga   3420

tttccaagtc tccaccccat tgacgtcaat gggagtttgt tttggcacca aaatcaacgg   3480

gactttccaa aatgtcgtaa caactccgcc ccattgacgc aaatgggcgg taggcgtgta   3540

cggtgggagg tctatataag cagagctcgt ttagtgaacc gtcagatcgc ctggagacgc   3600

catccacgct gttttgacct ccatagaaga caccgggacc gatccagcct ccgcggccgg   3660

gaacggtgca ttggaacgcg gattccccgt gccaagagtg acgtaagtac cgcctataga   3720

gtctataggc ccaccccctt ggcttcttat gcatgctata ctgtttttgg cttggggtct   3780

atacaccccc gcttcctcat gttataggtg atggtatagc ttagcctata ggtgtgggtt   3840

attgaccatt attgaccact cccctattgg tgacgatact ttccattact aatccataac   3900

atggctcttt gccacaactc tctttattgg ctatatgcca atacactgtc cttcagagac   3960

tgacacggac tctgtatttt tacaggatgg ggtctcattt attatttaca aattcacata   4020

tacaacacca ccgtccccag tgcccgcagt ttttattaaa cataacgtgg gatctccacg   4080

cgaatctcgg gtacgtgttc cggacatggg ctcttctccg gtagcggcgg agcttctaca   4140

tccgagccct ggtcccatgc ctccagcggc tcatggtcgc tcggcagctc cttgctccta   4200

acagtggagg ccagacttag gcacagcaca atgcccacca ccaccagtgt gccgcacaag   4260

gccgtggcgg tagggtatgt gtctgaaaat gagcgtggag attgggctcg cacggctgac   4320

gcagatggaa gacttaaggc agcggcagaa gaagatgcag gcagctgagt tgttgtattc   4380

tgataagagt cagaggtaac tcccgttgcg gtgctgttaa cggtggaggg cagtgtagtc   4440

tgagcagtac tcgttgctgc cgcgcgcgcc accagacata atagctgaca gactaacaga   4500

ctgttccttt ccatgggtct tttctgcagt caccgtcctt gacacgaagc ttgccgccac   4560

catggaatgg agctgggtct ttctcttctt cctgtcagta actacaggtg tccactcgca   4620

ggtgcaattg gttcagagcg gcgcggaagt gaaaaaaccg ggcgaaagcc tgaaaattag   4680

ctgcaaaggt tccggatatt cctttactaa ttattggatt tcttgggtgc gccagatgcc   4740

tgggaagggt ctcgagtgga tgggcattat ctatccgggt gatagctata ccaattattc   4800

tccgagcttt cagggccagg tgaccattag cgcggataaa agcattagca ccgcgtatct   4860

tcaatggagc agcctgaaag cgagcgatac ggccatgtat tattgcgcgc gtgattattg   4920

gtataagcct ctttttgata tttggggcca aggcaccctg gtgacggtta gctcagcatc   4980

caccaagggc ccatccgtct tccccctggc gccctgctcc aggagcacct ccgagagcac   5040

agccgccctg ggctgcctgg tcaaggacta cttccccgaa ccggtgacgg tgtcgtggaa   5100

ctcaggcgcc ctgaccagcg gcgtgcacac cttcccggct gtcctacagt cctcaggact   5160

ctactccctc agcagcgtgg tgaccgtgac ctccagcaac tttggcacgc agacctacac   5220

ctgcaacgta gatcacaagc ccagcaacac caaggtggac aagacagttg agcggaaatg   5280

ctgcgtggag tgcccaccat gcccagcacc tccagtggcc ggaccatcag tcttcctgtt   5340
```

```
ccccccaaaa cccaaggaca ctctcatgat ctcccggacc cctgaggtca cgtgcgtggt   5400

ggtggacgtg agccaggaag accccgaggt ccagttcaac tggtacgtgg atggcgtgga   5460

ggtgcataat gccaagacaa agccgcggga ggagcagttc aacagcacgt tccgtgtggt   5520

cagcgtcctc accgtcctgc accaggactg gctgaacggc aaggagtaca agtgcaaggt   5580

ctccaacaaa ggcctcccgt cctccatcga gaaaaccatc tccaaaacca aagggcagcc   5640

ccgagagcca caggtgtaca ccctgccccc atcccgggag gagatgacca agaaccaggt   5700

cagcctgacc tgcctggtca aaggcttcta ccccagcgac atcgccgtgg agtgggagag   5760

caatgggcag ccggagaaca actacaagac cacgcctccc atgctggact ccgacggctc   5820

cttcttcctc tacagcaagc taaccgtgga caagagcagg tggcagcagg ggaatgtctt   5880

ctcatgctcc gtgatgcatg aggctctgca caaccactac acacagaaga gcctctccct   5940

gtctcctggt aaatgagcgg ccgcgatctg ctgtgccttc tagttgccag ccatctgttg   6000

tttgcccctc ccccgtgcct tccttgaccc tggaaggtgc cactcccact gtcctttcct   6060

aataaaatga ggaaattgca tcgcattgtc tgagtaggtg tcattctatt ctggggggtg   6120

gggtggggca gcacagcaag ggggaggatt gggaagacaa tagcaggcat gctggggatg   6180

cggtgggctc tatggccgct gagatctggc cgctgcggcc aggtgctgaa gaattgaccc   6240

ggttcctcct gggccagaaa gaagcaggca catccccttc tctgtgacac accctgtcca   6300

cgcccctggt tcttagttcc agccccactc ataggacact catagctcag gagggctccg   6360

ccttcaatcc cacccgctaa agtacttgga gcggtctctc cctccctcat cagcccacca   6420

aaccaaacct agcctccaag agtgggaaga aattaaagca agataggcta ttaagtgcag   6480

agggagagaa aatgcctcca acatgtgagg aagtaatgag agaaatcata gaatttcttc   6540

cgcttcctcg ctcactgact cgctgcgctc ggtcgttcgg ctgcggcgag cggtatcagc   6600

tcactcaaag gcggtaatac ggttatccac agaatcaggg gataacgcag gaaagaacat   6660

gtgagcaaaa ggccagcaaa aggccaggaa ccgtaaaaag gccgcgttgc tggcgttttt   6720

ccataggctc cgcccccctg acgagcatca caaaaatcga cgctcaagtc agaggtggcg   6780

aaacccgaca ggactataaa gataccaggc gtttccccct ggaagctccc tcgtgcgctc   6840

tcctgttccg accctgccgc ttaccggata cctgtccgcc tttctccctt cgggaagcgt   6900

ggcgctttct caatgctcac gctgtaggta tctcagttcg gtgtaggtcg ttcgctccaa   6960

gctgggctgt gtgcacgaac cccccgttca gcccgaccgc tgcgccttat ccggtaacta   7020

tcgtcttgag tccaacccgg taagacacga cttatcgcca ctggcagcag ccactggtaa   7080

caggattagc agagcgaggt atgtaggcgg tgctacagag ttcttgaagt ggtggcctaa   7140

ctacggctac actagaagga cagtatttgg tatctgcgct ctgctgaagc cagttacctt   7200

cggaaaaaga gttggtagct cttgatccgg caaacaaacc accgctggta gcggtggttt   7260

ttttgtttgc aagcagcaga ttacgcgcag aaaaaaagga tctcaagaag atcctttgat   7320

cttttctacg gggtctgacg ctcagtggaa cgaaaactca cgttaaggga ttttggtcat   7380

gagattatca aaaaggatct tcacctagat ccttttaaat taaaaatgaa gttttaaatc   7440

aatctaaagt atatatgagt aaacttggtc tgacagttac caatgcttaa tcagtgaggc   7500

acctatctca gcgatctgtc tatttcgttc atccatagtt gcctgactcc gggggggggg   7560

ggcgctgagg tctgcctcgt gaagaaggtg ttgctgactc ataccaggcc tgaatcgccc   7620

catcatccag ccagaaagtg agggagccac ggttgatgag agctttgttg taggtggacc   7680

agttggtgat tttgaacttt tgctttgcca cggaacggtc tgcgttgtcg ggaagatgcg   7740
```

```
tgatctgatc cttcaactca gcaaaagttc gatttattca acaaagccgc cgtcccgtca   7800

agtcagcgta atgctctgcc agtgttacaa ccaattaacc aattctgatt agaaaaactc   7860

atcgagcatc aaatgaaact gcaatttatt catatcagga ttatcaatac catatttttg   7920

aaaaagccgt ttctgtaatg aaggagaaaa ctcaccgagg cagttccata ggatggcaag   7980

atcctggtat cggtctgcga ttccgactcg tccaacatca atacaaccta ttaatttccc   8040

ctcgtcaaaa ataaggttat caagtgagaa atcaccatga gtgacgactg aatccggtga   8100

gaatggcaaa agcttatgca tttctttcca gacttgttca acaggccagc cattacgctc   8160

gtcatcaaaa tcactcgcat caaccaaacc gttattcatt cgtgattgcg cctgagcgag   8220

acgaaatacg cgatcgctgt taaaaggaca attacaaaca ggaatcgaat gcaaccggcg   8280

caggaacact gccagcgcat caacaatatt ttcacctgaa tcaggatatt cttctaatac   8340

ctggaatgct gttttcccgg ggatcgcagt ggtgagtaac catgcatcat caggagtacg   8400

gataaaatgc ttgatggtcg gaagaggcat aaattccgtc agccagttta gtctgaccat   8460

ctcatctgta acatcattgg caacgctacc tttgccatgt ttcagaaaca actctggcgc   8520

atcgggcttc ccatacaat                                                8539


<210> SEQ ID NO 36
<211> LENGTH: 9505
<212> TYPE: DNA
<213> ORGANISM: Artificial Sequence
<220> FEATURE:
<223> OTHER INFORMATION: 1B20 IgG LC Plasmid

<400> SEQUENCE: 36

cgatagattg tcgcacctga ttgcccgaca ttatcgcgag cccatttata cccatataaa     60

tcagcatcca tgttggaatt taatcgcggc ctcgagcaag acgtttcccg ttgaatatgg    120

ctcataacac cccttgtatt actgtttatg taagcagaca gttttattgt tcatgatgat    180

atatttttat cttgtgcaat gtaacatcag agattttgag acacaacgtg gctttccccc    240

cccccccatt attgaagcat ttatcagggt tattgtctca tgagcggata catatttgaa    300

tgtatttaga aaaataaaca aataggggtt ccgcgcacat ttccccgaaa agtgccacct    360

gacgtctaag aaaccattat tatcatgaca ttaacctata aaaataggcg tatcacgagg    420

ccctttcgtc tcgcgcgttt cggtgatgac ggtgaaaacc tctgacacat gcagctcccg    480

gagacggtca cagcttgtct gtaagcggat gccgggagca gacaagcccg tcagggcgcg    540

tcagcgggtg ttggcgggtg tcggggctgg cttaactatg cggcatcaga gcagattgta    600

ctgagagtgc accatatgct taattaacgc ggggcagtgc atgtaatccc ttcagttggt    660

tggtacaact tgccaactgg gccctgttcc acatgtgaca cgggggggga ccaaacacaa    720

aggggttctc tgactgtagt tgacatcctt ataaatggat gtgcacattt gccaacactg    780

agtggctttc atcctggagc agactttgca gtctgtggac tgcaacacaa cattgccttt    840

atgtgtaact cttggctgaa gctcttacac caatgctggg ggacatgtac ctcccagggg    900

cccaggaaga ctacgggagg ctacaccaac gtcaatcaga ggggcctgtg tagctaccga    960

taagcggacc ctcaagaggg cattagcaat agtgtttata aggcccccct gttaacccta   1020

aacgggtagc atatgcttcc cgggtagtag tatatactat ccagactaac cctaattcaa   1080

tagcatatgt tacccaacgg gaagcatatg ctatcgaatt agggttagta aaagggtcct   1140

aaggaacagc gatatctccc accccatgag ctgtcacggt tttatttaca tggggtcagg   1200

attccacgag ggtagtgaac cattttagtc acaagggcag tggctgaaga tcaaggagcg   1260
```

```
ggcagtgaac tctcctgaat cttcgcctgc ttcttcattc tccttcgttt agctaataga   1320

ataactgctg agttgtgaac agtaaggtgt atgtgaggtg ctcgaaaaca aggtttcagg   1380

tgacgccccc agaataaaat ttggacgggg ggttcagtgg tggcattgtg ctatgacacc   1440

aatataaccc tcacaaaccc cttgggcaat aaatactagt gtaggaatga aacattctga   1500

atatctttaa caatagaaat ccatggggtg gggacaagcc gtaaagactg gatgtccatc   1560

tcacacgaat ttatggctat gggcaacaca taatcctagt gcaatatgat actggggtta   1620

ttaagatgtg tcccaggcag ggaccaagac aggtgaacca tgttgttaca ctctatttgt   1680

aacaagggga aagagagtgg acgccgacag cagcggactc cactggttgt ctctaacacc   1740

cccgaaaatt aaacggggct ccacgccaat ggggcccata aacaaagaca agtggccact   1800

cttttttttg aaattgtgga gtgggggcac gcgtcagccc ccacacgccg ccctgcggtt   1860

ttggactgta aaataagggt gtaataactt ggctgattgt aaccccgcta accactgcgg   1920

tcaaaccact tgcccacaaa accactaatg gcaccccggg gaatacctgc ataagtaggt   1980

gggcgggcca agataggggc gcgattgctg cgatctggag gacaaattac acacacttgc   2040

gcctgagcgc caagcacagg gttgttggtc ctcatattca cgaggtcgct gagagcacgg   2100

tgggctaatg ttgccatggg tagcatatac tacccaaata tctggatagc atatgctatc   2160

ctaatctata tctgggtagc ataggctatc ctaatctata tctgggtagc atatgctatc   2220

ctaatctata tctgggtagt atatgctatc ctaatttata tctgggtagc ataggctatc   2280

ctaatctata tctgggtagc atatgctatc ctaatctata tctgggtagt atatgctatc   2340

ctaatctgta tccgggtagc atatgctatc ctaatagaga ttagggtagt atatgctatc   2400

ctaatttata tctgggtagc atatactacc caaatatctg gatagcatat gctatcctaa   2460

tctatatctg ggtagcatat gctatcctaa tctatatctg ggtagcatag gctatcctaa   2520

tctatatctg ggtagcatat gctatcctaa tctatatctg ggtagtatat gctatcctaa   2580

tttatatctg ggtagcatag gctatcctaa tctatatctg ggtagcatat gctatcctaa   2640

tctatatctg ggtagtatat gctatcctaa tctgtatccg ggtagcatat gctatcctca   2700

tgcatataca gtcagcatat gatacccagt agtagagtgg gagtgctatc ctttgcatat   2760

gccgccacct cccaaggggg cgtgaatttt cgctgcttgt ccttttcctg cggcgcgccg   2820

tttaaacatt taaatggatc cgcaccatat gcggtgtgaa ataccgcaca gatgcgtaag   2880

gagaaaatac cgcatcagat tggctattgg ccattgcata cgttgtatcc atatcataat   2940

atgtacattt atattggctc atgtccaaca ttaccgccat gttgacattg attattgact   3000

agttattaat agtaatcaat tacggggtca ttagttcata gcccatatat ggagttccgc   3060

gttacataac ttacggtaaa tggcccgcct ggctgaccgc ccaacgaccc ccgcccattg   3120

acgtcaataa tgacgtatgt tcccatagta acgccaatag ggactttcca ttgacgtcaa   3180

tgggtggagt atttacggta aactgcccac ttggcagtac atcaagtgta tcatatgcca   3240

agtacgcccc ctattgacgt caatgacggt aaatggcccg cctggcatta tgcccagtac   3300

atgaccttat gggactttcc tacttggcag tacatctacg tattagtcat cgctattacc   3360

atggtgatgc ggttttggca gtacatcaat gggcgtggat agcggtttga ctcacgggga   3420

tttccaagtc tccaccccat tgacgtcaat gggagtttgt tttggcacca aaatcaacgg   3480

gactttccaa aatgtcgtaa caactccgcc ccattgacgc aaatgggcgg taggcgtgta   3540

cggtgggagg tctatataag cagagctcgt ttagtgaacc gtcagatcgc ctggagacgc   3600

catccacgct gttttgacct ccatagaaga caccgggacc gatccagcct ccgcggccgg   3660
```

```
gaacggtgca ttggaacgcg gattccccgt gccaagagtg acgtaagtac cgcctataga   3720
gtctataggc ccaccccctt ggcttcttat gcatgctata ctgtttttgg cttggggtct   3780
atacaccccc gcttcctcat gttataggtg atggtatagc ttagcctata ggtgtgggtt   3840
attgaccatt attgaccact cccctattgg tgacgatact ttccattact aatccataac   3900
atggctcttt gccacaactc tctttattgg ctatatgcca atacactgtc cttcagagac   3960
tgacacggac tctgtatttt tacaggatgg ggtctcattt attatttaca aattcacata   4020
tacaacacca ccgtccccag tgcccgcagt ttttattaaa cataacgtgg gatctccacg   4080
cgaatctcgg gtacgtgttc cggacatggg ctcttctccg gtagcggcgg agcttctaca   4140
tccgagccct gctcccatgc ctccagcgac tcatggtcgc tcggcagctc cttgctccta   4200
acagtggagg ccagacttag gcacagcacg atgcccacca ccaccagtgt gccgcacaag   4260
gccgtggcgg tagggtatgt gtctgaaaat gagcgtggag attgggctcg cacggctgac   4320
gcagatggaa gacttaaggc agcggcagaa gaagatgcag gcagctgagt tgttgtattc   4380
tgataagagt cagaggtaac tcccgttgcg gtgctgttaa cggtggaggg cagtgtagtc   4440
tgagcagtac tcgttgctgc cgcgcgcgcc accagacata atagctgaca gactaacaga   4500
ctgttccttt ccatgggtct tttctgcagt caccgtcctt gacacgaagc ttgccgccac   4560
catgagtgtg cccactcagg tcctggggtt gctgctgctg tggcttacag atgccagatg   4620
cgatatcgtg atgacccaga gcccggatag cctggcggtg agcctgggcg aacgtgcgac   4680
cattaactgc agaagcagcc agtctgttct ttattcttct aacaataaga attatctggc   4740
ttggtaccag cagaaaccag gtcagccgcc gaaactatta atttattggg cttctactcg   4800
tgaaagcggg gtcccggatc gttttagcgg ctctggatcc ggcactgatt ttaccctgac   4860
catttcgtcc ctgcaagctg aagacgtggc ggtgtattat tgccagcagt attcttcttt   4920
tcctattacc tttggccagg gtacgaaagt tgaaattaaa cgtacggtgg ctgcaccatc   4980
tgtcttcatc ttcccgccat ctgatgagca gttgaaatct ggaactgcct ctgttgtgtg   5040
cctgctgaat aacttctatc ccagagaggc caaagtacag tggaaggtgg ataacgccct   5100
ccaatcgggt aactcccagg agagtgtcac agagcaggac agcaaggaca gcacctacag   5160
cctcagcagc accctgacgc tgagcaaagc agactacgag aaacacaaag tctacgcctg   5220
cgaagtcacc catcagggcc tgagctcgcc cgtcacaaag agcttcaaca ggggagagtg   5280
ttaggcggcc gcgatctgct gtgccttcta gttgccagcc atctgttgtt tgcccctccc   5340
ccgtgccttc cttgaccctg gaaggtgcca ctcccactgt cctttcctaa taaaatgagg   5400
aaattgcatc gcattgtctg agtaggtgtc attctattct ggggggtggg gtggggcagc   5460
acagcaaggg ggaggattgg gaagacaata gcaggcatgc tggggatgcg gtgggctcta   5520
tggccgctga gatctggccg ctgcggccct gtggaatgtg tgtcagttag ggtgtggaaa   5580
gtccccaggc tccccagcag gcagaagtat gcaaagcatg catctcaatt agtcagcaac   5640
caggtgtgga aagtccccag gctccccagc aggcagaagt atgcaaagca tgcatctcaa   5700
ttagtcagca accatagtcc cgcccctaac tccgcccatc ccgcccctaa ctccgcccag   5760
ttccgcccat tctccgcccc atggctgact aatttttttt atttatgcag aggccgaggc   5820
cgcctctgcc tctgagctat tccagaagta gtgaggaggc ttttttggag gcctaggctt   5880
ttgcaaaaag ctgtcgacca ccatggccac ctcagcaagt tcccacttga acaaaaacat   5940
caagcaaatg tacttgtgcc tgccccaggg tgagaaagtc caagccatgt atatctgggt   6000
tgatggtact ggagaaggac tgcgctgcaa aacccgcacc ctggactgtg agcccaagtg   6060
```

```
tgtagaagag ttacctgagt ggaattttga tggctctagt acctttcagt ctgagggctc   6120
caacagtgac atgtatctca gccctgttgc catgtttcgg gaccccttcc gcagagatcc   6180
caacaagctg gtgttctgtg aagttttcaa gtacaaccgg aagcccgcag agaccaattt   6240
aaggcactcg tgtaaacgga taatggacat ggtgagcaac cagcacccct ggtttggaat   6300
ggaacaggag tatactctga tgggaacaga tgggcaccct tttggttggc cttccaatgg   6360
ctttcctgga ccccaaggtc cgtattactg tggtgtgggc gcagacaaag cctatggcag   6420
ggacatcgtg gaggctcact accgcgcctg cttgtatgct ggggtcaaga ttacaggaac   6480
aaatgctgag gtcatgcctg cccagtggga gttccaaata ggaccctgtg aaggaatccg   6540
catgggagat catctctggg tggcccgttt catcttgcat cgagtatgtg aagactttgg   6600
ggtaatagca acctttgacc ccaagcccat tcctgggaac tggaatggtg caggctgcca   6660
taccaacttt agcaccaagg ccatgcggga ggagaatggt ctgaagcaca tcgaggaggc   6720
catcgagaaa ctaagcaagc ggcaccggta tcacattcga gcctacgatc ccaagggggg   6780
cctggacaat gcccgtggtc tgactgggtt ccacgaaacg tccaacatca acgacttttc   6840
tgctggtgtc gccaatcgca gtgccagcat ccgcattccc cggactgtcg gccaggagaa   6900
gaaaggttac tttgaagacc gccgcccctc tgccaattgt gacccctttg cagtgacaga   6960
agccatcgtc cgcacatgcc ttctcaatga gactggcgac gagcccttcc aatacaaaaa   7020
ctaagtcgac aacttgttta ttgcagctta taatggttac aaataaagca atagcatcac   7080
aaatttcaca aataaagcat ttttttcact gcattctagt tgtggtttgt ccaaactcat   7140
caatgtatct tatcatgtct ggatcggcgc gccggccgct gcggccaggt gctgaagaat   7200
tgacccggtt cctcctgggc cagaaagaag caggcacatc cccttctctg tgacacaccc   7260
tgtccacgcc cctggttctt agttccagcc ccactcatag gacactcata gctcaggagg   7320
gctccgcctt caatcccacc cgctaaagta cttggagcgg tctctccctc cctcatcagc   7380
ccaccaaacc aaacctagcc tccaagagtg ggaagaaatt aaagcaagat aggctattaa   7440
gtgcagaggg agagaaaatg cctccaacat gtgaggaagt aatgagagaa atcatagaat   7500
ttcttccgct tcctcgctca ctgactcgct gcgctcggtc gttcggctgc ggcgagcggt   7560
atcagctcac tcaaaggcgg taatacggtt atccacagaa tcaggggata acgcaggaaa   7620
gaacatgtga gcaaaaggcc agcaaaaggc caggaaccgt aaaaaggccg cgttgctggc   7680
gtttttccat aggctccgcc cccctgacga gcatcacaaa aatcgacgct caagtcagag   7740
gtggcgaaac ccgacaggac tataaagata ccaggcgttt ccccctggaa gctccctcgt   7800
gcgctctcct gttccgaccc tgccgcttac cggatacctg tccgcctttc tcccttcggg   7860
aagcgtggcg ctttctcaat gctcacgctg taggtatctc agttcggtgt aggtcgttcg   7920
ctccaagctg ggctgtgtgc acgaaccccc cgttcagccc gaccgctgcg ccttatccgg   7980
taactatcgt cttgagtcca acccggtaag acacgactta tcgccactgg cagcagccac   8040
tggtaacagg attagcagag cgaggtatgt aggcggtgct acagagttct tgaagtggtg   8100
gcctaactac ggctacacta gaaggacagt atttggtatc tgcgctctgc tgaagccagt   8160
taccttcgga aaaagagttg gtagctcttg atccggcaaa caaaccaccg ctggtagcgg   8220
tggttttttt gtttgcaagc agcagattac gcgcagaaaa aaaggatctc aagaagatcc   8280
tttgatcttt tctacggggt ctgacgctca gtggaacgaa aactcacgtt aagggatttt   8340
ggtcatgaga ttatcaaaaa ggatcttcac ctagatcctt ttaaattaaa aatgaagttt   8400
taaatcaatc taaagtatat atgagtaaac ttggtctgac agttaccaat gcttaatcag   8460
```

```
tgaggcacct atctcagcga tctgtctatt tcgttcatcc atagttgcct gactccgggg   8520

gggggggcg ctgaggtctg cctcgtgaag aaggtgttgc tgactcatac caggcctgaa   8580

tcgccccatc atccagccag aaagtgaggg agccacggtt gatgagagct ttgttgtagg   8640

tggaccagtt ggtgattttg aacttttgct ttgccacgga acggtctgcg ttgtcgggaa   8700

gatgcgtgat ctgatccttc aactcagcaa aagttcgatt tattcaacaa agccgccgtc   8760

ccgtcaagtc agcgtaatgc tctgccagtg ttacaaccaa ttaaccaatt ctgattagaa   8820

aaactcatcg agcatcaaat gaaactgcaa tttattcata tcaggattat caataccata   8880

tttttgaaaa agccgtttct gtaatgaagg agaaaactca ccgaggcagt tccataggat   8940

ggcaagatcc tggtatcggt ctgcgattcc gactcgtcca acatcaatac aacctattaa   9000

tttcccctcg tcaaaaataa ggttatcaag tgagaaatca ccatgagtga cgactgaatc   9060

cggtgagaat ggcaaaagct tatgcatttc tttccagact tgttcaacag gccagccatt   9120

acgctcgtca tcaaaatcac tcgcatcaac caaaccgtta ttcattcgtg attgcgcctg   9180

agcgagacga aatacgcgat cgctgttaaa aggacaatta caaacaggaa tcgaatgcaa   9240

ccggcgcagg aacactgcca gcgcatcaac aatattttca cctgaatcag gatattcttc   9300

taatacctgg aatgctgttt tcccggggat cgcagtggtg agtaaccatg catcatcagg   9360

agtacggata aaatgcttga tggtcggaag aggcataaat tccgtcagcc agtttagtct   9420

gaccatctca tctgtaacat cattggcaac gctacctttg ccatgtttca gaaacaactc   9480

tggcgcatcg ggcttcccat acaat                                         9505
```

<210> SEQ ID NO 37
<211> LENGTH: 10
<212> TYPE: PRT
<213> ORGANISM: Artificial Sequence
<220> FEATURE:
<223> OTHER INFORMATION: 1B20 Antibody Variant VH CDR1 Sequence
<221> NAME/KEY: VARIANT
<222> LOCATION: 6
<223> OTHER INFORMATION: Xaa = Asn or Asp
<221> NAME/KEY: VARIANT
<222> LOCATION: 8
<223> OTHER INFORMATION: Xaa = Trp or Tyr
<221> NAME/KEY: VARIANT
<222> LOCATION: 10
<223> OTHER INFORMATION: Xaa = Ser, Thr or Ala

<400> SEQUENCE: 37

```
Gly Tyr Ser Phe Thr Xaa Tyr Xaa Ile Xaa
 1               5                  10
```

<210> SEQ ID NO 38
<211> LENGTH: 20
<212> TYPE: PRT
<213> ORGANISM: Artificial Sequence
<220> FEATURE:
<223> OTHER INFORMATION: 1B20 Antibody Variant VH CDR2 Sequence
<221> NAME/KEY: VARIANT
<222> LOCATION: 4
<223> OTHER INFORMATION: Xaa = Ile, Arg, Trp, Leu, or Met
<221> NAME/KEY: VARIANT
<222> LOCATION: 11
<223> OTHER INFORMATION: Xaa = Tyr or Asp
<221> NAME/KEY: VARIANT
<222> LOCATION: 13
<223> OTHER INFORMATION: Xaa = Asn, Arg, His, Ser, Lys or Gln
<221> NAME/KEY: VARIANT
<222> LOCATION: 15
<223> OTHER INFORMATION: Xaa = Ser or Asn
<221> NAME/KEY: VARIANT
<222> LOCATION: 16
<223> OTHER INFORMATION: Xaa = Pro, Gln, or His

```
<221> NAME/KEY: VARIANT
<222> LOCATION: (17)...(17)
<223> OTHER INFORMATION: Xaa = Ser, Lys, Asn or Arg

<400> SEQUENCE: 38

Trp Met Gly Xaa Ile Tyr Pro Gly Asp Ser Xaa Thr Xaa Tyr Xaa Xaa
 1               5                  10                  15

Xaa Phe Gln Gly
            20


<210> SEQ ID NO 39
<211> LENGTH: 10
<212> TYPE: PRT
<213> ORGANISM: Artificial Sequence
<220> FEATURE:
<223> OTHER INFORMATION: 1B20 Antibody Variant VH CDR3 Sequence
<221> NAME/KEY: VARIANT
<222> LOCATION: 2
<223> OTHER INFORMATION: Xaa = Tyr, Arg or His
<221> NAME/KEY: VARIANT
<222> LOCATION: 3
<223> OTHER INFORMATION: Xaa = Trp, Tyr, Gly, Ala or Phe
<221> NAME/KEY: VARIANT
<222> LOCATION: 4
<223> OTHER INFORMATION: Xaa = Tyr or Ser
<221> NAME/KEY: VARIANT
<222> LOCATION: 5
<223> OTHER INFORMATION: Xaa = Lys, Arg, Thr, Gly, Ser, Asp, Glu, His,
      Asn or Gln
<221> NAME/KEY: VARIANT
<222> LOCATION: 6
<223> OTHER INFORMATION: Xaa = Pro, Ser, Gly, Asp, Ala, His, Arg or Tyr
<221> NAME/KEY: VARIANT
<222> LOCATION: (7)...(7)
<223> OTHER INFORMATION: xaa = Leu, Tyr, Phe, Ala, Asp, His, Pro, Ser or
      Val
<221> NAME/KEY: VARIANT
<222> LOCATION: (8)...(8)
<223> OTHER INFORMATION: xaa = Phe or Ser
<221> NAME/KEY: VARIANT
<222> LOCATION: (10)...(10)
<223> OTHER INFORMATION: xaa = Ile, Val, Tyr, Phe or Asn

<400> SEQUENCE: 39

Asp Xaa Xaa Xaa Xaa Xaa Xaa Xaa Asp Xaa
 1               5                  10


<210> SEQ ID NO 40
<211> LENGTH: 17
<212> TYPE: PRT
<213> ORGANISM: Artificial Sequence
<220> FEATURE:
<223> OTHER INFORMATION: 1B20 Antibody Variant VL CDR1 Sequence
<221> NAME/KEY: VARIANT
<222> LOCATION: 1
<223> OTHER INFORMATION: Xaa = Arg, Lys, His, Asn, Gln or Ser
<221> NAME/KEY: VARIANT
<222> LOCATION: 7
<223> OTHER INFORMATION: Xaa = Leu or Phe
<221> NAME/KEY: VARIANT
<222> LOCATION: 8
<223> OTHER INFORMATION: Xaa = Tyr or His
<221> NAME/KEY: VARIANT
<222> LOCATION: 10
<223> OTHER INFORMATION: Xaa = Ser, Arg or Gly
<221> NAME/KEY: VARIANT
<222> LOCATION: 11
<223> OTHER INFORMATION: Xaa = Asn or Thr
<221> NAME/KEY: VARIANT
<222> LOCATION: (12)...(12)
<223> OTHER INFORMATION: xaa = Asn, Arg, His or Ser
<221> NAME/KEY: VARIANT
<222> LOCATION: (15)...(15)
<223> OTHER INFORMATION: xaa = Tyr or Phe
<221> NAME/KEY: VARIANT
```

<222> LOCATION: (17)...(17)
<223> OTHER INFORMATION: xaa = Ala or Thr

<400> SEQUENCE: 40

Xaa Ser Ser Gln Ser Val Xaa Xaa Ser Xaa Xaa Xaa Lys Asn Xaa Leu
1 5 10 15

Xaa

<210> SEQ ID NO 41
<211> LENGTH: 11
<212> TYPE: PRT
<213> ORGANISM: Artificial Sequence
<220> FEATURE:
<223> OTHER INFORMATION: 1B20 Antibody Variant VL CDR2 Sequence
<221> NAME/KEY: VARIANT
<222> LOCATION: 5
<223> OTHER INFORMATION: Xaa = Trp, Phe or Leu
<221> NAME/KEY: VARIANT
<222> LOCATION: 6
<223> OTHER INFORMATION: Xaa = Ala or Thr
<221> NAME/KEY: VARIANT
<222> LOCATION: 8
<223> OTHER INFORMATION: Xaa = Thr, Ile, Ala or Val
<221> NAME/KEY: VARIANT
<222> LOCATION: 10
<223> OTHER INFORMATION: Xaa = Glu, Ala or Lys
<221> NAME/KEY: VARIANT
<222> LOCATION: 11
<223> OTHER INFORMATION: Xaa = Ser or Thr

<400> SEQUENCE: 41

Leu Leu Ile Tyr Xaa Xaa Ser Xaa Arg Xaa Xaa
1 5 10

<210> SEQ ID NO 42
<211> LENGTH: 8
<212> TYPE: PRT
<213> ORGANISM: Artificial Sequence
<220> FEATURE:
<223> OTHER INFORMATION: 1B20 Antibody Variant VL CDR3 Sequence
<221> NAME/KEY: VARIANT
<222> LOCATION: 4
<223> OTHER INFORMATION: Xaa = Ser or Tyr
<221> NAME/KEY: VARIANT
<222> LOCATION: 5
<223> OTHER INFORMATION: Xaa = Ser or Thr
<221> NAME/KEY: VARIANT
<222> LOCATION: 6
<223> OTHER INFORMATION: Xaa = Phe, Tyr, Leu, Thr, His, Ile, Asn, Pro or Ser
<221> NAME/KEY: VARIANT
<222> LOCATION: 8
<223> OTHER INFORMATION: Xaa = Ile, Arg, Val, Tyr, Asp, Phe, Gly, His, Leu, Asn or Ser

<400> SEQUENCE: 42

Gln Gln Tyr Xaa Xaa Xaa Pro Xaa
1 5

<210> SEQ ID NO 43
<211> LENGTH: 114
<212> TYPE: PRT
<213> ORGANISM: Artificial Sequence
<220> FEATURE:
<223> OTHER INFORMATION: VL; 1B20 Variant Sequence
<221> NAME/KEY: VARIANT
<222> LOCATION: 24
<223> OTHER INFORMATION: Xaa = Arg, Lys, His, Asn, Gln or Ser
<221> NAME/KEY: VARIANT
<222> LOCATION: 30
<223> OTHER INFORMATION: Xaa = Leu or Phe
<221> NAME/KEY: VARIANT
<222> LOCATION: 31

<223> OTHER INFORMATION: Xaa = Tyr or His
<221> NAME/KEY: VARIANT
<222> LOCATION: 33
<223> OTHER INFORMATION: Xaa = ser, Arg or Gly
<221> NAME/KEY: VARIANT
<222> LOCATION: 34
<223> OTHER INFORMATION: Xaa = Asn or Thr
<221> NAME/KEY: VARIANT
<222> LOCATION: (35)...(35)
<223> OTHER INFORMATION: Xaa = Asn, Arg, His or Ser
<221> NAME/KEY: VARIANT
<222> LOCATION: (38)...(38)
<223> OTHER INFORMATION: Xaa = Tyr or Phe
<221> NAME/KEY: VARIANT
<222> LOCATION: (40)...(40)
<223> OTHER INFORMATION: Xaa = Ala or Thr
<221> NAME/KEY: VARIANT
<222> LOCATION: (56)...(56)
<223> OTHER INFORMATION: Xaa = Trp, Phe or Leu
<221> NAME/KEY: VARIANT
<222> LOCATION: (57)...(57)
<223> OTHER INFORMATION: Xaa = Ala or Thr
<221> NAME/KEY: VARIANT
<222> LOCATION: (59)...(59)
<223> OTHER INFORMATION: Xaa = Thr, Ile, Ala or Val
<221> NAME/KEY: VARIANT
<222> LOCATION: (61)...(61)
<223> OTHER INFORMATION: Xaa = Glu, Ala or Lys
<221> NAME/KEY: VARIANT
<222> LOCATION: (62)...(62)
<223> OTHER INFORMATION: Xaa = Ser or Thr
<221> NAME/KEY: VARIANT
<222> LOCATION: (98)...(98)
<223> OTHER INFORMATION: Xaa = Ser or Tyr
<221> NAME/KEY: VARIANT
<222> LOCATION: (99)...(99)
<223> OTHER INFORMATION: Xaa = Ser or Thr
<221> NAME/KEY: VARIANT
<222> LOCATION: (100)...(100)
<223> OTHER INFORMATION: Xaa = Phe, Tyr, Leu, Thr, His, Ile, Asn, Pro or
      Ser
<221> NAME/KEY: VARIANT
<222> LOCATION: (102)...(102)
<223> OTHER INFORMATION: Xaa = Ile, Arg, Val, Tyr, Asp, Phe, Gly, His,
      Leu, Asn or Ser

<400> SEQUENCE: 43

```
Asp Ile Val Met Thr Gln Ser Pro Asp Ser Leu Ala Val Ser Leu Gly
 1               5                  10                  15

Glu Arg Ala Thr Ile Asn Cys Xaa Ser Ser Gln Ser Val Xaa Xaa Ser
            20                  25                  30

Xaa Xaa Xaa Lys Asn Xaa Leu Xaa Trp Tyr Gln Gln Lys Pro Gly Gln
        35                  40                  45

Pro Pro Lys Leu Leu Ile Tyr Xaa Xaa Ser Xaa Arg Xaa Xaa Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Xaa Xaa Xaa Pro Xaa Thr Phe Gly Gln Gly Thr Lys Val Glu Ile
            100                 105                 110

Lys Arg
```

<210> SEQ ID NO 44
<211> LENGTH: 119
<212> TYPE: PRT
<213> ORGANISM: Artificial Sequence
<220> FEATURE:
<223> OTHER INFORMATION: VH; 1B20 Variant Sequence
<221> NAME/KEY: VARIANT
<222> LOCATION: 31

<223> OTHER INFORMATION: Xaa = Asn or Asp
<221> NAME/KEY: VARIANT
<222> LOCATION: 33
<223> OTHER INFORMATION: Xaa = Trp or Tyr
<221> NAME/KEY: VARIANT
<222> LOCATION: 35
<223> OTHER INFORMATION: Xaa = Ser, Thr or Ala
<221> NAME/KEY: VARIANT
<222> LOCATION: 50
<223> OTHER INFORMATION: Xaa = Ile, Arg, Trp, Leu or Met
<221> NAME/KEY: VARIANT
<222> LOCATION: 57
<223> OTHER INFORMATION: Xaa = Tyr or Asp
<221> NAME/KEY: VARIANT
<222> LOCATION: (59)...(59)
<223> OTHER INFORMATION: Xaa = Asn, Arg, His, Ser, Lys or Gln
<221> NAME/KEY: VARIANT
<222> LOCATION: (61)...(61)
<223> OTHER INFORMATION: Xaa = Ser or Asn
<221> NAME/KEY: VARIANT
<222> LOCATION: (62)...(62)
<223> OTHER INFORMATION: Xaa = Pro, Gln or His
<221> NAME/KEY: VARIANT
<222> LOCATION: (63)...(63)
<223> OTHER INFORMATION: Xaa = Ser, Lys, Asn or Arg
<221> NAME/KEY: VARIANT
<222> LOCATION: (100)...(100)
<223> OTHER INFORMATION: Xaa = Tyr, Arg or His
<221> NAME/KEY: VARIANT
<222> LOCATION: (101)...(101)
<223> OTHER INFORMATION: Xaa = Trp, Tyr or Gly
<221> NAME/KEY: VARIANT
<222> LOCATION: (102)...(102)
<223> OTHER INFORMATION: Xaa = Tyr or Ser
<221> NAME/KEY: VARIANT
<222> LOCATION: (103)...(103)
<223> OTHER INFORMATION: Xaa = Lys, Arg, Thr, Gly, Ser, Asp, Glu, His, Asn or Gln
<221> NAME/KEY: VARIANT
<222> LOCATION: (104)...(104)
<223> OTHER INFORMATION: Xaa = Pro, Ser, Gly, Asp, Ala, His, Arg or Tyr
<221> NAME/KEY: VARIANT
<222> LOCATION: (105)...(105)
<223> OTHER INFORMATION: Xaa = Leu, Tyr, Phe, Ala, Asp, His, Pro, Ser or Val
<221> NAME/KEY: VARIANT
<222> LOCATION: (106)...(106)
<223> OTHER INFORMATION: Xaa = Phe or Ser
<221> NAME/KEY: VARIANT
<222> LOCATION: (108)...(108)
<223> OTHER INFORMATION: Xaa = Ile, Val, Tyr, Phe or Asn

<400> SEQUENCE: 44

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Xaa Tyr
            20                  25                  30

Xaa Ile Xaa Trp Val Arg Gln Met Pro Gly Lys Gly Leu Glu Trp Met
        35                  40                  45

Gly Xaa Ile Tyr Pro Gly Asp Ser Xaa Thr Xaa Tyr Xaa Xaa Xaa Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Xaa Xaa Xaa Xaa Xaa Xaa Xaa Asp Xaa Trp Gly Gln Gly
            100                 105                 110

Thr Leu Val Thr Val Ser Ser
        115
```

<210> SEQ ID NO 45

```
<211> LENGTH: 119
<212> TYPE: PRT
<213> ORGANISM: Artificial Sequence
<220> FEATURE:
<223> OTHER INFORMATION: VH; 1B20 Variant Sequence F120

<400> SEQUENCE: 45

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Leu Ile Tyr Pro Gly Asp Ser Tyr Thr Arg Tyr Asn Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Tyr Ser Arg Pro Phe Ser Asp Ile Trp Gly Gln Gly
            100                 105                 110

Thr Leu Val Thr Val Ser Ser
        115


<210> SEQ ID NO 46
<211> LENGTH: 119
<212> TYPE: PRT
<213> ORGANISM: Artificial Sequence
<220> FEATURE:
<223> OTHER INFORMATION: VH; 1B20 Variant Sequence F116

<400> SEQUENCE: 46

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Leu Ile Tyr Pro Gly Asp Ser Tyr Thr Arg Tyr Asn Pro Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Tyr Ser Arg Pro Tyr Ser Asp Val Trp Gly Gln Gly
            100                 105                 110

Thr Leu Val Thr Val Ser Ser
        115


<210> SEQ ID NO 47
<211> LENGTH: 119
<212> TYPE: PRT
<213> ORGANISM: Artificial Sequence
<220> FEATURE:
<223> OTHER INFORMATION: VH; 1B20 Variant Sequence F119

<400> SEQUENCE: 47

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
```

```
            20                  25                  30

Tyr Ile Ser Trp Val Arg Gln Met Pro Gly Lys Gly Leu Glu Trp Met
        35                  40                  45

Gly Leu Ile Tyr Pro Gly Asp Ser Tyr Thr Arg Tyr Ser Pro Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Gly Tyr Arg Pro Tyr Ser Asp Ile Trp Gly Gln Gly
            100                 105                 110

Thr Leu Val Thr Val Ser Ser
        115


<210> SEQ ID NO 48
<211> LENGTH: 119
<212> TYPE: PRT
<213> ORGANISM: Artificial Sequence
<220> FEATURE:
<223> OTHER INFORMATION: VH; 1B20 Variant Sequence F113

<400> SEQUENCE: 48

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Leu Ile Tyr Pro Gly Asp Ser Tyr Thr Asn Tyr Asn Pro Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Tyr Ser Thr Pro Phe Phe Asp Val Trp Gly Gln Gly
            100                 105                 110

Thr Leu Val Thr Val Ser Ser
        115


<210> SEQ ID NO 49
<211> LENGTH: 119
<212> TYPE: PRT
<213> ORGANISM: Artificial Sequence
<220> FEATURE:
<223> OTHER INFORMATION: VH; 1B20 Variant Sequence E2

<400> SEQUENCE: 49

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Leu Ile Tyr Pro Gly Asp Ser Tyr Thr Arg Tyr Asn Arg Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
```

```
                85                  90                  95

Ala Arg Asp Tyr Tyr Ser Arg Pro Leu Ser Asp Val Trp Gly Gln Gly
            100                 105                 110

Thr Leu Val Thr Val Ser Ser
        115


<210> SEQ ID NO 50
<211> LENGTH: 119
<212> TYPE: PRT
<213> ORGANISM: Artificial Sequence
<220> FEATURE:
<223> OTHER INFORMATION: VH; 1B20 Variant Sequence G4

<400> SEQUENCE: 50

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Leu Ile Tyr Pro Gly Asp Ser Tyr Thr Arg Tyr Ser Pro Arg Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Gly Tyr Lys Pro Tyr Ser Asp Ile Trp Gly Gln Gly
            100                 105                 110

Thr Leu Val Thr Val Ser Ser
        115


<210> SEQ ID NO 51
<211> LENGTH: 119
<212> TYPE: PRT
<213> ORGANISM: Artificial Sequence
<220> FEATURE:
<223> OTHER INFORMATION: VH; 1B20 Variant Sequence F4

<400> SEQUENCE: 51

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Leu Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Tyr Ser Lys Pro Leu Phe Asp Val Trp Gly Gln Gly
            100                 105                 110

Thr Leu Val Thr Val Ser Ser
        115


<210> SEQ ID NO 52
<211> LENGTH: 119
<212> TYPE: PRT
```

```
<213> ORGANISM: Artificial Sequence
<220> FEATURE:
<223> OTHER INFORMATION: VH; 1B20 Variant Sequence B9

<400> SEQUENCE: 52

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Ile Ile Tyr Pro Gly Asp Ser Tyr Ile His Tyr Asn Gln Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Tyr Ser Arg Pro Phe Ser Asp Ile Trp Gly Gln Gly
            100                 105                 110

Thr Leu Val Thr Val Ser Ser
        115


<210> SEQ ID NO 53
<211> LENGTH: 119
<212> TYPE: PRT
<213> ORGANISM: Artificial Sequence
<220> FEATURE:
<223> OTHER INFORMATION: VH; 1B20 Variant Sequence C3

<400> SEQUENCE: 53

Gln Val Lys Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ala Trp Val Arg Gln Met Pro Gly Lys Gly Leu Glu Trp Met
        35                  40                  45

Gly Ile Ile Tyr Pro Gly Asp Ser Tyr Thr His Tyr Asn Pro Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Gly Tyr Lys Pro Phe Ser Asp Ile Trp Gly Gln Gly
            100                 105                 110

Thr Leu Val Thr Val Ser Ser
        115


<210> SEQ ID NO 54
<211> LENGTH: 119
<212> TYPE: PRT
<213> ORGANISM: Artificial Sequence
<220> FEATURE:
<223> OTHER INFORMATION: VH; 1B20 Variant Sequence F2

<400> SEQUENCE: 54

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30
```

```
Tyr Ile Ala Trp Val Arg Gln Met Pro Gly Lys Gly Leu Glu Trp Met
        35                  40                  45

Gly Val Ile Tyr Pro Gly Asp Ser Tyr Thr Arg Tyr Asn Pro Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Arg Pro Tyr Phe Asp Ile Trp Gly Gln Gly
            100                 105                 110

Thr Leu Val Thr Val Ser Ser
        115


<210> SEQ ID NO 55
<211> LENGTH: 119
<212> TYPE: PRT
<213> ORGANISM: Artificial Sequence
<220> FEATURE:
<223> OTHER INFORMATION: VH; 1B20 Variant Sequence F7

<400> SEQUENCE: 55

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ala Trp Val Arg Gln Met Pro Gly Lys Gly Leu Glu Trp Met
        35                  40                  45

Gly Ile Ile Tyr Pro Gly Asp Ser Tyr Thr His Tyr Asn Pro Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Ser Arg Pro Phe Ser Asp Val Trp Gly Gln Gly
            100                 105                 110

Thr Leu Val Thr Val Ser Ser
        115


<210> SEQ ID NO 56
<211> LENGTH: 119
<212> TYPE: PRT
<213> ORGANISM: Artificial Sequence
<220> FEATURE:
<223> OTHER INFORMATION: VH; 1B20 Variant Sequence A7

<400> SEQUENCE: 56

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Ile Ile Tyr Pro Gly Asp Ser Tyr Thr Arg Tyr Asn Pro Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95
```

```
Ala Arg Asp Tyr Trp Ser Lys Pro Leu Ser Asp Val Trp Gly Gln Gly
            100                 105                 110

Thr Leu Val Thr Val Ser Ser
        115


<210> SEQ ID NO 57
<211> LENGTH: 119
<212> TYPE: PRT
<213> ORGANISM: Artificial Sequence
<220> FEATURE:
<223> OTHER INFORMATION: VH; 1B20 Variant Sequence G8

<400> SEQUENCE: 57

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Leu Ile Tyr Pro Gly Asp Ser Tyr Thr His Tyr Asn Pro Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Ser Lys Pro Tyr Phe Asp Val Trp Gly Gln Gly
            100                 105                 110

Thr Leu Val Thr Val Ser Ser
        115


<210> SEQ ID NO 58
<211> LENGTH: 119
<212> TYPE: PRT
<213> ORGANISM: Artificial Sequence
<220> FEATURE:
<223> OTHER INFORMATION: VH; 1B20 Variant Sequence H4

<400> SEQUENCE: 58

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Thr Trp Val Arg Gln Met Pro Gly Arg Gly Leu Glu Trp Met
        35                  40                  45

Gly Ile Ile Tyr Pro Gly Asp Ser Tyr Thr Arg Tyr Asn Pro Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Ser Lys Pro Phe Ser Asp Val Trp Gly Gln Gly
            100                 105                 110

Thr Leu Val Thr Val Ser Ser
        115


<210> SEQ ID NO 59
<211> LENGTH: 119
<212> TYPE: PRT
<213> ORGANISM: Artificial Sequence
<220> FEATURE:
```

<223> OTHER INFORMATION: VH; 1B20 Variant Sequence D5

<400> SEQUENCE: 59

Gln Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Asn Tyr
20 25 30

Tyr Ile Thr Trp Val Arg Gln Met Pro Gly Lys Gly Leu Glu Trp Met
35 40 45

Gly Leu Ile Tyr Pro Gly Asp Ser Tyr Thr Arg Tyr Ser Pro Arg Phe
50 55 60

Gln Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Asp His Trp Ser Arg Pro Tyr Ser Asp Val Trp Gly Gln Gly
100 105 110

Thr Leu Val Thr Val Ser Ser
115

<210> SEQ ID NO 60
<211> LENGTH: 119
<212> TYPE: PRT
<213> ORGANISM: Artificial Sequence
<220> FEATURE:
<223> OTHER INFORMATION: VH; 1B20 Variant Sequence D4

<400> SEQUENCE: 60

Gln Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Asp Tyr
20 25 30

Tyr Ile Ala Trp Val Arg Gln Met Pro Gly Lys Gly Leu Glu Trp Met
35 40 45

Gly Ile Ile Tyr Pro Gly Asp Ser Tyr Thr Arg Tyr Asn Pro Lys Phe
50 55 60

Gln Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Asp Tyr Trp Ser Arg Pro Phe Ser Asp Val Trp Gly Gln Gly
100 105 110

Thr Leu Val Thr Val Ser Ser
115

<210> SEQ ID NO 61
<211> LENGTH: 119
<212> TYPE: PRT
<213> ORGANISM: Artificial Sequence
<220> FEATURE:
<223> OTHER INFORMATION: VH; 1B20 Variant Sequence B4

<400> SEQUENCE: 61

Gln Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Asp Tyr
20 25 30

Tyr Ile Ser Trp Val Arg Gln Met Pro Gly Lys Gly Leu Glu Trp Met
35 40 45

```
Gly Leu Ile Tyr Pro Gly Asp Ser Tyr Thr His Tyr Asn Pro Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Lys Pro Leu Phe Asp Val Trp Gly Gln Gly
            100                 105                 110

Thr Leu Val Thr Val Ser Ser
        115


<210> SEQ ID NO 62
<211> LENGTH: 119
<212> TYPE: PRT
<213> ORGANISM: Artificial Sequence
<220> FEATURE:
<223> OTHER INFORMATION: VH; 1B20 Variant Sequence H1

<400> SEQUENCE: 62

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ala Trp Val Arg Gln Met Pro Gly Lys Gly Leu Glu Trp Met
        35                  40                  45

Gly Ile Ile Tyr Pro Gly Asp Ser Tyr Thr Arg Tyr Asn Pro Arg Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Lys Pro Leu Ser Asp Ile Trp Gly Gln Gly
            100                 105                 110

Thr Leu Val Thr Val Ser Ser
        115


<210> SEQ ID NO 63
<211> LENGTH: 119
<212> TYPE: PRT
<213> ORGANISM: Artificial Sequence
<220> FEATURE:
<223> OTHER INFORMATION: VH; 1B20 Variant Sequence G2

<400> SEQUENCE: 63

Gln Val Lys Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Ile Ile Tyr Pro Gly Asp Ser Tyr Thr His Tyr Asn Pro Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Arg Trp Ser Lys Pro Leu Phe Asp Val Trp Gly Gln Gly
            100                 105                 110
```

```
Thr Leu Val Thr Val Ser Ser
        115


<210> SEQ ID NO 64
<211> LENGTH: 119
<212> TYPE: PRT
<213> ORGANISM: Artificial Sequence
<220> FEATURE:
<223> OTHER INFORMATION: VH; 1B20 Variant Sequence A1

<400> SEQUENCE: 64

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Leu Ile Tyr Pro Gly Asp Ser Tyr Thr Arg Tyr Asn Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Lys Pro Leu Ser Asp Ile Trp Gly Gln Gly
            100                 105                 110

Thr Leu Val Thr Val Ser Ser
        115


<210> SEQ ID NO 65
<211> LENGTH: 119
<212> TYPE: PRT
<213> ORGANISM: Artificial Sequence
<220> FEATURE:
<223> OTHER INFORMATION: VH; 1B20 Variant Sequence A4

<400> SEQUENCE: 65

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Ser Ile Tyr Pro Gly Asp Ser Tyr Thr His Tyr Ser His Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Arg Asp His Trp Ser Arg Pro Phe Phe Asp Val Trp Gly Gln Gly
            100                 105                 110

Thr Leu Val Thr Val Ser Ser
        115


<210> SEQ ID NO 66
<211> LENGTH: 119
<212> TYPE: PRT
<213> ORGANISM: Artificial Sequence
<220> FEATURE:
<223> OTHER INFORMATION: VH; 1B20 Variant Sequence C2
```

<400> SEQUENCE: 66

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ala Trp Val Arg Gln Met Pro Gly Lys Gly Leu Glu Trp Met
        35                  40                  45

Gly Leu Ile Tyr Pro Gly Asp Ser Tyr Thr Ser Tyr Asn Pro Arg Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Thr Pro Tyr Phe Asp Ile Trp Gly Gln Gly
            100                 105                 110

Thr Leu Val Thr Val Ser Ser
        115
```

<210> SEQ ID NO 67
<211> LENGTH: 119
<212> TYPE: PRT
<213> ORGANISM: Artificial Sequence
<220> FEATURE:
<223> OTHER INFORMATION: VH; 1B20 Variant Sequence H5

<400> SEQUENCE: 67

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Ile Ile Tyr Pro Gly Asp Ser Tyr Thr Ser Tyr Ser Pro Arg Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Arg Pro Leu Phe Asp Val Trp Gly Gln Gly
            100                 105                 110

Thr Leu Val Thr Val Ser Ser
        115
```

<210> SEQ ID NO 68
<211> LENGTH: 119
<212> TYPE: PRT
<213> ORGANISM: Artificial Sequence
<220> FEATURE:
<223> OTHER INFORMATION: VH; 1B20 Variant Sequence F6

<400> SEQUENCE: 68

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Leu Ile Tyr Pro Gly Asp Ser Tyr Thr His Tyr Asn Pro Ser Phe
```

```
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Tyr Lys Pro Phe Ser Asp Ile Trp Gly Gln Gly
            100                 105                 110

Thr Leu Val Thr Val Ser Ser
        115


<210> SEQ ID NO 69
<211> LENGTH: 119
<212> TYPE: PRT
<213> ORGANISM: Artificial Sequence
<220> FEATURE:
<223> OTHER INFORMATION: VH; 1B20 Variant Sequence B6

<400> SEQUENCE: 69

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Ile Ile Tyr Pro Gly Asp Ser Tyr Thr Asn Tyr Asn Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Arg Pro Phe Ser Asp Ile Trp Gly Gln Gly
            100                 105                 110

Thr Leu Val Thr Val Ser Ser
        115


<210> SEQ ID NO 70
<211> LENGTH: 119
<212> TYPE: PRT
<213> ORGANISM: Artificial Sequence
<220> FEATURE:
<223> OTHER INFORMATION: VH; 1B20 Variant Sequence B1

<400> SEQUENCE: 70

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Ile Ile Tyr Pro Gly Asp Ser Tyr Thr His Tyr Ser Pro Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Thr Pro Phe Phe Asp Val Trp Gly Gln Gly
            100                 105                 110

Thr Leu Val Thr Val Ser Ser
```

```
        115


<210> SEQ ID NO 71
<211> LENGTH: 119
<212> TYPE: PRT
<213> ORGANISM: Artificial Sequence
<220> FEATURE:
<223> OTHER INFORMATION: VH; 1B20 Variant Sequence F1

<400> SEQUENCE: 71

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Leu Ile Tyr Pro Gly Asp Ser Tyr Thr Asn Tyr Ser Pro Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Ser Lys Pro Leu Ser Asp Val Trp Gly Gln Gly
            100                 105                 110

Thr Leu Val Thr Val Ser Ser
        115


<210> SEQ ID NO 72
<211> LENGTH: 119
<212> TYPE: PRT
<213> ORGANISM: Artificial Sequence
<220> FEATURE:
<223> OTHER INFORMATION: VH; 1B20 Variant Sequence A8

<400> SEQUENCE: 72

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr His Tyr Ser Pro Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Lys Pro Tyr Phe Asp Val Trp Gly Gln Gly
            100                 105                 110

Thr Leu Val Thr Val Ser Ser
        115


<210> SEQ ID NO 73
<211> LENGTH: 119
<212> TYPE: PRT
<213> ORGANISM: Artificial Sequence
<220> FEATURE:
<223> OTHER INFORMATION: VH; 1B20 Variant Sequence B3

<400> SEQUENCE: 73
```

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr Ser Tyr Asn Pro Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Ser Lys Pro Tyr Phe Asp Ile Trp Gly Gln Gly
            100                 105                 110

Thr Leu Val Thr Val Ser Ser
        115


<210> SEQ ID NO 74
<211> LENGTH: 119
<212> TYPE: PRT
<213> ORGANISM: Artificial Sequence
<220> FEATURE:
<223> OTHER INFORMATION: VH; 1B20 Variant Sequence F8

<400> SEQUENCE: 74

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr Asn Tyr Asn Gln Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Arg Pro Tyr Ser Asp Ile Trp Gly Gln Gly
            100                 105                 110

Thr Leu Val Thr Val Ser Ser
        115


<210> SEQ ID NO 75
<211> LENGTH: 119
<212> TYPE: PRT
<213> ORGANISM: Artificial Sequence
<220> FEATURE:
<223> OTHER INFORMATION: VH; 1B20 Variant Sequence H8

<400> SEQUENCE: 75

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr His Tyr Ser Gln Asn Phe
    50                  55                  60
```

```
Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Ser Arg Pro Phe Phe Asp Val Trp Gly Gln Gly
            100                 105                 110

Thr Leu Val Thr Val Ser Ser
        115
```

<210> SEQ ID NO 76
<211> LENGTH: 119
<212> TYPE: PRT
<213> ORGANISM: Artificial Sequence
<220> FEATURE:
<223> OTHER INFORMATION: VH; 1B20 Variant Sequence B5

<400> SEQUENCE: 76

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Ser Ser Ser Leu Lys Ala Ser Asp Thr Ala Met Tyr Tyr Cys
                85                  90                  95

Ala Arg Asp Tyr Trp Tyr Lys Pro Phe Ser Asp Val Trp Gly Gln Gly
            100                 105                 110

Thr Leu Val Thr Val Ser Ser
        115
```

<210> SEQ ID NO 77
<211> LENGTH: 119
<212> TYPE: PRT
<213> ORGANISM: Artificial Sequence
<220> FEATURE:
<223> OTHER INFORMATION: VH; 1B20 Variant Sequence E1

<400> SEQUENCE: 77

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr Ser Tyr Asn Pro Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Ser Lys Pro Phe Phe Asp Ile Trp Gly Gln Gly
            100                 105                 110

Thr Leu Val Thr Val Ser Ser
        115
```

```
<210> SEQ ID NO 78
<211> LENGTH: 119
<212> TYPE: PRT
<213> ORGANISM: Artificial Sequence
<220> FEATURE:
<223> OTHER INFORMATION: VH; 1B20 Variant Sequence E8

<400> SEQUENCE: 78

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Thr Trp Val Arg Gln Met Pro Gly Lys Gly Leu Glu Trp Met
        35                  40                  45

Gly Met Ile Tyr Pro Gly Asp Ser Tyr Thr Arg Tyr Ser Pro Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Ser Lys Pro Leu Ser Asp Val Trp Gly Gln Gly
            100                 105                 110

Thr Leu Val Thr Val Ser Ser
        115


<210> SEQ ID NO 79
<211> LENGTH: 119
<212> TYPE: PRT
<213> ORGANISM: Artificial Sequence
<220> FEATURE:
<223> OTHER INFORMATION: VH; 1B20 Variant Sequence C1

<400> SEQUENCE: 79

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr Arg Tyr Ser Pro Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Tyr Arg Pro Tyr Ser Asp Ile Trp Gly Gln Gly
            100                 105                 110

Thr Leu Val Thr Val Ser Ser
        115


<210> SEQ ID NO 80
<211> LENGTH: 119
<212> TYPE: PRT
<213> ORGANISM: Artificial Sequence
<220> FEATURE:
<223> OTHER INFORMATION: VH; 1B20 Variant Sequence H3

<400> SEQUENCE: 80

Gln Val Gln Leu Val Gln Ser Gly Ala Glu Val Lys Lys Pro Gly Glu
 1               5                  10                  15
```

```
Ser Leu Lys Ile Ser Cys Lys Gly Ser Gly Tyr Ser Phe Thr Asn Tyr
            20                  25                  30

Tyr Ile Thr Trp Val Arg Gln Met Pro Gly Lys Gly Leu Glu Trp Met
        35                  40                  45

Gly Met Ile Tyr Pro Gly Asp Ser Tyr Thr His Tyr Ser Gln Arg Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Arg Asp His Trp Ser Arg Pro Leu Phe Asp Val Trp Gly Gln Gly
            100                 105                 110

Thr Leu Val Thr Val Ser Ser
        115


<210> SEQ ID NO 81
<211> LENGTH: 119
<212> TYPE: PRT
<213> ORGANISM: Artificial Sequence
<220> FEATURE:
<223> OTHER INFORMATION: VH; 1B20 Variant Sequence A9

<400> SEQUENCE: 81

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr Arg Tyr Ser Pro Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Tyr Arg Pro Tyr Ser Asp Ile Trp Gly Gln Gly
            100                 105                 110

Thr Leu Val Thr Val Ser Ser
        115


<210> SEQ ID NO 82
<211> LENGTH: 119
<212> TYPE: PRT
<213> ORGANISM: Artificial Sequence
<220> FEATURE:
<223> OTHER INFORMATION: VH; 1B20 Variant Sequence G7

<400> SEQUENCE: 82

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Trp Ile Tyr Pro Gly Asp Ser Tyr Thr His Tyr Ser Pro Ser Phe
    50                  55                  60

Gln Gly Gln Val Thr Ile Ser Ala Asp Lys Ser Ile Ser Thr Ala Tyr
65                  70                  75                  80
```

```
Leu Gln Trp Ser Ser Leu Lys Ala Ser Asp Thr Ala Met Tyr Tyr Cys
                85                  90                  95

Ala Arg Asp His Trp Ser Lys Pro Tyr Phe Asp Val Trp Gly Gln Gly
            100                 105                 110

Thr Leu Val Thr Val Ser Ser
        115


<210> SEQ ID NO 83
<211> LENGTH: 119
<212> TYPE: PRT
<213> ORGANISM: Artificial Sequence
<220> FEATURE:
<223> OTHER INFORMATION: VH; 1B20 Variant Sequence C6

<400> SEQUENCE: 83

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Thr Trp Val Arg Gln Met Pro Gly Lys Gly Leu Glu Trp Met
        35                  40                  45

Gly Met Ile Tyr Pro Gly Asp Ser Tyr Thr His Tyr Asn Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Tyr Lys Pro Leu Phe Asp Ile Trp Gly Gln Gly
            100                 105                 110

Thr Leu Val Thr Val Ser Ser
        115


<210> SEQ ID NO 84
<211> LENGTH: 119
<212> TYPE: PRT
<213> ORGANISM: Artificial Sequence
<220> FEATURE:
<223> OTHER INFORMATION: VH; 1B20 Variant Sequence G6

<400> SEQUENCE: 84

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Asn Trp Val Arg Gln Met Pro Gly Lys Gly Leu Glu Trp Met
        35                  40                  45

Gly Met Ile Tyr Pro Gly Asp Ser Tyr Thr Asn Tyr Asn Pro Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Arg Asp His Trp Ser Arg Pro Phe Ser Asp Val Trp Gly Gln Gly
            100                 105                 110

Thr Leu Val Thr Val Ser Ser
        115


<210> SEQ ID NO 85
```

```
<211> LENGTH: 119
<212> TYPE: PRT
<213> ORGANISM: Artificial Sequence
<220> FEATURE:
<223> OTHER INFORMATION: VH; 1B20 Variant Sequence E4

<400> SEQUENCE: 85

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Trp Ile Tyr Pro Gly Asp Ser Tyr Thr Ser Tyr Asn Gln Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Lys Pro Tyr Ser Asp Val Trp Gly Gln Gly
            100                 105                 110

Thr Leu Val Thr Val Ser Ser
        115


<210> SEQ ID NO 86
<211> LENGTH: 119
<212> TYPE: PRT
<213> ORGANISM: Artificial Sequence
<220> FEATURE:
<223> OTHER INFORMATION: VH; 1B20 Variant Sequence F5

<400> SEQUENCE: 86

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Thr Trp Val Arg Gln Met Pro Gly Lys Gly Leu Glu Trp Met
        35                  40                  45

Gly Met Ile Tyr Pro Gly Asp Ser Tyr Thr Asn Tyr Arg His Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Arg Pro Tyr Phe Asp Ile Trp Gly Gln Gly
            100                 105                 110

Thr Leu Val Thr Val Ser Ser
        115


<210> SEQ ID NO 87
<211> LENGTH: 119
<212> TYPE: PRT
<213> ORGANISM: Artificial Sequence
<220> FEATURE:
<223> OTHER INFORMATION: VH; 1B20 Variant Sequence C7

<400> SEQUENCE: 87

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
```

```
            20                  25                  30

Tyr Ile Ser Trp Val Arg Gln Met Pro Gly Lys Gly Leu Glu Trp Met
        35                  40                  45

Gly Trp Ile Tyr Pro Gly Asp Ser Tyr Thr His Tyr Ser His Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Ser Arg Pro Phe Ser Asp Val Trp Gly Gln Gly
            100                 105                 110

Thr Leu Val Thr Val Ser Ser
        115


<210> SEQ ID NO 88
<211> LENGTH: 119
<212> TYPE: PRT
<213> ORGANISM: Artificial Sequence
<220> FEATURE:
<223> OTHER INFORMATION: VH; 1B20 Variant Sequence E3

<400> SEQUENCE: 88

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr Ser Tyr Ser Pro Arg Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Arg Pro Phe Ser Asp Ile Trp Gly Gln Gly
            100                 105                 110

Thr Leu Val Thr Val Ser Ser
        115


<210> SEQ ID NO 89
<211> LENGTH: 119
<212> TYPE: PRT
<213> ORGANISM: Artificial Sequence
<220> FEATURE:
<223> OTHER INFORMATION: VH; 1B20 Variant Sequence D3

<400> SEQUENCE: 89

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Thr Trp Val Arg Gln Met Pro Gly Lys Gly Leu Glu Trp Met
        35                  40                  45

Gly Met Ile Tyr Pro Gly Asp Ser Tyr Thr Arg Tyr Ser Pro Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
```

```
                85                  90                  95

Ala Arg Asp Tyr Trp Ser Lys Pro Phe Phe Asp Val Trp Gly Gln Gly
            100                 105                 110

Thr Leu Val Thr Val Ser Ser
        115


<210> SEQ ID NO 90
<211> LENGTH: 119
<212> TYPE: PRT
<213> ORGANISM: Artificial Sequence
<220> FEATURE:
<223> OTHER INFORMATION: VH; 1B20 Variant Sequence D8

<400> SEQUENCE: 90

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr His Tyr Ser Gln Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Tyr Arg Pro Leu Phe Asp Ile Trp Gly Gln Gly
            100                 105                 110

Thr Leu Val Thr Val Ser Ser
        115


<210> SEQ ID NO 91
<211> LENGTH: 119
<212> TYPE: PRT
<213> ORGANISM: Artificial Sequence
<220> FEATURE:
<223> OTHER INFORMATION: VH; 1B20 Variant Sequence C8

<400> SEQUENCE: 91

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ala Trp Val Arg Gln Met Pro Gly Lys Gly Leu Glu Trp Met
        35                  40                  45

Gly Met Ile Tyr Pro Gly Asp Ser Tyr Thr Ser Tyr Ser His Arg Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp His Trp Tyr Arg Pro Tyr Phe Asp Ile Trp Gly Gln Gly
            100                 105                 110

Thr Leu Val Thr Val Ser Ser
        115


<210> SEQ ID NO 92
<211> LENGTH: 119
<212> TYPE: PRT
```

<213> ORGANISM: Artificial Sequence
<220> FEATURE:
<223> OTHER INFORMATION: VH; 1B20 Variant Sequence E5

<400> SEQUENCE: 92

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Trp Ile Tyr Pro Gly Asp Ser Tyr Thr His Tyr Asn Pro Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Arg Trp Ser Thr Pro Tyr Phe Asp Val Trp Gly Gln Gly
            100                 105                 110

Thr Leu Val Thr Val Ser Ser
        115
```

<210> SEQ ID NO 93
<211> LENGTH: 119
<212> TYPE: PRT
<213> ORGANISM: Artificial Sequence
<220> FEATURE:
<223> OTHER INFORMATION: VH; 1B20 Variant Sequence B8

<400> SEQUENCE: 93

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr His Tyr Ser Pro Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Ser Lys Pro Tyr Phe Asp Val Trp Gly Gln Gly
            100                 105                 110

Thr Leu Val Thr Val Ser Ser
        115
```

<210> SEQ ID NO 94
<211> LENGTH: 119
<212> TYPE: PRT
<213> ORGANISM: Artificial Sequence
<220> FEATURE:
<223> OTHER INFORMATION: VH; 1B20 Variant Sequence H7

<400> SEQUENCE: 94

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30
```

```
Tyr Ile Ser Trp Val Arg Gln Met Pro Gly Lys Gly Pro Glu Trp Met
        35                  40                  45

Gly Met Ile Tyr Pro Gly Asp Ser Tyr Thr Arg Tyr Ser Gln Lys Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Arg Asp His Trp Ser Arg Pro Leu Ser Asp Ile Trp Gly Gln Gly
            100                 105                 110

Thr Leu Val Thr Val Ser Ser
        115


<210> SEQ ID NO 95
<211> LENGTH: 119
<212> TYPE: PRT
<213> ORGANISM: Artificial Sequence
<220> FEATURE:
<223> OTHER INFORMATION: VH; 1B20 Variant Sequence A5

<400> SEQUENCE: 95

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Trp Ile Tyr Pro Gly Asp Ser Tyr Thr His Tyr Asn Pro Met Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Arg Trp Ser Arg Pro Tyr Phe Asp Ile Trp Gly Gln Gly
            100                 105                 110

Thr Leu Val Thr Val Ser Ser
        115


<210> SEQ ID NO 96
<211> LENGTH: 119
<212> TYPE: PRT
<213> ORGANISM: Artificial Sequence
<220> FEATURE:
<223> OTHER INFORMATION: VH; 1B20 Variant Sequence A3

<400> SEQUENCE: 96

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asp Tyr
            20                  25                  30

Tyr Ile Ser Trp Val Arg Gln Met Pro Gly Lys Gly Leu Glu Trp Met
        35                  40                  45

Gly Met Ile Tyr Pro Gly Asp Ser Tyr Thr Arg Tyr Ser Pro Asn Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95
```

```
Ala Arg Asp His Trp Tyr Arg Pro Leu Ser Asp Ile Trp Gly Gln Gly
            100                 105                 110

Thr Leu Val Thr Val Ser Ser
        115


<210> SEQ ID NO 97
<211> LENGTH: 20
<212> TYPE: PRT
<213> ORGANISM: Artificial Sequence
<220> FEATURE:
<223> OTHER INFORMATION: 1B20 Antibody Variant VH CDR2 Sequence
<221> NAME/KEY: VARIANT
<222> LOCATION: 4
<223> OTHER INFORMATION: Xaa = Ile or Arg
<221> NAME/KEY: VARIANT
<222> LOCATION: 13
<223> OTHER INFORMATION: Xaa = Asn, Arg, His or Ser
<221> NAME/KEY: VARIANT
<222> LOCATION: 16
<223> OTHER INFORMATION: Xaa = Pro or Gln

<400> SEQUENCE: 97

Trp Met Gly Xaa Ile Tyr Pro Gly Asp Ser Tyr Thr Xaa Tyr Ser Xaa
 1               5                  10                  15

Ser Phe Gln Gly
            20


<210> SEQ ID NO 98
<211> LENGTH: 10
<212> TYPE: PRT
<213> ORGANISM: Artificial Sequence
<220> FEATURE:
<223> OTHER INFORMATION: 1B20 Antibody Variant VH CDR3 Sequence
<221> NAME/KEY: VARIANT
<222> LOCATION: 5
<223> OTHER INFORMATION: Xaa = Lys, Gly, Arg, Ser, Asp, Glu, His, Asn or
      Gln
<221> NAME/KEY: VARIANT
<222> LOCATION: 6
<223> OTHER INFORMATION: Xaa = Pro, Gly, Asp, Ser, Ala, His, Arg or Tyr
<221> NAME/KEY: VARIANT
<222> LOCATION: 7
<223> OTHER INFORMATION: Xaa = Leu, Ala, Tyr, Asp, Phe, His, Pro, Ser or
      Val
<221> NAME/KEY: VARIANT
<222> LOCATION: 10
<223> OTHER INFORMATION: Xaa = Ile, Tyr, Phe or Asn

<400> SEQUENCE: 98

Asp Tyr Trp Tyr Xaa Xaa Xaa Phe Asp Xaa
 1               5                  10


<210> SEQ ID NO 99
<211> LENGTH: 17
<212> TYPE: PRT
<213> ORGANISM: Artificial Sequence
<220> FEATURE:
<223> OTHER INFORMATION: 1B20 Antibody Variant VL CDR1 Sequence
<221> NAME/KEY: VARIANT
<222> LOCATION: 15
<223> OTHER INFORMATION: Xaa = Tyr or Phe
<221> NAME/KEY: VARIANT
<222> LOCATION: 17
<223> OTHER INFORMATION: Xaa = Ala or Thr

<400> SEQUENCE: 99

Arg Ser Ser Gln Ser Val Leu Tyr Ser Ser Asn Asn Lys Asn Xaa Leu
 1               5                  10                  15

Xaa
```

```
<210> SEQ ID NO 100
<211> LENGTH: 11
<212> TYPE: PRT
<213> ORGANISM: Artificial Sequence
<220> FEATURE:
<223> OTHER INFORMATION: 1B20 Antibody Variant VL CDR2 Sequence
<221> NAME/KEY: VARIANT
<222> LOCATION: 5
<223> OTHER INFORMATION: Xaa = Trp, Phe or Leu
<221> NAME/KEY: VARIANT
<222> LOCATION: 10
<223> OTHER INFORMATION: Xaa = Glu or Lys
<221> NAME/KEY: VARIANT
<222> LOCATION: 11
<223> OTHER INFORMATION: Xaa = Ser or Thr

<400> SEQUENCE: 100

Leu Leu Ile Tyr Xaa Ala Ser Thr Arg Xaa Xaa
 1               5                  10


<210> SEQ ID NO 101
<211> LENGTH: 8
<212> TYPE: PRT
<213> ORGANISM: Artificial Sequence
<220> FEATURE:
<223> OTHER INFORMATION: 1B20 Antibody Variant VL CDR3 Sequence
<221> NAME/KEY: VARIANT
<222> LOCATION: 6
<223> OTHER INFORMATION: Xaa = Phe, Tyr, Thr, Ile, Asn or Ser
<221> NAME/KEY: VARIANT
<222> LOCATION: 8
<223> OTHER INFORMATION: Xaa = Ile, Tyr, Arg, Phe, His, Leu, Asn or Ser

<400> SEQUENCE: 101

Gln Gln Tyr Ser Ser Xaa Pro Xaa
 1               5


<210> SEQ ID NO 102
<211> LENGTH: 119
<212> TYPE: PRT
<213> ORGANISM: Artificial Sequence
<220> FEATURE:
<223> OTHER INFORMATION: 1B20 Antibody Variant VH Sequence N59K

<400> SEQUENCE: 102

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Lys Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Lys Pro Leu Phe Asp Ile Trp Gly Gln Gly
            100                 105                 110

Thr Leu Val Thr Val Ser Ser
        115


<210> SEQ ID NO 103
<211> LENGTH: 119
<212> TYPE: PRT
<213> ORGANISM: Artificial Sequence
<220> FEATURE:
```

<223> OTHER INFORMATION: 1B20 Antibody Variant VH Sequence N59Q

<400> SEQUENCE: 103

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Gln Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Lys Pro Leu Phe Asp Ile Trp Gly Gln Gly
            100                 105                 110

Thr Leu Val Thr Val Ser Ser
        115
```

<210> SEQ ID NO 104
<211> LENGTH: 119
<212> TYPE: PRT
<213> ORGANISM: Artificial Sequence
<220> FEATURE:
<223> OTHER INFORMATION: 1B20 Antibody Variant VH Sequence N59R

<400> SEQUENCE: 104

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Lys Pro Leu Phe Asp Ile Trp Gly Gln Gly
            100                 105                 110

Thr Leu Val Thr Val Ser Ser
        115
```

<210> SEQ ID NO 105
<211> LENGTH: 119
<212> TYPE: PRT
<213> ORGANISM: Artificial Sequence
<220> FEATURE:
<223> OTHER INFORMATION: 1B20 Antibody Variant VH Sequence W101A

<400> SEQUENCE: 105

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45
```

```
Gly Ile Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Ala Tyr Lys Pro Leu Phe Asp Ile Trp Gly Gln Gly
            100                 105                 110

Thr Leu Val Thr Val Ser Ser
        115


<210> SEQ ID NO 106
<211> LENGTH: 119
<212> TYPE: PRT
<213> ORGANISM: Artificial Sequence
<220> FEATURE:
<223> OTHER INFORMATION: 1B20 Antibody Variant VH Sequence W101F

<400> SEQUENCE: 106

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Phe Tyr Lys Pro Leu Phe Asp Ile Trp Gly Gln Gly
            100                 105                 110

Thr Leu Val Thr Val Ser Ser
        115


<210> SEQ ID NO 107
<211> LENGTH: 119
<212> TYPE: PRT
<213> ORGANISM: Artificial Sequence
<220> FEATURE:
<223> OTHER INFORMATION: 1B20 Antibody Variant VH Sequence W101Y

<400> SEQUENCE: 107

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Tyr Tyr Lys Pro Leu Phe Asp Ile Trp Gly Gln Gly
            100                 105                 110
```

```
Thr Leu Val Thr Val Ser Ser
        115


<210> SEQ ID NO 108
<211> LENGTH: 114
<212> TYPE: PRT
<213> ORGANISM: Artificial Sequence
<220> FEATURE:
<223> OTHER INFORMATION: VL; 1B20 VARIANT SEQUENCE
<221> NAME/KEY: VARIANT
<222> LOCATION: 38
<223> OTHER INFORMATION: Xaa = Tyr or Phe
<221> NAME/KEY: VARIANT
<222> LOCATION: 40
<223> OTHER INFORMATION: Xaa = Ala or Thr
<221> NAME/KEY: VARIANT
<222> LOCATION: 56
<223> OTHER INFORMATION: Xaa = Trp, Phe or Leu
<221> NAME/KEY: VARIANT
<222> LOCATION: 61
<223> OTHER INFORMATION: Xaa = Glu or Lys
<221> NAME/KEY: VARIANT
<222> LOCATION: 62
<223> OTHER INFORMATION: Xaa = Ser or Thr
<221> NAME/KEY: VARIANT
<222> LOCATION: (100)...(100)
<223> OTHER INFORMATION: Xaa = Phe, Tyr, Thr, Ile, Asn or Ser
<221> NAME/KEY: VARIANT
<222> LOCATION: (102)...(102)
<223> OTHER INFORMATION: Xaa = Ile, Tyr, Arg, Phe, His, Leu, Asn or Ser

<400> SEQUENCE: 108

Asp Ile Val Met Thr Gln Ser Pro Asp Ser Leu Ala Val Ser Leu Gly
 1               5                  10                  15

Glu Arg Ala Thr Ile Asn Cys Arg Ser Ser Gln Ser Val Leu Tyr Ser
            20                  25                  30

Ser Asn Asn Lys Asn Xaa Leu Xaa Trp Tyr Gln Gln Lys Pro Gly Gln
        35                  40                  45

Pro Pro Lys Leu Leu Ile Tyr Xaa Ala Ser Thr Arg Xaa Xaa Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Ser Xaa Pro Xaa Thr Phe Gly Gln Gly Thr Lys Val Glu Ile
            100                 105                 110

Lys Arg


<210> SEQ ID NO 109
<211> LENGTH: 119
<212> TYPE: PRT
<213> ORGANISM: Artificial Sequence
<220> FEATURE:
<223> OTHER INFORMATION: VH; 1B20 VARIANT SEQUENCE
<221> NAME/KEY: VARIANT
<222> LOCATION: 31
<223> OTHER INFORMATION: Xaa = Asn or Asp
<221> NAME/KEY: VARIANT
<222> LOCATION: 33
<223> OTHER INFORMATION: Xaa = Trp or Tyr
<221> NAME/KEY: VARIANT
<222> LOCATION: 35
<223> OTHER INFORMATION: Xaa = Ser, Thr or Ala
<221> NAME/KEY: VARIANT
<222> LOCATION: 50
<223> OTHER INFORMATION: Xaa = Ile or Arg
<221> NAME/KEY: VARIANT
<222> LOCATION: 59
<223> OTHER INFORMATION: Xaa = Asn, Arg, His, Ser, Lys or Gln
```

```
<221> NAME/KEY: VARIANT
<222> LOCATION: (62)...(62)
<223> OTHER INFORMATION: Xaa = Pro or Gln
<221> NAME/KEY: VARIANT
<222> LOCATION: (103)...(103)
<223> OTHER INFORMATION: Xaa = Lys, Gly, Arg, Ser, Asp, Glu, His, Asn or
      Gln
<221> NAME/KEY: VARIANT
<222> LOCATION: (104)...(104)
<223> OTHER INFORMATION: Xaa = Pro, Gly, Asp, Ser, Ala, His, Arg or Tyr
<221> NAME/KEY: VARIANT
<222> LOCATION: (105)...(105)
<223> OTHER INFORMATION: Xaa = Leu, Ala, Tyr, Asp, Phe, His, Pro, Ser or
      Val
<221> NAME/KEY: VARIANT
<222> LOCATION: (108)...(108)
<223> OTHER INFORMATION: Xaa = Ile, Tyr, Phe or Asn

<400> SEQUENCE: 109

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Xaa Tyr
            20                  25                  30

Xaa Ile Xaa Trp Val Arg Gln Met Pro Gly Lys Gly Leu Glu Trp Met
        35                  40                  45

Gly Xaa Ile Tyr Pro Gly Asp Ser Tyr Thr Xaa Tyr Ser Xaa Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Xaa Xaa Xaa Phe Asp Xaa Trp Gly Gln Gly
            100                 105                 110

Thr Leu Val Thr Val Ser Ser
        115
```